US009156809B2

(12) United States Patent
Rieth et al.

(10) Patent No.: US 9,156,809 B2
(45) Date of Patent: *Oct. 13, 2015

(54) CARBOXY ESTER KETALS, METHODS OF MANUFACTURE, AND USES THEREOF

(71) Applicant: SEGETIS, INC., Golden Valley, MN (US)

(72) Inventors: Lee R. Rieth, Plymouth, MN (US); Dorie J. Yontz, Bloomington, MN (US)

(73) Assignee: SEGETIS, INC., Golden Valley, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/092,176

(22) Filed: Nov. 27, 2013

(65) Prior Publication Data

US 2014/0147395 A1    May 29, 2014

Related U.S. Application Data

(60) Provisional application No. 61/731,194, filed on Nov. 29, 2012.

(51) Int. Cl.
| | |
|---|---|
| *C07D 317/30* | (2006.01) |
| *A61Q 11/00* | (2006.01) |
| *C09D 7/12* | (2006.01) |
| *C11D 3/20* | (2006.01) |
| *C11B 9/00* | (2006.01) |
| *C11D 3/50* | (2006.01) |
| *C09D 5/02* | (2006.01) |
| *C09D 7/00* | (2006.01) |
| *C09D 9/00* | (2006.01) |
| *A61K 8/49* | (2006.01) |
| *A61Q 13/00* | (2006.01) |
| *C09D 11/00* | (2014.01) |
| *C08K 5/06* | (2006.01) |
| *A61Q 5/06* | (2006.01) |
| *A61Q 5/10* | (2006.01) |
| *A61Q 17/04* | (2006.01) |

(52) U.S. Cl.
CPC ............... *C07D 317/30* (2013.01); *A61K 8/498* (2013.01); *A61Q 11/00* (2013.01); *A61Q 13/00* (2013.01); *C09D 5/024* (2013.01); *C09D 7/001* (2013.01); *C09D 7/1233* (2013.01); *C09D 9/00* (2013.01); *C11B 9/008* (2013.01); *C11B 9/0076* (2013.01); *C11D 3/2096* (2013.01); *C11D 3/50* (2013.01); *A61Q 5/065* (2013.01); *A61Q 5/10* (2013.01); *A61Q 17/04* (2013.01); *C08K 5/06* (2013.01); *C09D 11/00* (2013.01)

(58) Field of Classification Search
CPC .................................................. C07D 317/30
See application file for complete search history.

(56) References Cited

U.S. PATENT DOCUMENTS

| | | |
|---|---|---|
| 1,934,309 A | 11/1933 | Hoover |
| 2,004,115 A | 6/1935 | Izard |
| 2,008,720 A | 7/1935 | Lawson |
| 2,260,261 A | 10/1941 | Morey et al. |
| 2,556,135 A | 6/1951 | Croxall et al. |
| 2,654,723 A | 10/1953 | Greene |
| 2,985,536 A | 5/1961 | Stein et al. |
| 3,201,420 A | 8/1965 | Fuzesi et al. |
| 3,658,789 A | 4/1972 | Fried |
| 3,821,363 A | 6/1974 | Black et al. |
| 3,855,248 A | 12/1974 | Lannert et al. |
| 3,895,104 A | 7/1975 | Karg |
| 4,005,210 A | 1/1977 | Gubernick |
| 4,153,064 A | 5/1979 | Sawada et al. |
| 4,172,122 A | 10/1979 | Kubik et al. |
| 4,193,989 A | 3/1980 | Teng et al. |
| 4,387,089 A | 6/1983 | De Polo |
| 4,460,767 A | 7/1984 | Matsumura et al. |
| 4,465,866 A | 8/1984 | Takaishi et al. |

(Continued)

FOREIGN PATENT DOCUMENTS

| | | |
|---|---|---|
| CA | 1000285 | 11/1976 |
| CA | 2347255 A1 | 2/2004 |

(Continued)

OTHER PUBLICATIONS

Black, C., et al. "The Solubility of Water in Hydrocarbons." The Journal of Chemical Physics. (1948), vol. 16, pp. 537-543.*

(Continued)

*Primary Examiner* — Andrew D Kosar
*Assistant Examiner* — John S Kenyon
(74) *Attorney, Agent, or Firm* — Cantor Colburn LLP

(57) ABSTRACT

This disclosure is directed to compound of formula (1):

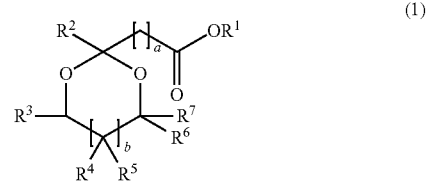

wherein $R^1$ is a $C_{7-18}$ alkyl, $R^2$ is hydrogen or a $C_{1-3}$ alkyl, each $R^3$, $R^4$, $R^5$, $R^6$, and $R^7$ is independently hydrogen or a $C_{1-6}$ alkyl, a is 2-3, and b is 0-1, its method of preparation and uses thereof in water-borne coating compositions, cleaning compositions, fragrance, and personal care compositions.

31 Claims, No Drawings

(56) References Cited

U.S. PATENT DOCUMENTS

| | | |
|---|---|---|
| 4,562,067 A | 12/1985 | Hopp |
| 4,663,157 A | 5/1987 | Brock |
| 4,668,505 A | 5/1987 | Grollier et al. |
| 4,710,373 A | 12/1987 | Nakamura et al. |
| 4,724,240 A | 2/1988 | Abrutym |
| 4,731,242 A | 3/1988 | Palinczar |
| 4,737,426 A | 4/1988 | Roth |
| 4,792,411 A | 12/1988 | Walsh |
| 4,806,448 A | 2/1989 | Roth |
| 4,847,072 A | 7/1989 | Bissett et al. |
| 4,897,497 A | 1/1990 | Fitzpatrick |
| 5,013,543 A | 5/1991 | Mercado et al. |
| 5,093,111 A | 3/1992 | Baker et al. |
| 5,116,604 A | 5/1992 | Fogel et al. |
| 5,145,669 A | 9/1992 | Kwak et al. |
| 5,204,090 A | 4/1993 | Han |
| 5,208,011 A | 5/1993 | Vaughan |
| 5,266,592 A | 11/1993 | Grub et al. |
| 5,302,376 A | 4/1994 | Forestier et al. |
| 5,419,848 A | 5/1995 | Van Eenam |
| 5,455,025 A | 10/1995 | Pereira et al. |
| 5,489,448 A | 2/1996 | Jackson et al. |
| 5,505,935 A | 4/1996 | Guerrero et al. |
| 5,516,459 A | 5/1996 | Van Eenam |
| 5,573,755 A | 11/1996 | Franklin et al. |
| 5,605,680 A | 2/1997 | Deflandre et al. |
| 5,608,105 A | 3/1997 | Fitzpatrick |
| 5,620,682 A | 4/1997 | Fogel |
| 5,653,965 A | 8/1997 | Narayanan et al. |
| 5,667,765 A | 9/1997 | Hansenne et al. |
| 5,672,337 A | 9/1997 | Ascione et al. |
| 5,700,522 A | 12/1997 | Nonweiler et al. |
| 5,705,087 A | 1/1998 | Mushrush et al. |
| 5,725,844 A | 3/1998 | Gers-Barlag et al. |
| 5,783,174 A | 7/1998 | Deckner |
| 5,859,263 A | 1/1999 | Ghorpade et al. |
| 5,886,136 A | 3/1999 | Tanaka et al. |
| 5,917,059 A | 6/1999 | Bruchmann et al. |
| 5,998,092 A | 12/1999 | McCulloch et al. |
| 6,010,995 A | 1/2000 | Van Eenam |
| 6,034,118 A | 3/2000 | Bischofberger et al. |
| 6,036,925 A | 3/2000 | Adams et al. |
| 6,048,517 A | 4/2000 | Kaplan |
| 6,071,501 A | 6/2000 | Robinson |
| 6,083,490 A | 7/2000 | Ellis et al. |
| 6,130,195 A | 10/2000 | Doyel et al. |
| 6,238,650 B1 | 5/2001 | Lapidot et al. |
| 6,239,087 B1 | 5/2001 | Mao et al. |
| 6,306,249 B1 | 10/2001 | Galante et al. |
| 6,312,672 B1 | 11/2001 | Coolbaugh et al. |
| 6,372,791 B1 | 4/2002 | Shapiro et al. |
| 6,395,269 B1 | 5/2002 | Fuller et al. |
| 6,395,810 B1 | 5/2002 | Luitjes et al. |
| 6,423,480 B2 | 7/2002 | Ichiki |
| 6,423,677 B1 | 7/2002 | Van Eenam |
| 6,444,195 B1 | 9/2002 | Cole et al. |
| 6,451,223 B1 | 9/2002 | Jeon |
| 6,485,713 B1 | 11/2002 | Bonda et al. |
| 6,528,025 B1 | 3/2003 | Boesch et al. |
| 6,627,181 B1 | 9/2003 | Busch, Jr. et al. |
| 6,703,478 B2 | 3/2004 | Nakane et al. |
| 6,749,998 B2 | 6/2004 | Schwartzkopf et al. |
| 6,806,392 B2 | 10/2004 | Boesch et al. |
| 6,844,302 B1 | 1/2005 | Boden et al. |
| 6,962,767 B2 | 11/2005 | Watanabe et al. |
| 7,094,395 B1 | 8/2006 | Qu et al. |
| 7,108,860 B2 | 9/2006 | Dueva et al. |
| 7,166,273 B2 | 1/2007 | Chaudhuri |
| 7,175,834 B2 | 2/2007 | Aust et al. |
| 7,179,775 B2 | 2/2007 | Foster |
| 7,705,081 B2 | 4/2010 | Porzio et al. |
| 2002/0183234 A1 | 12/2002 | Jalalian et al. |
| 2003/0036489 A1 | 2/2003 | Liu et al. |
| 2003/0133895 A1 | 7/2003 | China et al. |
| 2004/0018954 A1 | 1/2004 | Su et al. |
| 2004/0024260 A1 | 2/2004 | Winkler et al. |
| 2004/0052737 A1 | 3/2004 | Hill |
| 2004/0120918 A1 | 6/2004 | Lintner et al. |
| 2004/0138090 A1 | 7/2004 | Drapier et al. |
| 2004/0147602 A1 | 7/2004 | Smith et al. |
| 2004/0157759 A1 | 8/2004 | Scherubel |
| 2004/0167245 A1 | 8/2004 | Chappelow et al. |
| 2005/0031576 A1 | 2/2005 | McManus et al. |
| 2005/0106112 A1 | 5/2005 | Boyd et al. |
| 2005/0228125 A1 | 10/2005 | Poellmann et al. |
| 2005/0233927 A1 | 10/2005 | Scherubel |
| 2006/0069230 A1 | 3/2006 | Papisov |
| 2006/0134045 A1 | 6/2006 | Cao et al. |
| 2006/0165622 A1 | 7/2006 | Hiramoto |
| 2006/0207037 A1 | 9/2006 | Fadel et al. |
| 2006/0208226 A1 | 9/2006 | Maze et al. |
| 2006/0211855 A1 | 9/2006 | Doring et al. |
| 2007/0079722 A1 | 4/2007 | Parish |
| 2007/0111917 A1 | 5/2007 | Lang et al. |
| 2007/0161530 A1 | 7/2007 | Kaneda et al. |
| 2007/0298000 A1 | 12/2007 | Grune |
| 2008/0096785 A1 | 4/2008 | Egbe et al. |
| 2008/0124426 A1 | 5/2008 | Kobler et al. |
| 2008/0188603 A1 | 8/2008 | Porzio et al. |
| 2008/0242721 A1 | 10/2008 | Selifonov |
| 2008/0305978 A1 | 12/2008 | Wietfeldt et al. |
| 2009/0035234 A1 | 2/2009 | Cunningham et al. |
| 2009/0053153 A1 | 2/2009 | Lee et al. |
| 2009/0124531 A1 | 5/2009 | Danziger et al. |
| 2009/0281012 A1 | 11/2009 | Trivedi et al. |
| 2010/0087357 A1 | 4/2010 | Morgan, III et al. |
| 2011/0130470 A1 | 6/2011 | Kraft |
| 2011/0196081 A1 | 8/2011 | Kwon et al. |
| 2011/0274634 A1 | 11/2011 | Rieth |
| 2011/0300083 A1 | 12/2011 | Yontz et al. |

FOREIGN PATENT DOCUMENTS

| | | |
|---|---|---|
| DE | 3220035 A1 | 1/1983 |
| DE | 10036423 A1 | 3/2001 |
| EP | 012543 A1 | 6/1980 |
| EP | 0308956 A2 | 3/1989 |
| EP | 0507190 A1 | 10/1992 |
| EP | 0913463 A1 | 5/1999 |
| FR | 1445013 | 7/1966 |
| JP | 284327 | 9/1953 |
| JP | 28004327 A | 9/1953 |
| JP | 58124711 A | 7/1983 |
| JP | 59164712 A | 9/1984 |
| JP | 4217972 | 8/1992 |
| JP | 5320023 A | 12/1993 |
| JP | 5320042 A | 12/1993 |
| JP | H07228887 A | 8/1995 |
| JP | 2004075586 | 3/2004 |
| JP | 2005143466 A | 6/2005 |
| JP | 2006022119 A | 1/2006 |
| JP | 2006143702 A | 6/2006 |
| JP | 2009035733 A | 2/2009 |
| JP | 2009179624 A | 8/2009 |
| SU | 722912 | 3/1980 |
| WO | 9412489 A1 | 6/1994 |
| WO | 9856889 | 12/1998 |
| WO | 2004099173 A1 | 11/2004 |
| WO | 2005058265 A1 | 6/2005 |
| WO | 2005095378 A2 | 10/2005 |
| WO | 2005097723 A2 | 10/2005 |
| WO | 2005097724 A1 | 10/2005 |
| WO | 2007062158 A2 | 5/2007 |
| WO | 2007094922 A2 | 8/2007 |
| WO | 2008046795 A1 | 4/2008 |
| WO | 2008089463 A2 | 7/2008 |
| WO | 2008098375 A1 | 8/2008 |
| WO | 2009032905 A1 | 3/2009 |
| WO | 2009065244 A1 | 6/2009 |
| WO | 2010075330 | 7/2010 |
| WO | 2011047420 A1 | 4/2011 |
| WO | WO2012021824 A2 * | 2/2012 |

(56) References Cited

FOREIGN PATENT DOCUMENTS

| WO | WO2012021826 A2 * | 2/2012 |
| WO | WO2012054505 A2 * | 4/2012 |

OTHER PUBLICATIONS

Takenishi, et al., The Syntheses from Levulinic Acid. A Possible Use of Some 2 Methyl-5-oxopyrrolidine-2 carboxylic Esters as Plasticizers, 27(4): 207-209 (1954).

Wang, et al., "An efficient procedure for protection of carbonyls catalyzed by sulfamic acid," Journal of Molecular Catalysis A: Chemical 233: 121-126 (2005).

Wedmid, et al., "Long-Chain Stereomeric 2-Alkyl-4-methoxycarbonyl-1,3-dioxolanes in Glycerol Acetal Synthesis," J. Org. Chem. 42(22): 3624-3626 (1977).

Yamaguchi, Masahiko, "Synthesis of Polycyclic Aromatic Compounds via Polyketides," Yuki Gosei Kagaku Kyokaishi 45(10) 969-982 (1987) (Chinese—Translation of Abstract Only).

Yang, et al., "Investigation of homopolymerization rate of perfluoro-4,5-substituted-2-methylene-1,3-dioxolane derivatives and properties of the polymers," Journal of Flourine Science 127: 277-281 (2006).

Yulan, et al., "Synthesis of Ketals of 4-Oxopentanoates," Lanzhou Daxue Xuebao, Ziran Kexueban 30(2): 66-70 (1994).

Zhang, et al., "Synthesis of Ketals of 4-Oxopentanoates," Lanzhou Daxue Xuebao, Ziran Kexueban 30(2): 66-70 (1994).

Anderson, et al., "Preparation of Carboxylic Acids from Protected Aldehydes," J. Org. Chem. 43(17): 3417-3418 (1978).

Boehm, R., "Knowledge on cyclic ketals. Part 11: Synthesis of some new derivatives and separation of their isomers," Pharmazie 36(5): 329-330 (1981).

Brigl, Percy, et al., "The Reaction of the Pyruvic Acid with Glycerin," Annalen der Chemie 476: p. 215-232, (with English translation).

Briol, et al., "Reaction of pyroracemic acid with glycerol," Ann. 476: 215-232 (1929).

Bulat, J.A., "A practical synthesis of cis-jasmone from levulinic acid", Canadian J. of Chem, 54, Dec. 15, 1976, p. 3869-3871.

Calinaud, et al., "Cyclic acetal series. XIII. Opening of 4-oxo and 4-hydroxy-3,6,8-trioxabicyclo[3.2.1]octane and 3-pxp-2,5,7-trioxabicyclo[2.2.2]octane rings by lithium aluminum hydride and methylmagnesium iodide," Carbohydrate Research 30(1) 35-43 (1973).

Campbell, I.D., "The Hydration of Undeca-1,7-diyne", J. of Chemical Society, Jan. 1, 1964, 1092-1096.

Carey, et al., "Advanced Organic Chemistry, Second Edition, Part B: Reactions and Synthesis," Plenum Press 539-552 (1983).

Chirila, T., "Pent-and hexatomic cycloacetal esters. Synthesis and characterization of some 2-Carbalkoxymethyl-1,3-dioxolanes (dioxanes)," Revista de Chimie 28: 730-733 (1977).

Cross, Brian E. and Zammitt, Leslie J., "Part 111 Synthesis of a Methyl Ether of Bisdeoxyerythrostominone", J. Chemical Society, Perkins Transactions 1, No. 19, Jan. 1, 1975, pp. 1936-1941.

Cuiling, et al., "Synthesis of Levulinic Ketals with Furfuryl Alcohol as Raw Material," Journal of Huagiao University (Nature Science) 23(3): 257-259 (2002) (English Translation).

Doedens, Robert J., Transition-State Geometry of [3,3]-Sigmatropic Rearrangements of Iminium IOns, J. of Org. Chem, 53, Feb. 1, 1988, p. 685-690.

Doolittle, Arthur K., "Application of a Mechanistic Theory of Solvent Action to Plasticizers and Platicization", Journal of Polymer Science, vol. 2, No. 2 (1947) 121-141.

Eastman Chemical Company. (May 2006). Selecting Coupling Agents for Multi-phase Models. Retrieved Aug. 13, 2009, from http://www.eastman.com/Literature Center/M/M207.pdf.

Fu, Hongbo, "Synthesis and Application of Fructose", Application of Toothpaste, No. 3, pp. 23-24, with English Abstract.

Gasparrini, et al., "Synthesis of Dimethyl Acetals, Diethyl Acetals, and Cyclic Acetals Catalyzed by AminoPropylated Silica Gel Hydrochloride," Tetrahedron 40(9): 1491-1500 (1984).

Gelas, et al., "Synthese du 4-oxo et de 4-hydroxy-3,6,8-trioxabicyclo[3.2.1]octanes," Carbohydrate Research 30(1): 21-34 (1973) (with English abstract).

Girisuta, et al., "Green Chemicals a Kinetic Study on the Conversion of Glucose to Levulinic Acid," Chemical Engineering Research and Design 84(A5) 339-349 (2006).

Girisuta, et al., "Kinetic Study on the Acid-Catalyzed Hydrolysis of Cellulose to Levulinic Acid," Ind. Eng. Chem. Res. 46: 1696-1708 (2007).

Glansdorp, Freija G., et al., "Synthesis and stability of small molecule probes for *Pseudomonas aeruginosa* quorum sensing modulation", Org. Biomol. Chem., vol. 2, 2004, p. 3330-3336.

Gonzalez, et al., "Application of Fourier Transform Infrared Spectroscopy in the Study of Interactions Between PVC and Plasticizers: PVC/Plasticizer Compatibility versus Chemical Structure of Plasticizer," Journal of Applied Polymer Science 101: 1731-1737 (2006).

Grosu, et al., "Stereochemistry and NMR Spectra of Some New Unsymmetrical Substituted 2,2-Dialkyl-1,3-Dioxanes," Revue Roumaine de Chimie 41(3-4): 259-263 (1996).

Gutsche, et al., "Reactions of Ethyl Diazoacetate with Aromatic Compounds Containing Hetero Atoms Attached to the Benzyl Carbon," J. Am. Chem. Soc. 76: 2236-2240 (1954).

Haskelbhrg, L., "The preparation of glycerol esters of amino acids," Compt. rend. 190270-190272 (1930).

Hegde, et al., "The Kinetics and Thermodynamics of Bicyclic Ketal Formation: An Application to the Synthesis of the Zaragozic Acids," Tetrahedron 53(32): 11179-11190 (1997).

Holmberg, Krister, "Surfactants with controlled half-lives", Current Opinion in Colloid & Interface Science, 1, p. 572-579 (1996).

Holmberg, Krister, "Surfactants with controlled half-lives", Current Opinion in Colloid & Interface Science, vol. 1, Issue 5, pp. 572-579 (Oct. 1996).

Horn, Mihai, et al. "Synthesis and Conformational Analysis of Some 2-Alkyloxycarbonyl Substituted 1,3-Dioxanes", Studia Univ. Babes-Bolyai, Chemia XL, 1-2, 1995, p. 99-108.

Horsfall, et al., "Fungitoxicity of Dioxanes, Dioxolanes, and Methylenedioxybenzenes," The Connecticut Agricultrual Experiment Station New Haven, Bulletin 673: 1-44, Jun. 1965.

Krohn, Karsten and Schafer, Gisbert, "Synthesis of Protected 4-Deoxyaklanonic Acid via Naphthalene-Substituted Oligo ketides", Liebigs Ann. 1996, 265-270.

Lenz, Robert W., "Structure, Properties, and Cross-linking Reactions of Poly(ester acetals)," Macromolecules 2(2): 129-136 (1969).

Li, et al., "Montmorillonite Clay Catalysis. Part 2. An Efficient and Convenient Procedure for the Preparation of Acetals Catalysed by Montmorillonite K-10," J. Chem Research (S) 26-27 (1997).

Lindblad, et al., "Polymers from Renewable Resources," Advances in Polymer Science 157: 139-161 (2002).

Lukes, Robert M., Preparation of Methyl Esters Containing the 1,3-Dioxane or 2,4,8,10-Tetroxaspiro[5.5]undecane Structure by Ketal Exchange, 26: 2515-2518 (1961).

Rohm and Haas. (Apr. 1998). Maincote PR-71 Technical Data Sheet. Retrieved Mar. 4, 2009 from http://www.rohmhaas.com/assets/attachments/business/pcm/maincote_pr/maincote_pr071/tds/maincote_pr-71.pdf.

Meltzer, et al., "2,2-Disubstituted 1,3-Dioxolanes and 2,2-Disubstituted 1,3-Dioxanes," JOC 25: 712-715 (1960).

Meskens, Frans A.J., "Methods for the Preparation of Acetals from Alcohols or Oxiranes and Carbonyl Compounds," Synthesis 501-522 (1981).

Nagata, et al., "Synthesis and Applications of [2-Methyl-2(oxoalkyl)-1,3-dioxolan-4-yl] methyl Acrylates for Photocrosslinking Agent," Osaka Kogyo Gijutsu Shikensho Kiho 37(1): 8-16 (1986).

Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).

Newman, et al.,"Kinetic and Equilibrium Studies of Cyclic Ketal Formation and Hydrolysis," The Journal of the American Oil Chemist's Society 80: 6350-6355 (1958).

(56) References Cited

OTHER PUBLICATIONS

Nicolaou, K.C., et al., "Asymmetric Total Syntheses of Platensimycin", Angew. Chem. Int. Ed. 2007, 46, 3942-3945.

Ono, et al., "Synthesis and Properties of Soap Types of Cleavable Surfactants Bearing a 1,3-Dioxolane Ring Derived from Long-chain Epoxides and Ethyl Levulinate," J. Jpn. Oil Chem. Soc. 42(12): 965-971 (1993).

Otera, Junzo, "Esterification, Methods, Reactions, and Applications," Wiley-VCH Verlag GmbH & Co., 1-19 (2003).

Pasto, et al., "Neighboring Group Participation by Carbonyl Oxygen," Journal of the American Chemical Society 87(7): 1515-1521 (1965).

Rohm and Haas Rhoplex SG-10M Technical Data Sheet. (Jun. 1997). Retrieved Mar. 9, 2009, from http://www.rohmhaas.com/assets/attachments/business/pcm/rhoplex_sg/rhoplex_sg-10m/tds/rhoplex_sg-10m.pdf.

Sakuda, Shohei, et al., "Biosynthetic Studies on Virginiae Butanolide A, a Butyrolactone Autoregulator from *Streptomyces*. Part 2. Preparation of Possible Biosynthetic Intermediates and Conversion Experiments in a Cell-free System", J. Chem. Soc. Perkin Trans., 1993, p. 2309-2315.

Schnebel, Matthias, et al., "Reactions between Benzocyclobutenone Tricarbonylchromium Complexes and Lithium Dialkylphosphides: A New Route to Isochromanones", Eur. J. Org. Chem., 2003, No. 22, 4363-4372.

Showler, et al., "Condensation Products of Glycerol with Aldehydes and Ketones. 2-Substituted m-Dioxan-5-OLS and 1,3-dioxolane-4-methanols," Chem. Rev. 67: 427-440 (1967).

Smith, et al., "The gem-Dialkyl Effect. III. Kinetic and Equilibrium Studies of Steroid Cyclic Ketal Formation and Hydrolysis," Journal of the American Chemical Society 90(5): 1253-1257 (1968).

STIC Search Report dated Jul. 5, 2013, 90 pages.

International Search Report of the International Searching Authority for PCT/US2013/072268 mailed Apr. 1, 2014, 7 pages.

Written Opinion of the International Searching Authority for PCT/US2013/072268 mailed Apr. 1, 2014, 7 pages.

Wu, Cuiling, et al., "Synthesis of Levulinate Ester Ketal Taking Sugar Alcohol as Raw Materials", Journal of Huagiao University (Natural Science), vol. 23, No. 3, pp. 257-259 (Jul. 2002) with English Abstract.

European Search Report for European Application No. 11781170.3, Report Date Dec. 17, 2014, 12 pages.

Extended European Search Report for European Application No. 11781171.1; Search Report Date Dec. 19, 2014; 10 pages.

Gelas, et al., "Organic Chemistry. Dihydroxyl Cyclic Acetals Derived from Glycerol," C.R. Acad. Sc. Paris t. 271: Series C, 218-220 (1970) (English Translation).

Kim, et al., "Transesterification of vegetable oil to biodiesel using heterogeneous base catalyst," Catalysis Today 93-95: 315-320 (2004).

Nagata et al., "Synthesis and properties of [2-methyl-2-(oxoalkyl)-1,3-dioxolan-4-yl]methyl methacrylates for photocrosslinking agent", Kobunshi Ronbunshu 42(2): pp. 101-108 (1985); with English Abstract.

Nakamura, et al., "Study on Ketalization Reaction of Poly(vinyl alcohol) by Ketones. VIII. Kinetic Study on Acetalization and Ketalization Reactions of Poly(vinyl alcohol)," Journal of Polymer Sceince: Part A: Polymer Chemistry 34: 3319-3328 (1996).

Ono, et al., "Synthesis and Properties of Soap Types of Double-Chain Cleavable Surfactants Derived from Pyruvate," J. Oleo Sci. 53(2): 89-95 (2004).

Yang, et al., "Synthesis of acetals and ketals catalyzed by tungstosilicic acid supported on active carbon," Journal of Zhejiang University of Science 6B(5): 373-377 (2005).

Zhang, et al., "Qualitative analysis of products formed during the acid catalyzed liquefaction of bagasse in ethylene glycol," Bioresource Technology 98: 1454-1459 (2007).

\* cited by examiner

CARBOXY ESTER KETALS, METHODS OF MANUFACTURE, AND USES THEREOF

CROSS-REFERENCE TO RELATED APPLICATION

This application claims the benefit under 35 U.S.C. 119(e) of U.S. Provisional Application Ser. No. 61/731,194, filed on Nov. 29, 2012, the contents of which are incorporated by reference herein in their entirety.

BACKGROUND

This disclosure relates to carboxy ester ketal compounds and a variety of compositions, including water-borne coating compositions, cleaning compositions, fragrance, and personal care compositions comprising the carboxy ester ketal compounds, methods for the manufacture of the compounds and compositions, and uses of the compositions.

Solvent selection for the foregoing and other uses is guided by considerations such as solubility, reactivity, volatility, toxicity, environmental profile, stability, and cost. While a number of solvents are available and in commercial use, there remains a need in the art for new solvents that offer a favorable combination of these characteristics. There particularly remains a need for renewably-sourced solvents that offer an advantageous combination of one or more attributes such as solubility with one or more components, reactivity, volatility, toxicity, environmental profile, and cost for water-borne coating compositions, cleaning compositions, fragrance, or personal care compositions are continuously sought.

SUMMARY

Provided herein is a compound of formula (1)

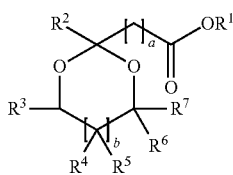

(1)

wherein
$R^1$ is a $C_{7-18}$ alkyl,
$R^2$ is hydrogen or $C_{1-3}$ alkyl,
each $R^3$, $R^4$, $R^5$, $R^6$, and $R^7$ is independently hydrogen or a $C_{1-6}$ alkyl,
a is 2-3, and
b is 0-1.

Also provided herein is a method of making the above-described compound of formula (1), the method comprising contacting a ketoacid ester of formula (2)

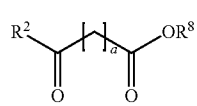

(2)

with a diol of formula (3)

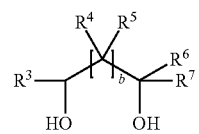

(3)

under reaction conditions effective to form a compound of formula (4)

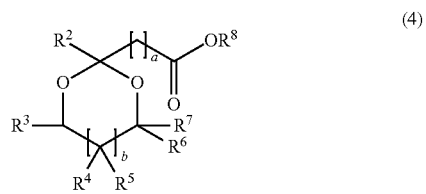

(4)

wherein $R^8$ is a $C_{1-6}$ alkyl group; and transesterifying the $R^8$ group formula (4) with an alcohol of the formula $R^1$—OH to form the compound of formula (1).

Compositions comprising the compound of formula (1) are also described, in particular water-borne coating compositions comprising water; a polymer binder; and the compound of formula (1).

In another embodiment, a latex coating composition comprises water; a latex polymer binder; and the compound of formula (1).

In another embodiment, a water-reducible coating composition comprises water; a water reducible polymer binder; and the compound of formula (1).

In still another aspect, a method of coating a substrate comprises contacting the above-described coating composition with a surface of a substrate to form a coating; and drying the coating.

In another aspect, a coated substrate is made by the above-described method of coating a substrate.

In yet another aspect, a cleaning composition comprises a cleaning or personal care component; and the compound of formula (1).

In still another aspect, a fragrant composition comprises: at least one fragrant composition; and the compound of formula (1).

In another aspect, a cleaning composition comprises a cleaning component; and the compound of formula (1).

The above described and other embodiments are further described in the detailed description that follows.

DETAILED DESCRIPTION

The inventors hereof have discovered long-chain ketal adducts of ketocarboxy esters, in particular levulinate esters. Such carboxy ester ketal adducts offer a combination of properties that make them useful as solvents for a variety of uses. A need remains in the art for renewably-sourced solvents that offer an advantageous combination of one or more attributes such as solubility with one or more components, reactivity, volatility, toxicity, environmental profile, and cost. It would be of further advantage if such solvents could be readily modified to adjust the chemical and physical properties of the solvent to meet the needs of a specific application. It would be advantageous if the renewable-sourced solvents provided a water-borne coating composition, for example, a paint, ink, adhesive, sealant, clear-coat, or caulk composition, a cleaning compositions, a fragrant composition, or a personal care compositions that meets one or more customer needs as applicable to the specific composition.

The ketocarboxy ester ketals, sometimes referred to herein as "ketal adducts," are compounds having the general formula (1):

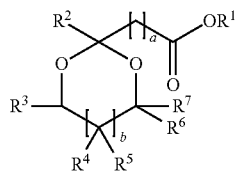

wherein
$R^1$ is a $C_{7-18}$ alkyl,
$R^2$ is hydrogen or a $C_{1-3}$ alkyl,
each $R^3$, $R^4$, $R^5$, $R^6$, and $R^7$ is independently hydrogen or a $C_{1-6}$ alkyl,
a is 2-3, and
b is 0-1.

More specifically, $R^1$ is a $C_{7-18}$ alkyl, $R^2$ is methyl, each $R^3$, $R^4$, and $R^5$ is independently hydrogen or a $C_{1-3}$ alkyl, $R^6$ is hydrogen or a $C_{1-6}$ alkyl, $R^7$ is hydrogen, a is 2-3, and b is 0-1.

Even more specifically $R^1$ is a $C_{7-18}$ alkyl, $R^2$ is methyl, each $R^3$, $R^4$, and $R^5$ is hydrogen, $R^6$ is hydrogen or a $C_{1-3}$ alkyl, $R^7$ is hydrogen, a is 2, and b is 0.

In a specific embodiment $R^1$ is a $C_{7-18}$ alkyl, $R^2$ is methyl, $R^3$ is hydrogen, $R^6$ is hydrogen, methyl, or ethyl, $R^7$ is hydrogen, a is 2, and b is 0.

Preferably, the ketal adduct of formula (1) is the 1,2-propanediol adduct of a levulinic acid ester, having formula (1a):

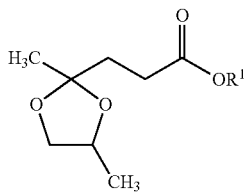

wherein $R^1$ is as defined above, and is specifically a $C_{7-18}$ alkyl, which can be either straight-chain or branched. When $R^1$ is a 2-ethylhexyl group in formula (1a), 2-ethylhexyl levulinate propylene glycol ketal ("2EH-LPK") is obtained. When $R^1$ is a 1-nonyl group in the formula (1a), 1-nonyl levulinate propylene glycol ketal (1N-LPK) is obtained. When $R^1$ is a 3,5,5-trimethylhexyl group in formula (1a), 3,5,5-trimethylhexyl levulinate propylene glycol ketal (355TMH-LPK) is obtained.

The ketal adducts of formula (1) can be obtained by the acid-catalyzed reaction of the corresponding ketoacid ester of formula (2) with a diol of formula (3):

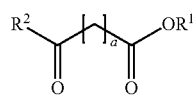

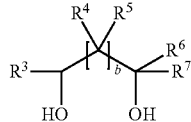

wherein each of $R^1$, $R^2$, $R^3$, $R^4$, $R^5$, $R^6$, and $R^7$, and the integers a and b are as defined above. Reaction conditions are described in WO 09/032,905, for example. Alternatively, ketal adducts of formula (1) can be obtained by transesterification of ketal ester (4) (obtained as described in WO 09/032,905, for example)

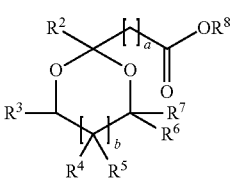

wherein each of $R^2$, $R^3$, $R^4$, $R^5$, $R^6$, and $R^7$ and the integers a and b are as defined above, and $R^8$ is a $C_{1-6}$ alkyl group, for example a methyl or ethyl group. In the transesterification, the ketal (4) is contacted with alcohol $R^1OH$ comprising the desired $R^1$ substituent wherein $R^1$ is as described in formula (1). A catalyst (e.g., a metal oxide or metal complex as described in WO 09/032,905) can be used to accelerate the reaction, in the presence of excess alcohol. Catalysts include, for example those wherein the metal is Sn, Zn, Ge(II), Cu(II), Ni(II), Fe(II), Fe(III), Al(III), Pt(IV), V(IV) or V(V), specifically Sn, Zn, Ni, Al and Pt as oxides or complexes with other ligands such as sulfides or acetates. In an embodiment the metal complex is a dialkyl metal oxide, and the alkyl groups in the dialkyl metal oxide are $C_1$ to $C_{10}$ alkyl groups, alternatively $C_2$ to $C_4$ alkyl groups, alternatively n-butyl groups, for example a tin alkoxide such as dibutyl tin oxide (DBTO). Transesterification can be conducted at elevated temperatures, for example about 160 to about 220° C., with concomitant removal of $R^1OH$.

Many of the compounds falling within the scope of formulas (2) and (3) can be renewably-sourced. The ketal adducts thus provide an entry point for a broad variety of renewably-sourced solvents. For example, levulinic acid is produced by the thermochemical treatment of various carbohydrates such as cellulose; subsequent esterification with renewably-sourced alkanols and ketalization of the levulinate ester with polyhydroxy compounds such glycerol or propylene glycol produces a bioderived solvent.

The ketal adducts are particularly useful in water-borne coating compositions. Water-borne coating compositions encompass a wide variety of coating compositions, including latex and water-reducible coating compositions. Latex resin coatings are water-borne dispersions of sub-micrometer polymer particles. The dispersions are formed by emulsion polymerization, and then can be further formulated for a variety of applications. Latex coating compositions, for example latex paint compositions, can be formulated with a variety of additives, among them a coalescing solvent or "coalescent." Coalescing solvents promote film formation. The coalescing solvent serves as a plasticizer, softening the resin particles by reducing the glass transition temperature (Tg) of the particles, and enabling them to fuse into a continuous film. For example, a latex paint composition containing a coalescing solvent is coated on a substrate and then cures by coalescence, where the water and the coalescing solvent are removed either sequentially or simultaneously. During film formation, the coalescing solvent softens the latex polymer binder particles, fusing them together into an entangled polymer film so that the polymer binder will not redissolve in the water/solvent that originally carried it.

Water-reducible coating compositions are produced using traditional polymerization techniques rather than emulsion polymerization and often contain a water-miscible organic solvent. The polymer binder is usually modified to make it compatible with the water/organic solvent system. The modification can involve a hydrophilic co-monomer, such as an organic acid, that can impart water reducibility to the oligomeric or polymeric binders. Another modification is to disperse the binder in an aqueous phase with the use of a surfactant, which in some cases can be chemically incorporated into the polymer binder during synthesis of the binder. In each case, the resulting polymers are subsequently mechanically dispersed into the aqueous phase. When polymer particles (either liquid or solid) are formed in water, the water-reducible coating composition is an emulsion (for liquid polymers) or a dispersion (for solid polymers). Another version of a water-reducible coating composition is based on the polymer binder being soluble in the organic solvent/water mixture or partially soluble in the organic solvent/water mixture because the polymer chains form aggregates that are dispersed in the liquid aqueous phase. The solvent partitions between the polymer aggregates and the water. Thermosetting acrylics, epoxies, polyesters, epoxy-esters, and alkyds are examples of binders used in water-reducible coating compositions.

While all water-borne coating compositions contain a polymer binder and water, the different properties of the binders result in different formulation requirements. As mentioned above, water-reducible compositions are often initially dissolved in a non-aqueous solvent to reduce viscosity and aid the dispersion in water. The compositions can further be formulated with a variety of additives, among them a coalescing solvent to promote film formation. The coalescing solvent softens the polymer binder particles by reducing the glass transition temperature (Tg) of the particles to below the processing temperature, and enabling them to fuse into a continuous film. Thus, when a water-reducible coating composition containing a coalescing solvent is coated onto a substrate, the coating cures by coalescence, where the water and the coalescing solvent evaporate sequentially or simultaneously. During solvent or water evaporation, the concentration of dispersed latex particles or microemulsion droplets increases to the point where particles or microemulsion droplets come in contact the coalescing solvent draws together and the coalescent softens the polymer binder particles, allowing the particles to fuse together into an entangled polymer network film. In some cases, the coalescent does not evaporate and can serve as a plasticizer for the final film. Chemical curing, through a crosslinking agent or an oxidative process, can occur after the film is substantially cured through the solvent evaporation mechanism.

A need remains for solvents, preferably renewably-soured solvents, that can be used in a water-borne coating composition, for example, a paint, ink, adhesive, sealant, clear-coat, or caulk composition that meets one or more customer needs as applicable to the specific coating composition such as hydrolytic stability, good viscosity, balanced dry time, or good flow and leveling in the coating composition; or good adhesion of a dry film, good scrub resistance, durability, impact resistance, flexibility, water resistance, chemical resistance, stain resistance, gloss, or hardness in the resultant coating. It would be of additional advantage if the renewably-sourced solvents provided a water-borne coating composition with low minimum film forming temperature and low volatile organic compound content with appreciable storage stability.

It has been found that the ketal adducts (1), specifically (1a), find use in water-borne coating compositions. Without being bound by theory, it is believed that the ketal adducts function primarily as a coalescing solvent during the formation of films. However, it is to be understood that the ketal adducts can have more than one function, including one or more of solubilization, solvent coupling, VOC content reduction, reduction of film forming temperature, plasticization, and the like. In an advantageous feature, selection of the specific $R^1$, $R^2$, $R^3$, $R^4$, $R^5$, $R^6$, and $R^7$ groups, and a and b in the ketal adducts of formula (1) allows the chemical and physical properties of the ketal adducts to be adjusted to achieve the desired combination of properties, for example, hydrolytic stability and VOC reduction.

In a specific embodiment the groups $R^1$, $R^2$, $R^3$, $R^4$, $R^5$, $R^6$, and $R^7$ groups, and integers a and b are selected to provide a desired coalescing activity, that is, the ability of the ketal adduct to plasticize the polymer binder and aid in film formation of a coating. Where needed, the presence of ester and ether functionality allows interaction of the ketal adduct with a different types of polymer binder functional groups.

The ketal adducts (1), specifically (1a), are further advantageous in that the structure of the compounds can be adjusted to alter the volatility of the compounds. Volatility manifests itself in a number of key properties for coalescing solvents, including boiling point, vapor pressure, relative evaporation rate, flammability, odor, and volatile organic compound (VOC) content. The desired volatility profile of a solvent varies considerably by application, and there are often conflicting considerations. For instance, highly volatile solvents require less energy to remove after use, but in many cases also require special handling due to higher flammability. Appropriate selection of $R^1$, $R^2$, $R^3$, $R^4$, $R^5$, $R^6$, and $R^7$ groups, and integers a and b can further provide a selected volatility. In particular, 2EH-LPK, 1N-LPK, and 355TMH-LPK are of acceptably low volatility and low flammability (e.g., have a flash point of about 99° C. (210° F.) or higher) and have high coalescing efficiency while decreasing VOC concentrations in the coating formulations to a level below about 5.0 to about 10 g of VOC per liter of the coating composition.

The water-borne coating compositions comprise water; a polymer binder; and ketal adduct (1). The coating compositions can be formulated (i.e., the type and amount of polymer binder, water, other cosolvents if present, and additives) as a paint, adhesive, sealant, stain, clear coat, caulk, or ink composition. Advantageously, the water-borne compositions can maintain a pH for more than about 1 week, specifically more than about 2 weeks, and more specifically more than about 4 weeks within a range of about 7.5 to about 10, or about 7.5 to about 9.0 or about 8.5 to about 9.5 or about 8.5 to about 9.5. In another embodiment, the water-borne compositions can maintain a stable initial pH that is in the range of about 7.5 to about 10, or about 7.5 to about 9.0, or about 8.5 to about 9.5, specifically about 9.0, for more than about 1 week, specifically more than about 2 weeks, and more specifically more than about 4 weeks. For example, the initial pH of the water-borne compositions, for example the latex paint compositions comprising a ketal (1), specifically adduct (1a), varies less than 0.5 pH units at 23° C., specifically less than 0.2 pH units at 23° C. pH, over about 1 week, over about 2 weeks, or over about four weeks, or even more.

In an embodiment, the water-borne coating composition is a latex coating composition comprising a latex polymer binder, water, and a ketal adduct (1), specifically (1a).

The polymer binder of the latex can be selected from a wide variety of polymers as known in the art of latex coating compositions, specifically latex paint compositions, latex adhesive compositions, latex sealant compositions, latex caulk compositions, latex stain compositions, and latex ink compositions. For instance, the latex polymer binder can be derived from monomers comprising vinyl acetate or at least one acrylic monomer such as acrylic acid, acrylic acid $C_{1-10}$ alkyl esters, methacrylic acid, or methacrylic acid $C_{1-10}$ alkyl esters, optionally copolymerized with one or more of styrene, hydroxyethyl acrylate, hydroxypropyl acrylate, α-methyl styrene, vinyl chloride, acrylonitrile, methacrylonitrile, ureido methacrylate, vinyl acetate, vinyl esters of branched tertiary monocarboxylic acids (e.g., vinyl esters of versatic acid (referred to as vinyl versatates) commercially available under the trademark VeoVa® from Shell Chemical Company or sold as Exxar® Neo Vinyl Esters by ExxonMobil Chemical Company), itaconic acid, crotonic acid, maleic acid, fumaric acid, and ethylene. It is also possible to include C4-8 conjugated dienes such as 1,3-butadiene, isoprene, and chloroprene. In an embodiment, the monomers include one or more of n-butyl acrylate, methyl methacrylate, styrene, and 2-ethylhexyl acrylate.

Pure acrylics can be used (comprising acrylic acid, methacrylic acid, an acrylate ester, and/or a methacrylate ester as the main monomers); styrene-acrylics (comprising styrene and acrylic acid, methacrylic acid, an acrylate ester, and/or a methacrylate ester as the main monomers); vinyl-acrylics (comprising vinyl acetate and acrylic acid, methacrylic acid, an acrylate ester, and/or a methacrylate ester as the main monomers); and acrylated ethylene vinyl acetate copolymers (comprising ethylene, vinyl acetate and acrylic acid, methacrylic acid, an acrylate ester, and/or a methacrylate ester as the main monomers). The monomers can also include other main monomers such as acrylamide and acrylonitrile, optionally with one or more monomers such as itaconic acid and ureido methacrylate.

The latex polymer binder is present in water in the form of an aqueous dispersion, and can include about 2 to about 85 weight percent (wt. %) solids, specifically about 5 to about 75 wt. % solids (i.e., the weight percentage of the dry latex polymer based on the total weight of the aqueous latex coating composition). The latex can be present in a wide variety of particle sizes, for example a mean latex particle size from about 10 to about 1,000 nanometers (nm), specifically about 50 to about 800 nm. The particle size distribution can be mono-modal or multimodal, for example bimodal. The ketal adduct (1), specifically (1a), is present in the latex coating composition in an amount effective for its purpose, i.e., coalescence of a film, solubilization, and the like. Such amounts can be determined by one of ordinary skill in the art, and can be for example, from about 0.1 to about 30 wt. %, specifically about 1 to about 20 wt. %, based on the total weight of the dry weight of the latex polymer binder. The balance of the latex coating compositions is water and other optional additives known in the art.

In a specific embodiment, the ketal adducts (1), specifically (1a), are used in latex paint compositions, and can reduce or replace other organic solvents in the latex paint compositions. In particular, 2EH-LPK can be used as a green coalescing solvent in latex paint compositions, and in particular paints used in architectural and light industrial applications. Thus, in an embodiment, a latex paint composition comprises a latex polymer binder, water, a ketal adduct (1), specifically (1a), and a pigment. The paint compositions can be a primer, base cocate, top coat, color coat.

In an alternative embodiment, the ketal adducts (1), specifically (1a), are used in latex stain compositions, latex adhesive compositions, latex sealant compositions, latex caulk compositions, latex mastic compositions, or latex ink compositions. Thus, in another embodiment, a latex coating composition comprises at least one latex polymer binder, water, a ketal adduct (1), specifically (1a), and optionally a pigment, wherein the latex coating composition is a latex adhesive composition, latex sealant composition, latex caulk composition, latex stain composition, latex mastic compositions, or latex ink composition, and the latex polymer binder is selected with regard to the particular function of the latex coating composition.

A wide variety of latex polymer binders can be used in the foregoing latex coating compositions, including those described for the latex paint compositions. Acrylics can be specifically mentioned, formed from one or more of acrylic acid, methacrylic acid, a $C_{1-10}$ alkyl acrylate ester, a $C_{1-10}$ alkyl methacrylate ester, or vinyl versatate monomers. Styrene-acrylics formed from styrene and at least one of acrylic acid, methacrylic acid, a $C_{1-10}$ alkyl acrylate ester, or a $C_{1-10}$ alkyl methacrylate ester monomers can be used. Other latexes include vinyl-acrylics formed from vinyl acetate and at least one of acrylic acid, methacrylic acid, a $C_{1-10}$ alkyl acrylate ester, or a $C_{1-10}$ alkyl methacrylate ester monomer. Acrylated ethylene-vinyl acetate copolymers can be used and be formed, for example from ethylene, vinyl acetate, and at least one of acrylic acid, a $C_{1-10}$ alkyl acrylate ester, or a $C_{1-10}$ alkyl methacrylate ester monomer. The foregoing polymers can also include other monomers such as acrylamide, acrylonitrile, itaconic acid, and ureido methacrylate.

A pigment can be present in the latex coating compositions. The term "pigment" as used herein includes non-film-forming solids such as extenders and fillers, for example an inorganic pigment $TiO_2$ (in either anatase and rutile forms), clay (aluminum silicate), $CaCO_3$ (in both ground and precipitated forms), aluminum oxide, silicon dioxide, magnesium oxide, talc (magnesium silicate), barites (barium sulfate), zinc oxide, zinc sulfite, sodium oxide, potassium oxide, solid (high Tg) organic latex particles added to modify hardness or surface roughness or (as in the case of hollow latex particles) to replace $TiO_2$, and a combination comprising at least one of the foregoing. Representative combinations include blends of metal oxides such as those sold under the marks MINEX® (oxides of silicon, aluminum, sodium and potassium commercially available from Unimin Specialty Minerals), CELITES® (aluminum oxide and silicon dioxide commercially available from Celite Company), ATOMITES® (commercially available from Imerys), and ATTAGELS® (commercially available from BASF). Specifically, the pigment includes $TiO_2$, $CaCO_3$, or clay.

Generally, the mean particle sizes of the pigments are about 0.01 to about 50 micrometers. For example, the $TiO_2$ particles used in the aqueous coating composition typically have a mean particle size from about 0.15 to about 0.40 micrometers. The pigment can be added to the aqueous coating composition as a powder or in slurry form.

The latex coating compositions can contain additional additives, as known in the art, to modify the characteristics of the latex coating compositions and provided the desired functionality, provided that the additives do not significantly adversely affect the desired properties of the composition. These additives can include a plasticizer, drying retarder, dispersant, surfactant or wetting agent, rheology modifier, defoamer, thickener, biocide, mildewcide, colorant, wax, perfume, pH adjuster, or co-solvent. The additives are present in the amount ordinarily used in latex coating compositions, and particularly in latex paint compositions, latex adhesive compositions, latex sealant compositions, latex caulk compositions, latex mastic compositions, and latex ink compositions. In an embodiment, the latex coating composition consists essentially of a latex polymer binder, water, an optional pigment, and a ketal adduct (1), specifically (1a). As used herein, the phrase "consists essentially of" encompasses the latex polymer binder, water, optional pigment, and ketal adduct, and optionally one or more of the additives defined herein, but excluding any additive that significantly adversely affects the desired properties of the latex coating composition or the dried coating derived therefrom.

The latex polymer binder can be present in the latex composition in a dry weight amount from about 5 to about 80 wt. %, and more specifically about 8 to about 60 wt. % of the latex coating composition, based on the total weight of the latex coating composition.

When present, a pigment can be used in the latex coating composition in an amount from about 5 to about 75 wt. %, specifically about 10 to about 55 wt. % of the total solids in the latex composition.

The ketal adduct (1), specifically 1(a), can be present in the latex coating composition in an amount from about 0.1 to about 30 wt. %, about 0.5 to about 20 wt. %, about 1 to about 15 wt. %, about 1 to about 10 wt. %, about 1 to about 8 wt. %, and more specifically about 1 to about 7 wt. %, based on the dry weight of the polymer binder.

Although much of the water is present in the latex dispersion and in other components of the latex composition, water can be added separately to the latex composition. Typically, the latex composition includes about 10 to about 85 wt. % and more specifically about 20 to about 80 wt. % water, i.e., the total solids content of the latex composition is about 15 to about 90 wt. %, more specifically about 20 to about 80 wt. % of the total composition. The compositions are typically formulated such that the hardened (dried) coatings comprise at least about 5 volume % (vol. %) dry polymer solids, and, when present, about 5 to about 90 vol. % of non-polymeric solids in the form of pigments. In addition to the dry polymer solids and non-polymeric solids in the form of pigments, the hardened (dried) coatings may comprise an amount of the ketal adduct (1), specifically (1a), in an amount of about 35 vol. % upon drying, and this amount decreases to essentially zero over time.

In another embodiment, a latex caulking composition comprises a latex polymer binder, water, a ketal adduct (1), specifically (1a), and a caulking additive, for example fillers, such as talc and calcium carbonate, mildewcides, biocides, pigments and plasticizers. The polymer binder of the caulking composition can be selected from a wide variety of polymers as known in the art of latex coating compositions, for example those described above for latex paint compositions. Additives include fillers, such as talc and calcium carbonate, mildewcides, biocides, antifoam agents, antifreeze agents, pigments and plasticizers. The amounts of the latex polymer binder and the ketal adduct (1), specifically 1(a) effective to form a latex caulking composition can be determined by one of ordinary skill in the art, and can be, for example, about 5 to about 80 wt. % of the polymer binder solids, based on the total weight of the latex caulking composition, and about 0.1 to about 30% of the ketal adduct, more specifically between about 0.1 and about 10% (1), specifically 1(a), based on the total weight of the latex caulking composition.

In another embodiment, a latex sealant, mastic, or adhesive composition comprises a latex polymer binder, water, a ketal adduct (1), specifically (1a), and a sealant or adhesive additive, for example a pigment. The polymer binder of the sealant or adhesive can be selected from a wide variety of polymers as known in the art of latex coating compositions, for example those described above for latex paint compositions. Additives include fillers, such as talc and calcium carbonate, mildewcides, biocides, pigments, antifoam agents, antifreeze agents, tackifiers, and plasticizers. The amounts of the latex polymer binder and the ketal adduct (1), specifically 1(a) effective to form a latex sealing or adhesive composition can be determined by one of ordinary skill in the art, and can be, for example, about 5 to about 80 wt. % of the polymer binder solids, based on the dry weight of the caulking composition, and about 0.1 to about 30%, specifically about 0.1 to about 10% and more specifically about 0.1 to about 5% of the ketal adduct (1), specifically 1(a), based on the total weight of the sealant, mastic, or adhesive composition.

In another embodiment, a latex ink composition comprises a latex polymer binder, water, a ketal adduct (1), specifically (1a), a pigment and optionally an ink additive, for example a wax. The polymer binder of the latex can be selected from a wide variety of polymers as known in the art of latex ink compositions, for example those described above for latex paint compositions. Additives include waxes, dyes, antifoam agents, antifreeze agents, surfactants, and plasticizers. The amounts of the latex polymer binder and the ketal adduct (1), specifically 1(a) effective to form a latex ink composition can be determined by one of ordinary skill in the art, and can be, for example, about 5 to about 80 wt. % of the polymer binder solids, based on the dry weight of the ink composition, and about 0.1 to about 30% of the ketal adduct (1), specifically 1(a), based on the total weight of the latex ink compositions.

In another embodiment, a water-reducible coating composition comprise a water-reducible polymer binder, water, and the ketal adduct represented by formula (1), specifically (1a). The water-reducible polymer binder can be selected from a wide variety of polymers known in the art of water-reducible coating compositions, specifically water-reducible paint compositions, and can include, for example, acrylics that are produced using traditional polymerization techniques in a water-miscible organic solvent, polyesters, polyurethanes, alkyds, silicone-modified alkyds, epoxies, epoxy esters, and alkyds. In specific embodiment, the binder is a polyurethane, for example an aliphatic polyurethane, an alkyd, an acrylic, or combinations or hybrids thereof. The water-reducible polymer binder can be present in the water composition as a true solution (i.e. the volume of the solution is equal to the sum volume of the water-reducible polymer binder and water), an emulsion, a duplex emulsion (e.g., a water-in-oil-in water emulsion (W/O/W)), a dispersion, or a suspension (i.e. coarse dispersion). The various types of polymer binders can be made water-reducible by neutralizing residual free acid groups attached to the polymer backbone with a base, for example an organic amine, ammonium hydroxide, or other base. Exemplary acrylic binders or alkyds can have acid numbers of about 20 to about 100.

The polymer binder can be thermosetting, in which case any curing agent utilized for each polymer binder will depend on the nature of the particular polymer and its curing mechanism. Thus, for the polyester and alkyd polymers having hydroxyl, carboxyl or amide functionality or any combination of such functionalities, cross-linking or curing can be effected by means of urea formaldehyde, melamine formaldehyde and methoxylated, ethoxylated or butoxylated forms thereof. Blocked isocyanate crosslinking agents are also known in the art. Catalysts can also be used to promote the curing reaction, such as peroxides. In addition to catalysts, promoters and activators for promoting the curing reaction can be used.

Some polymer binders, e.g., curable polyurethane binders, include two components: an aqueous component including an active hydrogen-containing component (i.e., a polyol or amino-functional compound) in one part and an aqueous polyisocyanate in another part. The polyol can be a soluble or water-dispersible polyol, optionally having a carboxyl group, or a hydroxy- and/or amino-functional oligourethane, and the polyisocyanate can be modified with polyoxyalkylene ether alcohol to be water-soluble or water dispersible.

Epoxy binders include derivatives of diglycidyl ether/bisphenol compounds such as bisphenol A (DGEBA), i.e., derivatives of polyether diepoxides that are obtained from the polymeric adduction of bisphenols with the diglycidyl ether of the bisphenol. The epoxies can be rendered water-soluble by reacting them with phosphoric acid and then neutralizing the resulting, acidic, ester, and glycol-comprising reaction products with a base. If the base is a fugitive base, such as ammonia or a volatile amine, the water-thinned, neutralized polymer can be converted to a water-insensitive, high performance thermoset polymer binder by evaporating the water, heating to disrupt the ammonium salt groups and drive off the ammonia (or amine), and curing. Conventional curing agents capable of reacting with acidic and/or alcoholic hydroxyl groups may be incorporated with the uncured polymer. Epoxy binders can also be made with a surfactant to aid in dispersion. In some cases, the surfactant can have reactive groups so that the surfactant is chemically incorporated into the polymer system.

As indicated above, the water-reducible polymer binder can be present in water completely dissolved, i.e., in the form of a solution, in the form of aggregates, or an aqueous dispersion, and can include about 5 to about 85 wt. % solids, specifically about 10 to about 75 wt. % solids (i.e., the weight percentage of the polymer binder based on the total weight of the water-reducible coating composition). It is noted that the higher the concentration of the dispersed phase, the higher will the viscosity be. As used herein, "solids" refers to the 100% binder in whatever form, such as a solid or liquid. The polymer binder can be present in a wide variety of particle sizes, for example a mean polymer binder particle size from about 10 to about 1,000 nanometers (nm), specifically about 50 to about 800 nm. The particle size distribution can be mono-modal or multimodal, for example bimodal.

The ketal adduct (1), specifically (1a), is present in the water-reducible coating composition in an amount effective for its purpose, i.e., coalescence of a film, solubilization, and the like. Such amounts can be determined by one of ordinary skill in the art, and can be for example, from about 0.1 to about 30 wt. %, or about 0.5 to about 30 wt. %, specifically about 1 to about 20 wt. % or about 1 to about 10 wt. %, each based on the total weight of the water-reducible coating compositions. The balance of the water-reducible coating compositions is water, polymer binder, and other optional additives, including cosolvents known in the art.

In a specific embodiment, the ketal adducts (1), specifically (1a), are used in water-reducible paint compositions, stain composition, or clear-coat compositions, and can reduce or replace other organic solvents in the water-reducible compositions. EtLPK in particular can be used as a green/non-toxic coalescing solvent in water-reducible paint, stain, or clear-coat compositions, and in particular such compositions used in architectural and light industrial applications. Because EtLPK evaporates more slowly than water, drying time is slower. However, the volatility of EtLPK is such that none or very little remains in the fully dried film, thereby avoiding a tacky film.

Thus, in an embodiment, a water-reducible paint, stain, or clear-coat composition comprises a water-reducible polymer binder composition, water, optionally a pigment, and a ketal adduct (1), specifically (1a). A wide variety of water-reducible polymer binders can be used, including those described above. When the polymer binder is thermosetting, the binder compositions comprise the uncured polymer and one or more of a curing agent, catalyst, initiator, or promoter, if used.

A pigment can be present in the water-reducible paint or stain composition. The term "pigment" as used herein includes non-film-forming solids such as extenders and fillers, for example an inorganic pigment aluminum oxide, barites (barium sulfate), $CaCO_3$ (in both ground and precipitated forms), clay (aluminum silicate), chromium oxide, cobalt oxide, iron oxides, magnesium oxide, potassium oxide, silicon dioxide, talc (magnesium silicate), $TiO_2$ (in both anastase and rutile forms), zinc oxide, zinc sulfite, an organic pigment such as solid (high Tg) organic latex particles added to modify hardness or (as in the case of hollow latex particles) to replace $TiO_2$, carbon black, and a combination comprising at least one of the foregoing. Representative combinations include blends of metal oxides such as those sold under the marks Minex® (oxides of silicon, aluminum, sodium and potassium commercially available from Unimin Specialty Minerals), Celite® (aluminum oxide and silicon dioxide commercially available from Celite Company), Atomites® (commercially available from English China Clay International), and Attagels® (commercially available from Engelhard). Specifically, the pigment includes $TiO_2$, $CaCO_3$, or clay.

Generally, the mean particle sizes of the pigments are about 0.01 to about 50 micrometers. For example, the $TiO_2$ particles used in the aqueous coating composition typically have a mean particle size from about 0.15 to about 0.40 micrometers. The pigment can be added to the aqueous coating composition as a powder or in slurry form.

A dye can be present in the water-reducible paint or stain composition, in addition to or instead of a pigment. The term "dye" as used herein includes organic compounds generally soluble in the compositions, and that impart color to the compositions.

The water-reducible paint, stain, or clear-coat composition can contain additional additives, as known in the art, to modify the characteristics of the water-reducible composition, provided that the additives do not significantly adversely affect the desired properties of the paint, stain, or clear-coat, for example, viscosity, drying time, or other characteristic. These additives can include a plasticizer, drying retarder, dispersant, surfactant or wetting agent, rheology modifier, defoamer, thickener, biocide, mildewcide, colorant, wax, perfume, pH adjuster, or cosolvent. The additives are present in the amount ordinarily used in water-reducible paint, stain, or clear-coat compositions. In an embodiment, the water-reducible paint, stain, or clear-coat composition consists essentially of a water-reducible polymer binder, water, an optional pigment, an optional dye, and a ketal adduct (1), specifically (1a). As used herein, the phrase "consists essentially of" encompasses the water-reducible polymer binder, water, optional pigment, and ketal adduct, and optionally one or more of the additives defined herein, but excludes any additive that significantly adversely affects the desired properties of the water-reducible composition or the dried coating derived therefrom.

The water-reducible polymer binder can be present in the water-reducible paint composition in an amount from about 2 to about 60 wt. %, and more specifically about 4 to about 40 wt. % of the water-reducible paint composition, based on the dry weight of the polymer water-reducible binder.

When present, the pigment can be used in the water-reducible paint composition in an amount from about 2 to about 50 wt. %, specifically about 5 to about 40 wt. % of the total solids in the water-reducible paint composition.

The water-reducible polymer binder can be present in the water-reducible stain composition in an amount from about 0.1 to about 50 wt. %, and more specifically about 0.5 to about 30 wt. % of the water-reducible stain composition, based on the dry weight of the polymer water-reducible binder.

When present, the pigment or dye can be used in the water-reducible stain composition in an amount from about 0.1 to about 40 wt. %, specifically about 0.5 to about 30 wt. % of the total solids in the water-reducible stain composition.

When present, the dye can be used in the water-reducible paint or stain composition in an amount from 0.001 to about 10 wt. %, specifically 0.005 to about 5 wt. % of the total solids in the water-reducible paint or stain composition.

The ketal adduct (1), specifically 1(a), more specifically 1(b), can be present in an amount from about 0.1 to about 30 wt. %, specifically about 1 to about 10 wt. %, more specifically about 1 to about 8 wt. %, and still more specifically about 1 to about 7 wt. %, based on the dry weight of the polymer binder.

The water-reducible paint composition can include about 5 to about 85 wt. % and more specifically about 35 to about 80 wt. % water, i.e., the total solids content of the water-reducible paint composition can be about 15 to about 95 wt. %, more specifically, about 20 to about 65 wt. % of the total composition. The compositions can be formulated such that the hardened (dried) coatings comprise at least about 2 to about 98 volume % (vol. %) polymer solids and, if present, the ketal adduct (1), specifically (1a), and about 2 to about 98 vol. % of non-polymeric solids in the form of pigments or a combination of a pigment and a dye, together with other additives (if present).

The water-reducible stain composition can includes about 10 to about 95 wt. % and more specifically about 25 to about 90 wt. % water, i.e., the total solids content of the water-reducible stain composition can be about 5 to about 75 wt. %, more specifically, about 10 to about 75 wt. % of the total composition. The stain compositions are typically formulated such that the hardened (dried) coatings comprise at least about 1 vol. %, for example about 5 to about 98 vol. % polymer solids, if present, the ketal adduct (1), specifically (1a), and about 0.1 to about 99 vol. % of non-polymeric solids in the form of pigments and/or dyes, and other additives (if present). A wood stain coating can penetrate the wood substrate to some degree.

The water-reducible clear-coating composition can include about 10 to about 95 wt. % and more specifically about 25 to about 90 wt. % water, i.e., the total solids content of the water-reducible clear-coating composition can be about 5 to about 75 wt. %, more specifically, about 10 to about 75 wt. % of the total composition. The compositions are typically formulated such that the hardened (dried) clear-coatings comprise at least about 1 vol. % polymer solids, for example about 1 to about 100 vol. % polymer solids, if present, the ketal adduct (1), specifically (1a), and 0 to about 10 vol. % of non-polymeric solids. For example, in clear-coat compositions certain additives (e.g., calcium carbonate, talc, or silica) can be used that do not impart color, but rather serve primarily to reduce formulation cost, modify gloss levels, or the like.

A method of preparing any of the foregoing water-borne coating compositions comprises combining water, the polymer binder, the ketal adduct (1), specifically (1a), and any optional additives, for example a pigment to form the water-borne coating compositions. The components can be combined in any suitable order.

For example, a method of preparing a latex coating composition comprises combining the aqueous emulsion of the latex polymer binder, the ketal adducts (1), specifically (1a), and any optional additives, for example a pigment to form a latex coating composition. The ketal adducts and additives can be added in any suitable order to the polymer latex, the additives, or combinations thereof, to provide these additives in the aqueous coating composition. In the case of latex paint compositions, the aqueous coating composition has a pH from about 7 to about 10. Alternatively, the ketal adducts (1), specifically (1a), can be present during polymerization of the latex polymer binder. A method of preparing a latex paint composition comprises combining the aqueous dispersion of the latex polymer binder, the ketal adducts (1), specifically (1a), the pigment, and any optional additives to form the latex paint composition.

In another embodiment, a method of preparing a water-reducible coating or paint, stain, or clear-coating composition comprises combining the polymer binder, the ketal adducts (1), such as, for example (1a), aqueous phase (i.e., water and any cosolvents if present), and any additives, if present, to form a water-reducible coating composition. The components can be added in any suitable order to provide the water-reducible coating composition. The polymer binder can be combined with the ketal adduct after synthesis of the polymer binder is complete. Thus, the ketal adduct can be added to the polymer binder or water before the binder is combined with the water to form the coating composition. Addition of the ketal adduct to the polymer binder prior to adding the combination to water can improve processing due to a decrease in the viscosity of the polymer/ketal combination. Alternatively, the ketal adduct can be admixed after the binder is combined with the water. Where the binder is neutralized, the ketal adduct can be combined with the binder before neutralization or after neutralization. For example, the ketal adduct and polymer binder can be combined after the binder is neutralized, to prevent side reaction of the ketal adduct and the base used for neutralization. In the case of water-reducible paint compositions, the aqueous coating composition has a pH from about 5 to about 8.5.

In another embodiment, the components of the water-reducible coating composition, e.g., a paint, stain, or clear-coat composition, are provided in two parts that are combined immediately prior to use. For example, a first part of an epoxy water-reducible coating composition includes an epoxy dispersion and a second part includes an amine crosslinker. The parts are mixed in a predetermined ratio to provide the epoxy system. The ketal esters and other additives are generally present in the epoxy dispersion. Similarly, a first part of a water-reducible alkyd composition includes an alkyd binder, and a second part includes a melamine crosslinker. A first part of polyurethane water-reducible coating composition includes hydroxyl functional polyurethane dispersion and a second part includes an isocyanate prepolymer. The parts are mixed in a predetermined ratio to provide the polyurethane system. The ketal esters and other additives are generally present in the polyurethane dispersion.

A method of use, that is, coating a substrate with the water-borne coating composition is also described. The substrate can be a wide variety of materials such as paper, wood, concrete, metal, glass, ceramics, plastics, plaster, roofing substrates such as asphaltic coatings, roofing felts, foamed polyurethane insulation, polymer roof membranes, and masonry substrates such as brick, cinderblock, and cementitious layers, including exterior building cladding systems such as EIFS (Exterior Insulating Finishing Systems). The substrates include previously painted, primed, undercoated, worn, or weathered substrates. The method comprises contacting a surface of the substrate with the water-borne coating composition to form a film and drying the film to harden the film. The water-borne coating composition can be applied to the materials by a variety of techniques well known in the art such as curtain coating, sponge, brush, rollers, mops, air-assisted or airless spray, electrostatic spray, and the like. In an embodiment, the paint composition does not substantially penetrate or impregnate the substrate. In another embodiment, the clear-coat composition does not substantially penetrate or impregnate the substrate. Stains are generally designed to partially or fully impregnate the substrate upon coating. In embodiment, the substrate is fully impregnated by the stain composition, such that the film formed conforms to the interior of the coated substrate, and may be continuous or discontinuous.

Hardening occurs through water and solvent loss, either by evaporation under atmospheric conditions at room temperature or with heat to aid the drying rate. Curing may be carried out before drying, during drying, or after drying, or any combination thereof. Chemical curing, through a crosslinking agent or an oxidative process, can occur after the film is substantially cured through the solvent evaporation mechanism.

According to another embodiment, a substrate coated with a dried coating is provided, wherein the dried coating comprises the polymer binder in the form of a film. Some amount of a ketal adduct (1), specifically (1a) may be present. In an embodiment, the ketal adduct can be chemically combined with the polymer binder. For example, ketal adducts (1), specifically (1a), can be present in the coating in an amount from about 1 part per million by weight (ppm) to about 15 wt. %, specifically about 0.1 to about 15 wt. %, each based on the total weight of the dried coating. For example, where the ketal adduct performs a plasticizing function, the adduct can be present in higher amounts, for example about 0.25 to about 15 wt. %, based on the total weight of the dried coating.

The dried coating is disposed on a surface of the substrate, in the form of a film that can partially or completely cover the surface. The coating can be disposed directly on the surface, or one or more intermediate layers (e.g., a primer) can be present between the coating and the surface of the substrate. In a further embodiment, the dried coating can be a dried paint coating that comprises the polymer binder in the form of a film. The dried paint coating further contains one or more additional additives as discussed above, for example a pigment. The dried coating or dried paint coating can be substantially free of one or more of water, another coalescing agent, or other organic solvent. In addition, or alternatively, as described above, the coating can be partially or fully impregnated into the substrate and conform to interior surfaces of the substrate. In these embodiments, ketal adducts (1), specifically (1a) can be present in the in the coating in an amount from about 1 part per million by weight to about 15 wt. %, specifically about 0.1 to about 15 wt. %, each based on the total weight of the dried coating. Again, where the ketal adduct performs a plasticizing function, the adduct can be present in higher amounts, for example about 0.25 to about 15 wt. %, based on the total weight of the dried coating. In any of the foregoing embodiments, it is also possible to dry the coating and/or substrate sufficiently to remove ketal adducts (1), specifically (1a) to below detectable limits in the films.

The water-borne coating composition exhibits comparable or improved coalescence compared to otherwise similar compositions that do not have the ketal adducts (1), specifically (1a).

The water-borne coating composition has a low minimum film forming temperature (MFFT). Particularly, the ketal adducts of formula 1, specifically formula (1a), lowers the minimum film forming temperature to below about 10° C. (50° F.), specifically, to below about 5° C. (41° F.) as measured using ASTM Method D2354. The minimum film forming temperature is an indicator of coalescing efficiency. The minimum film forming temperature is the minimum temperature at which a water-borne synthetic latex will coalesce when applied to a substrate as a thin film. At a temperature less than the minimum film forming temperature, a powdery, cracked layer will result instead of a film.

Further, the water-borne coating composition provides a coating of commercially acceptable properties while substantially reducing or eliminating the need for VOCs within the coating composition. The water-borne coating composition, in particular the latex paint composition, advantageously comprises less than about 250 g/l of VOCs, and more advantageously comprises no substantial content of VOCs. Thus, latex paint composition can be produced that possess lower VOC levels than conventional latex paint compositions and that are more environmentally desirable than conventional coatings. In an embodiment, the water-borne coating composition, in particular the latex paint composition has a VOC content of less than about 150 g/l, less than about 100 g/l, less than about 50 g/l, or even substantially zero, i.e., less than about 10 g/l, as determined using ASTM Method D3960 Alternatively, a component of a composition can be defined as being a VOC if its initial boiling point is less than or equal to about 250° C. measured at a standard pressure of 101.3 kPa per EU Directive 2004/442/CE. The VOC content of a coating composition is the mass of VOC compounds, expressed in g/l, in the composition in its ready to use condition and can be measured by ISO 11890-2.

While ASTM Method D3960 is applicable for determining the VOC content expressed as the mass of VOC per unit volume of coating, ASTM Method D2369 is used to obtain a weight percent of nonvolatile matter by difference for determining the volatiles emitted by coatings. In an embodiment, the ketal adduct of formula (1a) used in the latex paint composition retains greater than about 50 wt. %, specifically greater than about 55 wt. %, and more specifically greater than about 60 wt. % of the ketal adduct based on an initial amount of the ketal adduct as determined by ASTM Method D2369. This indicates that a water-borne composition comprising a ketal adduct of formula (1a) as the coalescing solvent has extremely low VOC content contribution due to the coalescing solvent Moreover, the water-borne composition, for example paint compositions such as the latex paint composition, has improved hydrolytic stability. Water-borne compositions, for example paint compositions typically are stored at a relatively high alkaline pH, for example at a pH of about 7.5 to about 10. In highly alkaline environments, ester hydrolysis can occur at a significant rate, and the coalescing efficiency of an ester-functionalized coalescing solvent decreases. Without being bound by theory, it is believed that ester hydrolysis produces carboxylic acids that decrease the pH of the paint compositions, particularly latex paint compositions. In an embodiment, the water-borne compositions, for example the latex paint compositions comprising a ketal (1), specifically adduct (1a), can maintain a pH for more than about 1 week, specifically more than about 2 weeks, and more specifically more than about 4 weeks within a range of about 7.5 to about 10, or about 7.5 to about 9.0 or about 8.5 to about 9.5 or about 8.5 to about 9.5 at a temperature of 10° C. to 25° C. In another embodiment, water-borne compositions, for example paint compositions such as latex paint compositions comprising a ketal (1), specifically adduct (1a), can maintain a stable initial pH that is in the range of about 7.5 to about 10, or about 7.5 to about 9.0, or about 8.5 to about 9.5, specifically about 9.0, for more than about 1 week, specifically more than about 2 weeks, and more specifically more than about 4 weeks at a temperature of 10° C. to 25° C. For example, the initial pH of the water-borne compositions, for example the latex paint compositions comprising a ketal (1), specifically adduct (1a), varies less than 0.5 pH units at 23° C., specifically less than 0.2 pH units at 23° C. pH, over about 1 week, over about 2 weeks, or over about four weeks, or even more at a temperature of 10° C. to 25° C.

Furthermore, the water-borne coating compositions, particularly the paint compositions can have very good overall performance, in particular one or more of viscosity, dry times, sag resistance, flow and leveling, hardness, specular gloss, dry film adhesion, impact flexibility, dilute alkali resistance, water resistance, stain resistance, solvent resistance, hydraulic fluid resistance, weatherability, and good heat storage stability.

In a specific embodiment, a latex paint composition comprises a vinyl acrylic emulsion, water, pigment, and 2EH-LPK. Vinyl acrylic emulsions are particularly suited for interior and exterior architectural coatings. The composition can exhibit excellent pigment binding, scrub resistance, stain resistance, exterior durability, chalk resistance, and grain crack resistance. The composition can also have good hiding and gloss as well as excellent thickening performance. Additionally, the composition can show low contribution to VOC content, high hydrolytic stability at a high alkaline pH level, and a low minimum film forming temperature.

In a specific embodiment, a latex paint composition comprises an acrylic emulsion, water, pigment, and 2EH-LPK. Acrylic emulsions are particularly suited for wall paints and interior/exterior architectural trim paints. The composition can exhibit excellent wet and dry adhesion over a chalky surface and aged alkyd substrates, blister resistance, grain crack resistance, and tint retention. The composition can have excellent exterior durability and very good efflorescence and alkali resistance. Further, the composition possesses excellent resistance to gloss loss, corrosion, fading, chalking, chemicals, and solvents. Additionally, the composition shows negligible contribution to VOC content, high hydrolytic stability at a high alkaline pH level, and a low minimum film forming temperature.

The inventors hereof have also discovered that the long-chain ketal adducts of ketocarboxy esters (1) offer a combination of properties that make them useful in a broad variety of cleaning compositions. In particular, the ketal adducts (1) have low volatility. Under normal conditions of manufacture, storage, and use, they are not reactive with many of the other materials that are commonly found in personal care or cleaning formulations. A further advantage is that the ketal adducts (1) are stable under basic conditions. Moreover, certain the ketal adducts (1) can be derived from biological feedstocks.

Exemplary cleaning compositions include but are not limited to laundry detergents, dishwasher cleaning formulations, hard surface cleaners, soft surface cleaners, glass cleaner compositions, and oven cleaners. Exemplary cleaning compositions also include stripping and removal compositions such as formulations for paint stripping, graffiti removal, ink cleaning and removal, adhesive removal, mastic removal, photoresist removal, wax stripping, asphalt removal, concrete cleaning, form cleaning, mold cleaning, hand cleaning, body cleaning, sap/pitch removal, oil stain cleaning and removing, parts degreasing, and engine degreasing. The ketal adducts of formula (1), specifically (1a) have excellent combination of properties for use in these applications, including solubilizing activity, low flammability, long work times, biodegradability, non-corrosiveness, and low odor. The cleaning compositions can be in the form of a solid, a gel, a liquid, an emulsion. A single composition can have more than one use, for example a single composition can be used as both a paint and ink remover, as a paint, oil, and grease remover.

In an embodiment, the cleaning compositions contain only ketal adducts of formula (1), specifically (1a), and 0 to 1 wt. % water, based on the total weight of the removal compositions. Such cleaning compositions can be removal compositions, for example, a paint remover, graffiti remover, ink remover, adhesive remover, mastic remover, photoresist remover, wax remover, asphalt remover, concrete cleaner, form cleaner, sap remover, oil remover, or grease remover.

In another embodiment, the cleaning compositions comprise the ketal adducts of formula (1), specifically (1a); 0 to 1 wt. % water, based on the total weight of the removal composition; and one or more additional components, for example a cosolvent and/or other components such as a plurality of abrasive particles, an organic amine, antioxidant, biocide, colorant, corrosion inhibitor, defoamer, dye, enzyme, light stabilizer, odor masking agent, plasticizer, preservative, rust inhibitor, surfactant, thickener, or a combination comprising at least one of the foregoing.

In still another embodiment, the cleaning compositions comprise from 20 to 99 wt. %, of water, from 0.1 to 40 wt. % of the ketal adducts of formula (1), specifically (1a) and from 0.1 to 20 wt. % of at least one surfactant. In yet another embodiment, the cleaning compositions comprise from 20 to 99 wt. %, of water, from 0.1 to 40 wt. % of the ketal adducts of formula (1), specifically (1a), and from 0.1 to 45 wt. % of at least one surfactant and one or more additional components, for example a cosolvent and/or other components such as a plurality of abrasive particles, an organic amine, antioxidant, biocide, colorant, corrosion inhibitor, defoamer, dye, enzyme, light stabilizer, odor masking agent, plasticizer, preservative, rust inhibitor, surfactant, thickener, soil suspending agent, builder or chelating agent, bleach, bleach activator, bleach stabilizer, and pH control agent, hydrotrope, and fabric softening ingredient.

Exemplary cosolvents include:

aliphatic hydrocarbons, for example C6-30 straight, branched-chain, or cyclic aliphatic hydrocarbons, that are specifically liquid at ambient temperatures and have a boiling point of at least about 100° C., e.g., mineral oil (also referred to as liquid petrolatum or liquid paraffin), mineral spirits (also referred to as ligroin or petroleum spirits), and low flashpoint cuts of hydrocarbon distillates (e.g., Conosol® C-145 (primarily of C10-13 cycloparaffinic and isoparaffinic hydrocarbons), Conosol® C-170 (composed primarily of C10-15 cycloparaffinic and isoparaffinic hydrocarbons), Conosol® C-200 (a composed primarily of C12-16 cycloparaffinic and isoparaffinic hydrocarbons), and Conosol® 215 (composed primarily of C12-15 cycloparaffinic and isoparaffinic hydrocarbons), from Calumet Specialty partners);

aromatic hydrocarbons, for example naphthalene, C1-8 alkyl derivatives of benzene, and C1-8 alkyl derivatives of naphthalene, specifically toluene, xylene (o, m, or p), cumene, ethyl benzene, mesitylene, durene, sec-amylbenzene, n-butylbenzene, naphthalene, and methyl naphthalene;

terpenes, for example, turpentine, alpha-pinene, beta-pinene, and d-limonene;

organic sulfur-containing compounds such as sulfoxides, for example dimethyl sulfoxide (DMSO);

chlorinated solvents, for example chlorinated C1-6 aliphatic compounds such as allyl chloride, carbon tetrachloride, chloroform, 1,1-dichloroethane, dichloroethylether, 1,2-dichloroethylene, dichloroisopropyl ether, ethyl chloride, ethylene dichloride, isopropyl chloride, methyl chloride, perchloroethylene, propylene dichloride, 1,1,2-trichloroethane, trichloroethylene 1,2,3 trichloropropene, and methylene chloride (dichloromethane, or DCM);

alcohols, for example amyl alcohol, n-butanol, 3-butoxy-ethyl-2-propanol, benzyl alcohol, benzyloxyethanol, diethoxyethanol, diisobutyl carbinol, dimethyl heptanol, ethanol, 2-ethylhexanol, ethylene glycol, glycerin, 1-hexanol, isobutanol, isopropanol, methanol, methyl amyl alcohol, 2-methyl-1-butanol, 1-pentanol, 1-propanol, propylene glycol, and 2,2,4-trimethyl-1,3-pentanediolmonoisobutyrate (commercially available as UCAR FILMER™ IBT from Dow Chemical Co.);

glycol ethers, for example diethylene glycol methyl ether, diethylene glycol mono-n-butyl ether (commercially available as Butyl CARBITOL from Dow), diethylene glycol monoethyl ether (commercially available as CARBITOL from Dow), diethylene glycol monohexyl ether (commercially available as Hexyl CARBITOL from Dow), diethylene glycol monomethyl ether (commercially available as Methyl CARBITOL from Dow), diethylene glycol monopropyl ether (commercially available as Propyl CARBITOL from Dow), diethylene glycol n-butyl ether acetate (commercially available as Butyl CARBITOL™ Acetate from Dow), dipropylene glycol monobutyl ether (commercially available as DOWANOL™ DPnB from Dow), dipropylene glycol monomethyl ether (commercially available as DOWANOL DPM from Dow), dipropylene glycol monopropyl ether (commercially available as DOWANOL DPnP from Dow), dipropylene glycol tert-butyl ether, ethylene glycol methyl ether acetate (commercially available as Methyl CELLOSOLVE Acetate from Dow), ethylene glycol monobutyl ether (commercially available as Butyl CELLOSOLVE from Dow), ethylene glycol monohexyl ether (commercially available as Hexyl CELLOSOLVE from Dow), ethylene glycol monopropyl ether (commercially available as Propyl CELLOSOLVE from Dow), ethylene glycol n-butyl ether acetate (commercially available as Butyl CELLOSOLVE Acetate from Dow), ethylene glycol phenyl ether (commercially available as "DOWANOL™ EPh" from Dow), heptaethylene glycol monobenzyl ether, heptaethylene glycol monophenyl ether, hexaethylene glycol monobenzyl ether, hexaethylene glycol monophenyl ether, pentaethylene glycol monobenzyl ether, pentaethylene glycol monophenyl ether, propylene glycol ethyl ether, propylene glycol methyl ether acetate (commercially available as DOWANOL™ PMA from Dow), propylene glycol monobutyl ether (commercially available as DOWANOL PnB from Dow), propylene glycol monomethyl ether (commercially available as DOWANOL PM from Dow), propylene glycol monopropyl ether (commercially available as DOWANOL PnP from Dow), propylene glycol phenyl ether (commercially available as "DOWANOL PPh" from Dow), tetraethylene glycol monobenzyl ether, tetraethylene glycol monophenyl ether, triethylene glycol methyl ether, triethylene glycol monobenzyl ether, triethylene glycol monophenyl ether, tripropylene glycol methyl ether (commercially available as DOWANOL TPM from Dow), and tripropylene glycol n-butyl ether (commercially available as DOWANOL TPnB from Dow);

water-soluble ethoxylates of propylene glycol monophenyl ether (specifically, containing an average of at least 2 oxyethylene moieties per molecule);

water-soluble or water-dispersible polymeric amines such as poly(ethylene imine);

amides such as acetamidophenol, N,N-dimethyl formamide (DMF), and acetanilide, and cyclic amides such as 1-methyl-2-pyrrolidone (NMP), N-ethyl-2-pyrrolidone, N-isopropyl-2-pyrrolidone, N-cyclohexyl-2-pyrrolidone, 2-hydroxyethyl-2-pyrrolidone, N-dimethylaminopropyl-2-pyrrolidone, vinyl-pyrrolidone, and 2-pyrrolidone;

amines such as 2-(2-aminoethoxy)ethanol, 2-acetyl-1-methylpyrrole, 2-amino-2-methyl-1-propanolalkanolamines (e.g., n-butyldiethanolamine, diethanolamine, diisopropanolamine, dimethylethanolamine, ethanolamine, isopropanolamine, methylisopropanolamine, phenyl diethanolamine, and triethanolamine), cyclic amines (e.g., N-methylpyrrolidine, N-methylpyyrole, morpholine, and oxazolidines), n-butylaminoethanol, diethylaminoethanol, diglycolamine, 2-methylaminoethanol, and trialkylamines (e.g. triethylamine);

ketones and cyclic ketones such as isobutyl heptyl ketone, isophorone, methyl ethyl ketone, methyl isobutyl ketone, diisobutyl ketone, diacetone alcohol, acetophenone, methyl n-amyl ketone, cyclohexanone, and cycloheptanone;

dialkyl carbonates such as dimethyl carbonate, diethyl carbonate, dipropyl carbonate, diisopropyl carbonate, and dibutyl carbonate;

cyclic carbonates such as propylene carbonate and ethylene carbonate;

monoesters such as amyl acetate, benzyl acetate, benzyl benzoate, butyl acetate, ethyl acetate, ethyl propionate, ethyl lactate, isobutyl acetate, isopropyl acetate, n-butyl propionate, n-pentyl propionate, n-propyl acetate, n-propyl propionate, butyl lactate, the C1-4 alkyl esters of C6-22 saturated or unsaturated carboxylic acids, such as the methyl ester of C6-14 unsaturated fatty acids; the glycerol ester of fatty acids, including those derived from vegetable oils such as linseed, coconut, palm, soybean, cottonseed, groundnut, sunflower, rape, sesame, olive, corn, safflower, palm kernel, castor oil, peanut, fish, lard, mustard seed, poppyseed, turpentine, and tall oil, and ethyl 3-ethoxypropionate (commercially available as UCAR™ Ester EEP from Dow Chemical Co.);

dibasic esters such as dimethyl adipate, dimethyl succinate, dimethyl glutarate, dimethyl malonate, diethyl adipate, diethyl succinate, diethyl glutarate, dibutyl succinate, dibutyl glutarate and products available under the trade designations DBE™, DBE-3, DBE-4, DBE-5, DBE-6, DBE-9, DBE-IB, and DBE-ME from Invista;

alkoxylated aromatic alcohols as described in U.S. Pat. No. 7,179,775, in particular the alkoxylated aromatic alcohols containing at least one aromatic ring per molecule and alkoxylate units of general formula —$(CR^1R^3—CR^2R^4—O)_n$—$R^5$ wherein: $R^1$, $R^2$, $R^3$, and $R^4$ are each independently hydrogen or methyl; $R^5$ is hydrogen, a C1-6 alkyl, or phenyl; and n is 2-10, wherein the alkoxylate units are attached to the aromatic ring directly or through an ether (oxygen) linkage or an oxymethylene (—$CHR^8O$—) linkage, wherein $R^8$ is hydrogen or $C_{1-4}$ alkyl. A combination comprising any one or more of the foregoing cosolvents can be used.

In an embodiment, the cosolvent is NMP.

The ratio of the ketal adducts of formula (1), specifically (1a) to cosolvent can vary widely depending on the ketal adducts of formula (1), the cosolvent, and the intended use, and can be from 1:99 to 99:1, specifically from 10:90 to 90:10, more specifically from 20:80 to 80:20, from 30:70 to 70:30, or from 40:60 to 60:40, all by volume.

It is to be understood that a single additive can have more than one function, and that characterization of an additive as having that function (e.g., as a cosolvent) does not exclude the additive from performing another function. The concentrations of the individual additives of the cleaning compositions can be varied as depending upon components of the cleaning composition, the type of material to be removed, and the rate at which material removal is to be effected. Optimal concentrations for a particular application can be readily determined by a worker skilled in the art using standard experimental methods, and the guidelines provided below.

The organic amine accelerators can include those listed above as cosolvents. Accelerators are believed to accentuate the performance of the composition by chemically attacking the organic binder of a coating and thereby weakening the adhesion and cohesion of the coating. Exemplary amine accelerators include ethanolamine, diethanolamine, ethylenediamine tetraacetic acid, morpholine, triethanolamine, triethylamine, and 2-(N,N'-diethylamino)ethanol). When used as an additive, the amine accelerator can be present in an amount from 0.1 to 20 wt. %, or from 1 to 10 wt. %, although these amounts are merely illustrative.

Exemplary organic acid accelerators include C1-22 carboxylic acids (e.g., formic acid, acetic acid, propionic acid, oleic acid, oxalic acid, and hydroxyacetic acid). When used as an additive, the organic acid accelerator can be present in an amount from 0.1 to 20 wt. %, or from 1 to 10 wt. %, although these amounts are merely illustrative.

Corrosion inhibitors can be present, particularly where the composition is provided in a metal container, or when an acid accelerator is present. Corrosion inhibitors can be, for example, a molecule that has both an oil soluble portion and a water soluble portion, such as an amphoteric surfactant containing an amine functionality in an amount from about 0.05% to about 2 wt. %, specifically about 0.25% to about 1.0%, such as the disodium N-lauryl iminodipropionate esters available as DERIPHAT® amphoteric surfactants from Cognis Corporation. Other corrosion inhibitors include amine soaps of fatty acids and fatty alkanolamides such as the $C_8$ to $C_{18}$ fatty alkanolamides, examples of which include STANDAMID® alkanolamides, available from Cognis Corporation. Such corrosion inhibitors can also be used for post-application anti-corrosion effects on surfaces that will rust or corrode because of the presence of water in the cleaning compositions, such as on metal surfaces such as iron and steel and the like.

The cleaning compositions can also contain an effective amount of odor masking agents, such as essential oils, aroma chemicals, perfumes, and the like, for example, ambergris, borneol and its esters, carvone, castoreum, civet, cinnamaldehyde, citrals, clove oil, galbanum, jasmine, limonene, linalool and its esters, pinenes (alphas, betas, etc.), rosemary oil, sandalwood, terpineols, terpinenes, and the like, benzaldehyde, benzoin, isoamyl acetate (banana); isobutyl propionate (rum); methyl anthranilate (grape); benzyl acetate (peach), dipentene, methyl butyrate (apple); ethyl butyrate (pineapple); octyl acetate (orange); n-propyl acetate (pear); ethyl phenyl acetate (honey), and the like. An effective amount of such odor masking agents will be readily determinable by those skilled in the art, and can be, for example, about 0.25% to about 2.50 wt. % the removal composition specifically about 0.4% to about 1.0%.

Exemplary plasticizers include phthalate esters, for example dibutyl phthalate, diethylhexyl phthalate, and diethyl phthalate; aliphatic diesters, for example dioctyl adipate; terephthalate esters, for example dioctyl terephthalate; citrate esters, for example acetyl triethyl citrate and acetyl tri-n-butyl citrate; ketal based plasticizers, such as those described in PCT Application WO 2010/151558, or a combination comprising at least one of the foregoing. When used, the plasticizer is present in an amount from about 0.1 to about 10 wt. %, based on the total weight of the removal composition.

A wide variety of surfactants can be utilized, depending on the application, and can be amphoteric, anionic, cationic, nonionic, or zwitterionic. A surfactant or combination of surfactants can be present in order to improve wetting of the soil or coating to be removed and to hasten penetration of the active components. In addition, a surfactant can facilitate water rinsing and water clean-up of the substrate after removal of the soil or coating. Exemplary amphoteric surfactants include amine oxide compounds having the formula RR'R"N→O wherein each R, R' and R" is independently a $C_1$-$C_{24}$ alkyl, aryl or arylalkyl group) that can optionally contain one or more P, O, S or N heteroatoms. Exemplary amphoteric surfactants also include betaine compounds of the formula RR'R"N$^+$(CH$_2$)$_n$C(O)O$^-$ wherein each R, R' and R" is independently a $C_1$-$C_{24}$ alkyl, aryl or arylalkyl group) that can optionally contain one or more P, O, S or N heteroatoms and n is about 1 to about 10. A combination comprising at least one of the foregoing can be used.

Exemplary anionic surfactants include the water-soluble salts of alkylbenzene sulfonates such as the isopropylamine salt of a $C_{10-14}$ alkyl benzene sulfonic acid, and/or a $C_{8-14}$ fatty alcohol sulfate, alkyl sulfates, alkyl polyethoxy ether sulfates, paraffin sulfonates, alpha-olefin sulfonates and sulfosuccinates, alpha-sulfocarboxylates and their esters, alkyl glyceryl ether sulfonates, fatty acid monoglyceride sulfates and sulfonates, alkyl phenol polyethoxyether sulfates, the water-soluble salts or esters of alpha-sulfonated fatty acids containing from about 6 to about 20 carbon atoms in the fatty acid group and from about 1 to about 10 carbon atoms in the ester group, and the like. When present, the anionic surfactant can be present in the composition in an amount from about 0.1 to about 15 wt. %, from about 3 to about 12 wt. %, and most specifically from about 5 to about 10 wt. %, based on the weight of the composition. A combination comprising at least one of the foregoing can be used.

In addition to, or instead of an anionic surfactant, a short-chain surfactant can be present, for example $C_3$-$C_6$ alcohols, glycols, glycol ethers such as propylene glycol n-butyl ether, pyrrolidones, glycol ether esters, and the like. A combination comprising at least one of the foregoing can be used.

Exemplary cationic surfactants include quaternary amine compounds having the formula RR'R"R'''N$^+$X where each R, R', R" and R''' is independently a $C_1$-$C_{24}$ alkyl, aryl or arylalkyl group) that can optionally contain one or more P, O, S or N heteroatoms, and X is F, Cl, Br, I or an alkyl sulfate. A combination comprising at least one of the foregoing can be used.

Exemplary nonionic surfactants include alcohol ethoxylates (e.g., $C_6$-$C_{24}$ or $C_6$-$C_{16}$ alcohol ethoxylates) having 1 to about 20 ethylene oxide groups (e.g., about 9 to about 20 ethylene oxide groups), alkylphenol ethoxylates (e.g., $C_6$-$C_{24}$ or $C_8$-$C_{10}$ alkylphenol ethoxylates) having 1 to about 100 ethylene oxide groups (e.g., about 12 to about 20 ethylene oxide groups), alkylpolyglycosides (e.g., $C_6$-$C_{24}$ or $C_6$-$C_{20}$ alkylpolyglycosides) having 1 to about 20 glycoside groups (e.g., about 9 to about 20 glycoside groups). A combination comprising at least one of the foregoing can be used.

As a general guide, the amount of surfactant can be about 0.1 to about 20%, about 0.1 to about 15% or about 2 to about 15% of the total weight of the cleaning composition.

In an embodiment, the disclosure includes a composition comprising a surfactant as described above and the ketal adducts of formula (1), specifically (1a). In these embodiments, the ratio of surfactant to the ketal adducts of formula (1), specifically (1a) can range from 50:1 to 1:50, preferably 20:1 to 1:10. These compositions can be prepared as intermediates to be used in final formulations, such as for cleaning products.

Thickeners can be present to adjust the rheological properties of the cleaning compositions. For example, the removal of partially dried paint removal from automotive paint spray booths is generally performed by spraying a cleaning composition such as coatings remover onto the spray booth. The coatings remover must be thin enough to spray easily but must rapidly build in viscosity under low shear conditions to effectively cling to vertical surfaces. A higher viscosity formulation is generally desired if the coatings remover is to be painted on while a low viscosity formulation containing no added thickener can be used where the coated substrate is to be soaked in a tank. Thickeners can also serve to increase the effectiveness of the coatings removers by decreasing the rate of evaporation of the volatile components after application to a coated substrate. Use of a thickener in the composition enables the composition to be applied onto vertical surfaces without any attendant dripping or run-off therefrom and also inhibits dissipation of the composition into porous substrates such as brick or concrete.

Exemplary thickeners are natural or synthetic clays including bentonite, hectorite, smectite and other silicates such as available grades of BENTOLITE™, CLAYTONE™ and GELWHITE™ bentonites, PERMONT™ smectites, CLOISITE™ magnesium aluminum silicates, LAPONITE™ silicates and GARAMITE™ silicates (all available from Southern Clay Products, Inc.) and available grades of OPTIGEL™ bentonites, hectorites, smectites and other clays (all from Sued-Chemie Group); stearates of organoclay compounds such as tetraalkyl ammonium bentonite; gums and other polysaccharides such as carrageenan gum (e.g., GENU-VISCO™ X-906-02 (from CP Kelco)), cassia gum, diutan gum (e.g., GEOVIS™ XT, KELCO-CRETE™ 80, KELCO-CRETE 200 and KOC617 (all from CP Kelco)), gellan gum (e.g., KELCOGEL™, KELCOGEL F and KELCOGEL LT 100 (all from CP Kelco)), guar gum, Gum Arabic, Gum Tragacanth, locust bean gum, whelan gum and Xanthan gum (e.g., KELZAN™, KELZAN AR, KELZAN ASX, KELZAN ASX T, KELZAN CC, KELZAN HP, KELZAN RD, KELZAN S, KELZAN ST, KELZAN T, KELTROL™, KELTROL T and KELTROL TF (all from CP Kelco) and VANZAN™ and VANZAN D (both from R.T. Vanderbilt Co.)); hydrocolloids such as NOVEGUM™ C865, NOVEGUM C866 and NOVEGUM G888 (all from Noveon, Inc.); alginates such as agar; cellulose ethers such as ethyl cellulose, hydroxyethyl cellulose, ethyl hydroxyethyl cellulose, methyl cellulose, hydroxypropyl cellulose, hydroxypropyl methyl cellulose, and other alkyl or hydroxyalkyl cellulose ethers, commercially available, e.g., as METHOCEL™ K15MDGSE, METHOCEL K4MDGSE, METHOCEL 311, METHOCEL F4M PRG and METHOCEL OS (all from Dow), XDS 8898.5 cellulose ether (from Dow), and KLUCEL™ H, KLUCEL M or KLUCEL G (all from Ashland, Inc.); acrylic acid homopolymers or copolymers, e.g., those which can be neutralized with a salt including associative or non-associative thickeners such as ACUSOL™ 801s, ACUSOL 810, ACUSOL 810A, ACUSOL 820, ACUSOL 823 and ACUSOL 830 acrylate polymers (all from Rohm & Haas Co.) or those which can be crosslinked (e.g., with a polyalkenyl polyether) including CARBOPOL™ 674, CARBOPOL 676, CARBOPOL ETD 2691, CARBOPOL ETD 2623, CARBOPOL EZ-3, CARBOPOL EZ-3A, CARBOPOL EZ-4 and CARBOPOL ULTREZ™ 21 (all from Noveon, Inc.); PEMULEN™ 1622 copolymer (from Noveon, Inc.); polyethylene oxides (e.g., high molecular weight polyethylene oxides) such as polyethylene glycols and methoxypolyethylene glycols; polyvinyl alcohols; polyvinyl pyrrolidone; starches; polyurethanes including RHEOLATE™ 266 (from Elementis Specialties, Inc.), and available grades of OPTIFLO™ associative thickeners (all available from Sud-Chemie Group); and methyl vinyl ether/maleic anhydride copolymers. Other possible thickeners include hydrophobe-modified ethoxy urethane (HEUR) thickeners, hydrophobe-modified alkali soluble emulsion (HASE) thickeners, hydrophobe-modified hydroxyethyl cellulose (HM-HEC) thickeners, and HEUR-ASE combination thickeners. A combination comprising at least one of the foregoing can be used.

The thickener can be used in an amount from about 0.1 to about 30 wt. %, specifically about 2 to about 20 wt. %, and most specifically about 3 to about 10 wt. %, based on the total weight of the cleaning composition.

A detergency builder is commonly present in laundry detergents, hard surface cleaner products and dishwashing liquids, and can be present in cleaning compositions of this disclosure. Examples of such builders include N-diethyleneglycol-N,N-diacetic (DIDA) acid polyphosphates (e.g., potassium pyrophosphate), nitrilotriacetates (e.g., $Na_3NTA$), sodium ethylenediaminetetraacetate (EDTA), sodium ethylenetriaminepentaacetate, sodium citrate, sodium carbonate, sodium metasilicate and zeolites, e.g., zeolites having a cation exchange capacity (measured as $CaCO_3$) of 200 mg or greater per gram of zeolite. Enzymes such as proteases and amylases are also frequently present in cleaner compositions, especially laundry detergent products and prewash products.

The cleaning composition can contain a bleach such as sodium hypochlorite, sodium perborate, diperoxydodecanedioic acid, sodium dichloroisocyanurate, m-chloroperoxybenzoic acid and peroxide based bleaches. An advantage of this disclosure is that the alkyl ketal esters are stable in bleach solutions, and thus can add good solvency for oily soils into a bleach-containing composition. A bleach-containing composition of the disclosure can also contain one or more bleach activators such as tetra acetyl ethylene diamine and sodium nonanoyloxybenzene sulfonate.

The cleaning composition can further contain one or more soil suspending agents such as sodium carboxymethyl cellulose; one or more bleach stabilizers such as sodium diethylenetriamine-pentamethylenephosphonate and sodium diethyl enetriaminopentaacetate; one or more hydrotropes such as sodium toluene sulfonate, sodium cumene sulfonate and potassium xylene sulfonate; one or more fabric softening ingredients such as smectite clay and tallowedimethylammonium chloride.

In a specific embodiment the cleaning composition is a liquid laundry detergent that may be for hand or machine washing, and which comprises 50 to 95 weight % water; 0.1 to 25 weight % of the ketal adducts of formula (1), specifically (1a); 0.1 to 45 weight % of a surfactant; and a builder, a chelating agent, a chlorine bleach, a non-chlorine bleach, an abrasive, an anti-deposition agent, a brightening agent, or a combination comprising at least one of the foregoing. In liquid laundry products, the ketal adducts of formula (1), specifically (1a) may perform any or all of several functions, such as solubilizing or emulsifying the surfactant or other ingredients and functioning as an active cleaning agent.

For example, a liquid laundry formulation may contain, as percentages of the total formulation weight: a) water: 50-95%; b) the ketal adducts of formula (1), specifically (1a): 0.1-50%, more typically 1-25%, specifically 1-10%; c) one or more surfactant(s): 0.1-45%, specifically 1-40%, more specifically 1-35%, still more specifically 1-10%, but in some cases more specifically from 15-35%; the surfactants advantageously being (1) at least one anionic surfactant, (2) a nonionic surfactant, (3) a mixture of at least one nonionic surfactant and at least one anionic surfactant, (4) one or more of an l3 alkyl glycoside, an alkyl betaine or a sulfo succinate salt, or (5) a mixture of (4) with (1), (2) or (3); h) one or more builders or chelating agents, particularly a chelating agent such as EDTA or DIDA: 0-30%, specifically, if present, 0.1-30%, more specifically, if present, from 1-25% and still more specifically, if present, from 1-10%; i) one or more bleaches, including, for example, a chlorine bleach such as sodium hypochlorite or a non-chlorine bleach: 0-10%, specifically, if present 0.1-5%; o) one or more abrasives: 0-30% specifically if present 1-20% p) one or more anti-redeposition additives, such as carboxymethylcellulose salts and cellulose acetate polymeric agents, 0-5%, specifically if present 0.1 to 2%; and q) brightening agents, including optical brightening agents, fluorescent brightening agents and fluorescent whitening agents, including, for example, sulfonated triazine-stilbenes, coumarins, imidazolines, diazoles, triazoles, benzoxazolines and biphenyl stilbenes, 0-3, specifically if present 0.1 to 1.

In addition, a liquid laundry product may contain any of optional components for the cleaning compositions as described herein singly or in any combination of any two or more of them. Any or all of optional components may be omitted in any particular liquid laundry formulation.

Some exemplary liquid laundry formulations in accordance with the disclosure follow. The indicated percentages are weight percents based on the total formulation weight. The function of these the ketal adducts of formula (1), specifically (1a) in liquid laundry formulations is similar to those described before with respect to hard surface cleaners below.

| Aqueous Liquid Laundry Detergent | Amount |
|---|---|
| Sodium hydroxide | 0-1% |
| Sodium chloride | about 1% |
| Nonionic surfactant (e.g., ethoxylated alcohol) | 0-20, specifically 0.1-6% |
| Anionic surfactant (e.g., benzenesulfonic acid, alkylated) | 1-20, specifically 1-10% |
| Builder(s) | 0-10% |
| Anti-redeposition agent | 0-1% |
| Proteolytic enzymes | 0-2% |
| Brightener (fluorescing agent) 0-1% Buffer(s) | 0-5% |
| Ketal adducts of formula (1), specifically (1a) | 0.1-80% |
| Water (balance of total formulation) | |

| Aqueous Laundry Stain Remover | Amount |
|---|---|
| Proteolytic enzyme | 0-<1% |
| Surfactant | 10-20% |
| Chelating agent | 0.5-1.5% |
| Ketal adducts of formula (1), specifically (1a) | 0.1-80% |
| Water (balance of total formulation) | |

| Aqueous Dry-cleaning Composition | Amount |
|---|---|
| Water | 60-95% |
| Polyacrylates | 0.2-0.5% |
| Mixed glycol ethers | 0-30% |
| Ketal adducts of formula (1), specifically (1a) | 0.1-80% |
| Surfactant(s) | >0.1% |
| 1,2-Octanediol | 0-5% |

Any of the aforementioned liquid laundry formulations, can be prepared in concentrated form by reducing the amount of water, and correspondingly increasing the concentration of at least the surfactant, and advantageously the concentration of both the ketal adducts of formula (1), specifically (1a) and the surfactant. Such a concentrated hard surface cleaner formulation may contain, by weight, up to 50% combined of water and/or volatile organic compound, and more typically contains no more than 40% thereof. Such a concentrated formulation often contains, from 5 to 70% or from 10 to 50% by weight of at least one the ketal adducts of formula (1), specifically (1a) as described herein and from 5 to 90%, 5 to 70%, or from 10 to 50% by weight of at least one surfactant.

In another specific embodiment the cleaning composition is a hard surface cleaner having a general formulation as is known in the art, and which can be formulated for industrial, institutional, office or, home use. These can be formulated as, for example, general purposes hard surface cleaners, toilet cleaners, shower/bath/tile cleaners, disinfectants, soap scum removers, mildew removers, glass/mirror cleaners, or stain removers. Many of these cleaners are formulated as dilute solutions or emulsions, and many are applied by spraying. A hard surface cleaner can include least 20 wt. %, at least 50 wt. %, or as much as 99 wt. % of water; up to 50 wt. %, 0.1 wt. % to 50 wt. %, 1 wt. % to 25 wt. %, 3 wt. % to 15 wt. %, or 1 wt. % to 10 wt. % of the ketal adducts of formula (1), specifically (1a); and 0.01-40 wt. % of a surfactant, in particular a anionic or nonionic surfactant, each based on the total weight of the composition. The ketal adducts of formula (1), specifically (1a) can perform any or all of several functions, such as (1) soil dissolution and/or removal; (2) compatibilization of ingredients, particularly sparingly water-soluble ingredients into water; (3) formation of a cosolvent mixture in which one or more other ingredients are dissolved or dispersed, (4) elimination or reduction of surfactants and/or organic solvents or others. The surfactant can include one or more materials derived from plant sources, such as one or more alkyl glycosides, an alkyl betaine, or a sulfosuccinate salt.

In specific embodiments, a hard surface cleaner formulation can comprise, as percentages of the total formulation weight: a) water: 20-99%, more typically 50-95%; b) one or more the ketal adducts of formula (1), specifically (1a): 1-50%, more typically 1-25% or 1-10%; c) one or more surfactant(s): 0.01-20%, specifically 0.1-15%, more specifically 0.25-10%, still more specifically 1-7% and in some cases 1-5%; the surfactant(s) specifically being (1) at least one anionic surfactant, (2) at least one nonionic surfactant, (3) a mixture of at least one nonionic surfactant and at least one anionic surfactant or nonionic surfactant, (4) one or more of a an alpha, beta-alkyl glycoside, an alkyl betaine or a sulfosuccinate salt, or (4) a mixture of (4) with (1), (2) or (3).

The formulation can also comprise d) one or more propellants, which are generally low-boiling hydrocarbons such as butane, pentane, hexane and cyclohexane or chlorinated and/or fluorinated hydrocarbons that have boiling temperatures of from −10° C. to 50° C.; e) one or more sparingly water-miscible organic solvent(s): generally from 0-10%, specifically, if present, 0.1-5%. This can be, for example, one or more of the long-chain alcohols, glycol ethers, hydrocarbons, halogenated hydrocarbons, Cβ-9 alkyl aromatic compounds, olefins, terpenes, terpene oxides, terpenoids, oils, and natural oil derivatives. The formulation can also comprise f) one or more highly water-miscible organic solvents, such as a lower alcohol (e.g., ethanol and 1-propanol), acetone, glycols, and glycol ethers: 0-10%, specifically, if present, 0.1-5%; g) one or more antimicrobials, 0-5%, specifically, if present 0.1-2%, some examples of include quaternary ammonium chlorides such as C12-16 alkyl dimethyl benzyl ammonium chloride and various phenylphenol compounds; h) one or more builders or chelating agents, particularly a chelating agent such as a phosphate salt, a citrate salt, EDTA, or DIDA: 0-30%, specifically, if present, 0.05-10% and more specifically, if present, from 0.5-1%, still more specifically, if present, from 2-8% and even more specifically, if present, from 2-6%; i) one or more bleaches, including, for example, a chlorine bleach such as sodium hypochlorite or a non-chlorine bleach such as hydrogen peroxide or other peroxy compound: 0-10%, specifically, if present 0.1-5%; j) one or more pH control agent(s) (e.g., acids, bases, pH buffers): 0-2%, if present specifically 0.05 to 1%; k) one or more colorants: 0-5%, specifically if present 0.1-2%; l) one or more inorganic water-soluble salts such as sodium sulfate: 0-10%, specifically if present 0.1-5%; m) one or more viscosity thickeners, including, for example a water-soluble polymer: 0-10%, specifically if present 0.1-5%; n) one or more proteolytic enzymes, 0-5%: specifically if present 0.1-1%) one or more abrasives; and p) one or more fragrances. Components b) and d)-p) as described above can be present in any combination of any two or more of them. Any or all of components e)-n) can be omitted in any particular hard surface cleaner formulation. Component d) is typically present in a spray cleaner formulation. It is noted earlier that in some instances, a single material can perform multiple functions in a hard cleaner formulation. Component j) is often present to provide for a pH of from 3.5 or higher, specifically from 6 to 10.

A method of preparing a cleaning composition comprises combining the ketal adducts of formula (1), specifically (1a) and any cosolvent or other component to form the cleaning composition. The order of the addition is not particularly limited. The ketal adducts of formula (1), specifically (1a) and additives can be added in any suitable order to the additional component(s) present in the composition to provide the cleaning composition.

When used with cosolvents or other components, the cleaning compositions can be provided as a concentrate. The concentrates are usually diluted in water for use as a working water-based cleaning composition. In an embodiment, a two-part concentrate package can be provided which typically comprises a Part A and a Part B, where each part contains a component likely to react with the other part, for example the ketal and an amine in Part A and an inorganic base in Part B.

The cleaning compositions can alternatively be formulated in other forms useful for removal or cleaning compositions, for example gels, wipes, aerosols, and the like. The removal compositions can be formulated in gel form by the addition of an effective amount of a gelling agent such as fumed silica, organic gums, polymers, copolymers, paraffin wax, bentonite clay, and cellulose ethers such as methyl cellulose and hydroxypropyl methyl cellulose commercially available as METHOCEL® cellulose ethers, from Dow Chemical. Wipes are generally a natural or synthetic fabric piece impregnated with the gel or liquid removal composition. When used as an aerosol, the cleaning formulations are formulated under pressure with a propellant as is known in the art.

A method of cleaning, for example, removing a material such as a coating, soils and/or stains from a substrate comprises contacting the material with a composition comprising the ketal adducts of formula (1), specifically (1a) under conditions that effect the removal, for example for a time effective to dissolve and/or lift the material; and separating the dissolved and/or lifted material from the substrate. As used herein, "dissolved" includes partial dissolution of a material, often referred to as softening, such that the material can be further removed from the substrate by rinsing or mechanical action. Of course, the cleaning composition can also be at least partially removed by separating the material.

The cleaning compositions can be used to remove a wide variety of materials, generally those soluble or softenable by organic solvents. Examples include materials such as soils, stains, grease, inks for all types of substrates, including paper, wood, plastic, metal, textiles, ceramics, stone, skin, and for indoor or for outdoor use; adhesives and sealants, for example silicone, polyurethane, epoxy, polyvinyl acetate (including copolymers with ethylene), phenolic, amino resin, cyano acrylate, polyester, polyamide, rubber (styrene-butadiene and natural) or acrylic adhesives and sealants; mastics; photoresists; waxes, for example floor wax, car wax, or bees wax; asphalts; saps (which as used herein includes pitches, rosins, tars, and natural resins such as tree sap); residual materials left in forms or molds, for example polymers such as alkyds, polyacetals, polyacrylates, polyacrylics, polyamides, polycarbonates, polyesters, polyethers, polyethylenes, polyimides, polystyrenes, polyurethanes, polyvinyls, silicones, natural and synthetic rubbers, and the like, and polymer additives; greases, for example silicone and petroleum-based greases; oils, including machine oil; and paints, finishes, and other coatings, for example, alkyd enamels, acrylic enamels, polyesters, polyurethanes, epoxy resin coatings, latex paints, oil-based paints, shellacs, phenolic coatings, gum varnishes, silicone coatings, polyvinyls, polyvinyl cinnamates, polyamides, polyimides, polyalkyl acrylates, polyalkyl methacrylates, drying oils, polyvinyl acrylates, and cellulosic resins.

The substrates that are treated with the cleaning compositions are reasonably resistant to the cleaning compositions, including natural and synthetic fabrics, wood, cardboard, and coated paper, especially if treated with a wax or other protective material, glass, thermoset resins, thermoplastic resins, ceramic, stone, masonry substrates, cement, or metals (e.g., aluminum alloys, zinc alloys, stainless steel, or galvanized steel). The cleaning compositions can further be used to a part of the human body, for example hands or hair, as well as animals.

Although the methods of contacting the surface with the cleaning composition can be accomplished in a number of ways, for example, in aerosol form or other spraying means such as by standard spray nozzles; brush application; dipping; coating; application in gel form such as from a squeeze bottle or brush, and the like, but immersion and spraying can be specifically mentioned. If the surface to be cleaned is readily accessible, then spraying can be used. The spraying pressure will usually be from 1.3 bars to 8.0 bars absolute pressure. The mechanical force of the impinging removal composition facilitates removal of the material. On the other hand, if the surface to be cleaned has recesses or other shapes that are not readily accessible, immersion can be used. Of course, both methods can be used in combination and/or varied in ways apparent to those skilled in the art. During or after contacting, mechanical action, such as scraping, peeling, rubbing, wiping, and the like can be employed to increase contact and/or aid in dissolution and/or lifting.

The contact time needed to produce an effective degree of dissolution and/or lifting of the material from a surface will depend on the nature and thickness of the material, the composition of the cleaning composition, including the ingredient concentrations, the temperature of the composition, and other factors. With some materials and under some conditions, contact times of a few minutes (e.g., 2-3 minutes) to an hour can be sufficient. Operating temperature when using the removal compositions can be from 0 to 180° C. or higher, specifically 15 to 90° C., or 21 to 55° C. The treatment is most conveniently carried out at ambient temperature, but lift time can be shortened as desired by heating the cleaning compositions and/or substrate. Heating can be achieved by local application of heat such as with a heat gun, or more general application of heat, such as with an electric heater, infrared heater, and the like. It is to be understood however, that those skilled in the art can determine optimal conditions for particular removal applications by minimal experimentation. Higher temperatures generally increase the rate at which the material is removed from the surface.

Separating the ketal adducts of formula (1), specifically (1a) and dissolved material from the substrate can include mechanical action, such as scraping, peeling, rubbing, wiping, and the like, or rinsing the substrate with additional removal composition or another solvent, including water or aqueous mixture of water with an organic solvent.

The ketal adducts of formula (1), specifically (1a) are also useful in perfume and flavorant formulations (hereinafter jointly referred to as fragrant compositions). The ketal adducts (1) offer a combination of properties that make them useful in a broad variety of fragrant compositions. In particular, the ketal adducts (1) have low volatility. Under normal conditions of manufacture, storage, and use, they are not reactive with many of the other materials that are commonly found in fragrant compositions, or the formulations in which fragrant compositions are used. A further advantage is that the ketal adducts (1) are stable under basic conditions. Moreover, certain of the ketal adducts (1) can be derived from biological feedstocks. Thus, the ketal adducts (1) can advantageously be used both as solvents as well as fixatives in fragrant compositions. Efforts continue to be made to find improvements in the performance of fragrant compositions, including their in-product shelf life, their delivery effectiveness, and their longevity or substantivity on various substrates. For example, during use, a substantial amount of perfume in a cleaning product is lost with rinse water and through drying. It is desirable to be able to overcome these process conditions and to ensure that the perfume material left on the substrate provides a maximum odor effect via the minimum amount of material. In an embodiment, the ketal adducts (1) can effectively function as a fragrance fixative, prolonging the effect of the fragrant composition and so prolonging fragrance life. In another embodiment, the ketal adducts (1) can effectively function to compatibilize the fragrant composition with waxes.

The fragrant composition comprises at least one fragrant compound (also referred to herein as a fragrant molecule). The fragrant molecule is also referred to as an aroma compound. The fragrant molecule can be a naturally occurring molecule or a synthetic molecule (e.g., a molecule that is synthesized in a laboratory from ingredients that are not naturally occurring). Naturally occurring molecules are those that are derived directly or indirectly from living beings (e.g., animals, plants, fruit, flowers, and the like). Naturally occurring molecules include products of naturally occurring molecules and synthetic molecules. Fragrant molecules can be found in food, wine, spices, perfumes, fragrance oils, and essential oils. For example, many form biochemically during ripening of fruits and other crops. In wines, most form as byproducts of fermentation.

Naturally occurring fragrant molecules include "essential" oils derived from plants. Essential oils are concentrated, hydrophobic liquids containing volatile fragrant molecules from plants. Essential oils are also known as volatile, ethereal oils or aetherolea, or simply as the "oil of" the plant from which they were extracted, such as, for example, oil of clove. An oil is "essential" in the sense that it carries a distinctive scent, or essence, of the plant. Essential oils do not have any specific chemical properties in common, beyond conveying characteristic fragrances. Some essential oils such as lavender, peppermint, and eucalyptus, are steam distilled. Raw plant material, comprising flowers, leaves, wood, bark, roots, seeds, or peel, are put into a distillation apparatus over water. As the water is heated the steam passes through the plant material, vaporizing the volatile compounds. The vapors flow through a coil where they condense back to liquid, which is then collected in the receiving vessel.

Essential oils are derived from berries, allspice, juniper, seeds, almond, anise, celery, cumin, nutmeg oil, bark, *cassia*, cinnamon, sassafras, wood, camphor, cedar, rosewood, sandalwood, agarwood, rhizome, galangal, ginger, leaves, basil, bay leaf, cinnamon, common sage, eucalyptus, lemon grass, melaleuca, oregano, patchouli, peppermint, pine, rosemary, spearmint, tea tree, thyme, wintergreen, resin, frankincense, myrrh, flowers, *cannabis*, chamomile, clary sage, clove, scented geranium, hops, hyssop, jasmine, lavender, manuka, marjoram, rose, rosemary, basil, lemon grass, ylang-ylang, peel, bergamot, grapefruit, lemon, lime, orange, tangerine, root, valerian, mango, or the like, or a combination comprising at least one of the foregoing.

Examples of fragrant molecules are alcohols (e.g., furaneol (strawberry), 1-hexanol (herbaceous, woody), cis-3-hexen-1-ol (fresh cut grass), menthol (peppermint), or the like, or a combination comprising at least one of the foregoing alcohols); aldehydes (e.g., acetaldehyde (pungent), hexanal (green, grassy), cis-3-hexenal (green tomatoes), furfural (burnt oats), or the like, or a combination comprising at least one of the foregoing aldehydes); esters (e.g., fructone (fruity, apple-like), hexyl acetate (apple, floral, fruity), ethyl methylphenylglycidate (strawberry), methyl formate, methyl acetate, methyl butyrate, methyl butanoate, ethyl acetate, ethyl butyrate, ethyl butanoate, isoamyl acetate, pentyl butyrate, pentyl butanoate, pentyl pentanoate, benzoin (extracted from resin of *styrax benzoin* tree); black pepper (from the plant piper nigrum of the piperaceae family), cajuput oil (from melaleuca cajuputi), caraway, carrot seed, coriander, cypress, dill, fennel, helichyrsum, lavandin, lemon verena, bee balm (lemon balm essential oil extracted from *melissa officinalis* of the labiatae family), niaouli, palmarosa, petitgrain, tagetes, vetiver, or the like, or a combination comprising at least one of the foregoing esters); ketones (e.g., dihydrojasmone (fruity woody floral), oct-1-en-3-one (blood, metallic, mushroom-like), 2-acetyl-1-pyrroline (fresh bread, jasmine rice), 6-acetyl-2,3,4,5-tetrahydropyridine (fresh bread, tortillas, popcorn), or the like, or a combination comprising at least one of the foregoing ketones); lactones (γ-decalactone (intense peach flavor), γ-nonalactone (coconut odor, popular in suntan lotions), δ-octalactone (creamy note, jasmine lactone powerful fatty fruity peach and apricot) massoia lactone (powerful creamy coconut, wine lactone sweet coconut odor) sotolon (maple syrup, curry, fenugreek), or the like, or a combination comprising at least one of the foregoing lactones); thiols (ethanethiol (commonly called ethyl mercaptan), grapefruit mercaptan (grapefruit), methanethiol (commonly called methyl mercaptan), 2-methyl-2-propanethiol (commonly called tertiary-butyl mercaptan)); linear terpenes (e.g., myrcene (woody, complex), geraniol (rose, flowery) nerol (sweet rose, flowery), citral, lemonal, geranial, neral (lemon, lemon myrtle, lemongrass), citronellal (lemon, lemongrass), citronellol (lemon, lemongrass, rose, pelargonium), linalool (floral, sweet, woody, lavender), nerolidol (woody, fresh bark), or the like, or a combination comprising at least one of the foregoing linear terpenes; cyclic terpenes (e.g., limonene, camphor, terpincol, ionone, thujuon, or the like, or a combination comprising at least one of the foregoing cyclic terpenes); aromatic species (e.g., benzaldehyde, eugenol, cinnamaldehyde, ethyl maltol, vanillin, anisole, anethole, estragole, thymol, or the like or a combination comprising at least one of the foregoing aromatic species); amines (e.g., thiethylamine, trimethylamine, cadaverine, pyridine, indole, skatole, or the like, or a combination comprising at least one of the foregoing amines) or the like, or a combination comprising at least one of the foregoing fragrant molecules.

Additional examples of fragrant molecules are geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenylcarbinyl acetate, p-tert-butyl-cyclohexyl acetate, isononyl acetate, vetiveryl acetate, vetiverol, alpha-n-amylcinammic aldehyde, alpha-hexylcinammic aldehyde, 2-methyl-3-(p-tert-butylphenyl)-propanol, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyletetrahydropyran, methyl-dihydrojasmonate, 2-n-heptylcyclopentanone, 3-methyl-2-pentylcyclopentanone, n-decanal, 9-decenol-1, phenoxyethyl isobutyrate, phenylacetaldehyde dimethyl acetal, phenylacetaldehyde diethyl acetal, geranonitrile, citronellonitrile, cedryl acetate, 3-isocamphycyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylioniones, irones, cis-3-hexenol and esters thereof, indane musk, tetralin musk, isochroman musk, macrocyclic ketones, macrolactone musk, ethylene brassylate, aromatic nitromusk.

Exemplary fragrant molecules include bergamot oil, coriander oil, dimethyl heptanol, dimethyl benzyl carbinyl acetate, geranyl acetate, citronellyl acetate, rose synthetic, geranium bourbon, hedione, iso eugenol, methyl eugenol styrallyl acetate, stemone, rose oxide laevo, aldehyde C-11 undecyclic, derivatives of 2,6-dimethyl-2-alkoxy octan-7-ol, vertivert oil, vetiverol, vetiveryl, acetate, quaiac wood oil, esters ol-anthranilic acid, benzyl salicylate, benzyl benzoate, oak moss, eugenol, p-tert-butyl cyclohexyl acetate and coumarin.

In an embodiment, an additional solvent may be used in the fragrant composition in addition to the ketal adducts of formula (1), specifically (1a). Polar solvents such as water, propylene carbonate, ethylene carbonate, butyrolactone, acetonitrile, benzonitrile, nitromethane, nitrobenzene, sulfolane, dimethylformamide, N-methylpyrrolidone, glycol ethers, methyl acetate, ethyl acetate, methanol, acetonitrile, nitromethane, ethanol, propanol, isopropanol, butanol, benzyl alcohol, butoxydiglycol, 1,2-propane diol (propylene glycol), 1,3-propane diol, ethoxydiglycol, hexylene glycol, and dipropylene glycol, triethylene glycol, hexylene glycol, diethylene glycol, ethylene glycol, propylene glycol, 1,2-butylene glycol or the like, or combinations comprising at least one of the foregoing solvents are generally desirable. Non-polar solvents such a benzene, toluene, methylene chloride, carbon tetrachloride, hexane, diethyl ether, hexane, tetrahydrofuran, or the like, or combinations comprising at least one of the foregoing non-polar solvents may also be used. Co-solvents comprising at least one polar solvent and at least one non-polar solvent may also be utilized to modify the compatibilizing capabilities of the solvent and thereby adjust the clarity and haze characteristics of the fragrant composition. Exemplary solvents are methyl acetate, ethyl acetate, glycol ethers, and water. Glycol ethers and alcohols can be used to compatibilize the ketal adducts of formula (1), specifically (1a) with water if desired. Exemplary solvents are water and ethyl alcohol.

In an embodiment, the fragrant composition can optionally comprise a radical scavenger or a source of a radical scavenger. As used herein the term radical scavenger refers to a species that can react with a carbonate radical to convert the carbonate radical by a series of fast reactions to a less reactive species, i.e., a carbonate radical scavenger.

Radical scavengers can be selected from the classes of alkanolamines, amino sugars, amino acids, esters of amino acids and mixtures thereof. For example, the following compounds can be employed as radical scavengers: ethylamine, monoethanolamine, 2-methoxyethylamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, morpholine, piperidine, or the like, or a combination comprising at least one of the foregoing radical scavengers.

The fragrant composition can optionally comprise a polymer. It is generally desirable for the polymer to be soluble in the ketal adducts of formula (1), specifically (1a) and/or in the cosolvent used with the ketal adducts of formula (1), specifically (1a). In an embodiment, the polymer is water-soluble. In another embodiment, the polymer is not water-soluble and exists as a dispersion in the fragrant composition.

It is desirable for the polymer to be an organic polymer. The polymer may be a thermoplastic, a thermosetting polymer, or a combination of a thermosetting polymer with a thermoplastic polymer. In an embodiment, the polymer may be an oligomer, a homopolymer, or a copolymer. The copolymer can be a block copolymer, a star block copolymer, a random copolymer, an alternating block copolymer, a dendrimer, an ionic block copolymer, a polyelectrolyte, or the like, or a combination comprising at least one of the foregoing polymers.

Examples of polymers that are water-soluble are polyvinyl alcohol, polyacrylamides, polyvinylpyrollidones, polyamides, hydroxyalkyl celluloses such as hydroxyethylcellulose and hydroxypropylcellulose, polyacrylic acid, or the like, or a combination comprising at least one of the foregoing water-soluble polymers.

Examples of polymers that are not water-soluble are polymethyl methacrylates, polyacrylates, polyesters, polyimides, polyethers, polyolefins, polyetherketones, polyether ether ketones, polyether ketone ketones, polycarbonates, polyarylene ethers, epoxies, polysulfones, polyethersulfones, polyetherimides, polynorbornylene, polysiloxanes, polyvinylchlorides, fluoropolymers, liquid crystalline polymers, ionomers, or the like, or combinations comprising at least one of the foregoing non-water-soluble polymers.

The polymers can be used as rheology modifiers, dispersants, stabilizers, promoters, or antimicrobials, and the like; in industrial product applications, such as, textiles (processing, finishing, printing, and dyeing aids, protective washable surface coatings, manufacture of synthetic leather by saturation of non-woven fabrics, and the like; manufacturing of woven fabrics, non-woven fabrics, natural and synthetic fibers and the like); water treatments (waste water, cooling water, potable water purification, and the like); chemical spill containments (acid-spill absorbent, and the like); leather and hide processing (processing aids, finishing, coating, embossing, and the like); paper and papermaking (surface coatings, such as pigmented coatings, antistatic coatings, and the like, pulp binders, surface sizings, dry and wet strength enhancers, manufacture of wet-laid felts, and the like); printing (inks, antiwicking ink-jet printer inks, thickeners for ink formulations containing cationic dyes for printing acrylic fabrics, and the like); paints (pigment and grinding additive, crosslinking agent for epoxy latex emulsions, particulate-suspending aid for clays, pigments, and the like); industrial plant effluent treatment (flocculants for phenolics in paper mill effluent, and the like); metal working (acid etch cleaners, low pH metal coatings, pickling agents in cold rolled steel processing, and the like); adhesives (clear adhesives, adhesion promoters for metal, plastic, wood, and the like, non-woven floc adhesive tie coatings, bonding, and the like); wood preservation; and industrial construction products for buildings and roads (cement plasticizers, asphalt emulsion stabilizers at low pH, acid etch for cement, consistency modifiers of concrete, mortar, putty, and the like).

The polymer has a number average molecular weight of less than or equal to about 1,000,000 grams per mole, specifically less than or equal to about 500,000 grams per mole, specifically less than or equal to about 50,000 grams per mole, and more specifically less than or equal to about 5,000 grams per mole.

Other additives may also be added to the fragrant composition to form a fragrant composition. These additives are optional. Suitable additives are antioxidants, antiozonants, antibacterial agents, humectants, colorants, dyes, pigments, food additives, pheromones, musks, a carbonate ion source, an alkalizing agent, a pH buffer, a conditioning agent, a chelant, an auxiliary agent, solvents (e.g., a cosolvent), surfactants (as cleansing agents, emulsifying agents, foam boosters, hydrotropes, solubilizing agents, and suspending agents), nonsurfactant suspending agents, emulsifiers, skin conditioning agents (emollients, humectants, moisturizers, and the like), hair conditioning agents, hair fixatives, film-formers, skin protectants, binders, chelating agents, antimicrobial agents, antifungal agents, antidandruff agents, abrasives, adhesives, absorbents, dyes, deodorant agents, antiperspirant agents, opacifying and pearlescing agents, preservatives, propellants, spreading aids, sunscreen agents, sunless skin tanning accelerators, ultraviolet light absorbers, pH adjusting agents, botanicals, hair colorants, oxidizing agents, reducing agents, skin bleaching agents, pigments, physiologically active agents, anti-inflammatory agents, topical anesthetics, fragrance and fragrance solubilizers, a polymer, and the like, in addition to ingredients previously discussed that may not appear herein. Oral care products, for example, can contain anticaries, antitartar, and/or antiplaque agents in addition to surfactants, abrasives, humectants, flavorants, or the like, or a combination comprising at least one of the foregoing additives.

In an embodiment, in one method of manufacturing the fragrant composition, a fragrant composition, the ketal adducts of formula (1), specifically (1a) as described above, an optional solvent, an optional active agent, an optional surfactant, an optional thickening agent, an optional compatibilizer and desired additives are blended together in the desired quantities in a reactor. The reactor may be a batch or continuous reactor. It is desirable for the reactor to be fitted with a mechanism for agitating the fragrant composition. The fragrant composition may be heated if desired to evaporate some solvent or to further drive compatibilization between the fragrant compositions, the ketal adducts of formula (1), specifically (1a) and the optional solvent.

In another embodiment, in another method of manufacturing the fragrant composition, the ketal adducts of formula (1), specifically (1a) may be used as an extraction solvent to extract a fragrant composition such as essential oils from naturally occurring substances. The ketal adducts of formula (1), specifically (1a) may be retained with the essential oil and further processed to form a desired fragrant composition. The essential oils can be extracted via steam extraction, supercritical extraction or solvent extraction. The ketal adducts of formula (1), specifically (1a) can be used in conjunction with steam, supercritical solvents, or normal solvents (solvents that are not in a supercritical state) to effect extraction of essential oils. The ketal adducts of formula (1), specifically (1a) can also be used by itself to extract essential oils.

Steam extraction is normally environmentally friendly and uses only water to effect the extraction. Water is not however, a good solvent for all essential oils. The ketal adducts of formula (1), specifically (1a) can be used in conjunction with water to extract additional essential oil from a naturally occurring substance than that which would be extracted by using only steam for the extraction. The use of the ketal adducts of formula (1), specifically (1a) in steam extraction would continue to render the process environmentally friendly, while at the same time being effective to extract additional oil from the naturally occurring substance.

Supercritical extraction is generally conducted with carbon dioxide, but can also be effected with other solvents. A blend of supercritical carbon dioxide and the ketal adducts of formula (1), specifically (1a) can be used to extract essential oils for the fragrant composition. Liquid carbon dioxide (that is not in a supercritical state) blended with the ketal adducts of formula (1), specifically (1a) can also be used for extraction. Other supercritical fluids can also be blended with the ketal adducts of formula (1), specifically (1a) to extract essential oils.

Hexane extraction is generally used to extract a variety of essential oils. The ketal adducts of formula (1), specifically (1a) can be blended with the hexane (or other solvents) to facilitate improved extraction. Ethanol is often used to target the segregation of a target molecule from hexane after extraction. In an embodiment, while the ketal adducts of formula (1), specifically (1a) is used to facilitate the extraction of an essential oil in conjunction with hexane, it can also be used to facilitate a segregation of a target molecule from the hexane. By changing the ratio of the amount of the ketal adducts of formula (1), specifically (1a) in the mixture of the target molecule and hexane and/or temperature, the target molecule can be segregated after the extraction. Other solvents can be used in conjunction with the ketal adducts of formula (1), specifically (1a) to facilitate segregation of the target molecule.

In yet another embodiment, the ketal adducts of formula (1), specifically (1a) by itself can be used to facilitate an extraction of various essential oils from naturally occurring substances. The ketal adducts of formula (1), specifically (1a) can be blended with the naturally occurring substance and under suitable combinations of temperature and pressure can facilitate the extraction of an essential oil from the naturally occurring substance. The resulting product can then be subjected to purification processes such as filtration, decantation, distillation, and the like to obtain a purified mixture of the essential oil and the ketal adducts of formula (1), specifically (1a). The mixture of the essential oil and the ketal adducts of formula (1), specifically (1a) can then be blended with other suitable ingredients to produce the desired fragrant composition. Thus the ketal adducts of formula (1), specifically (1a) may be used not only to extract the essential oil but can serve as a solubilizing solvent and/or a fixative in the fragrant composition.

The blending to form the fragrant composition or the fragrant composition may be conducted via dry blending, melt blending, solution blending, or a combination comprising at least one of the foregoing forms of blending. Dry blending encompasses blending without the use of solvents and is generally conducted to blend two or more fragrant compositions. Melt blending occurs when the temperature of blending is conducted above the melting point of some of the ingredients and wet blending is generally conducted in the presence of solvents.

The blending of the formulation involves the use of shear force, extensional force, compressive force, ultrasonic energy, electromagnetic energy, thermal energy or combinations comprising at least one of the foregoing forces or forms of energy and is conducted in processing equipment wherein the aforementioned forces are exerted by a single screw, multiple screws, intermeshing co-rotating or counter rotating screws, non-intermeshing co-rotating or counter rotating screws, reciprocating screws, screws with pins, barrels with pins, rolls, rams, helical rotors, or combinations comprising at least one of the foregoing.

Blending involving the aforementioned forces may be conducted in machines such as single or multiple screw extruders, Buss kneader, Henschel, helicones, Ross mixer, Banbury, roll mills, molding machines such as injection molding machines, vacuum forming machines, blow molding machine, kettles, kettles with distillation and/or condensation columns, or then like, or combinations comprising at least one of the foregoing machines.

The fragrant composition may be used in a variety of articles and applications. It may be used in body lotions, shampoos, massage oils, as a chemical identifier (e.g., in non-smelling chemicals or in toxic or hazardous chemicals), to mask odor, in perfume sticks and lanterns, air fresheners, candles, paints, varnishes, furniture, insect repellents, in polymers, cleaners, detergents, cosmetics, toiletries, cosmeceuticals and beauty aids, personal hygiene and cleansing products applied to the skin, hair, scalp, and nails of humans and animals. The fragrant compositions are used in a variety of air fresheners such as for example, spray, gel (e.g., an electric air freshener or beads), a paper substrate (e.g., car air fresheners hanging from rearview mirrors) or liquid (e.g., reed diffusers or with electric air fresheners).

The term "health care products" as used herein includes pharmaceuticals, pharmacosmetics, oral care products (mouth, teeth), eye care products, ear care products and over-the-counter products and appliances, such as patches, plasters, dressings and the like, and medical devices externally applied to or into the body of humans and animals for ameliorating a health-related or medical condition, for generally maintaining hygiene or well-being, and the like. The term "body" includes the keratinous (hair, nails) and non-keratinous skin areas of the entire body (face, trunk, limbs, hands and feet), the tissues of body openings and eyes, and the term "skin" includes the scalp and mucous membranes. The term "household care products" as used herein includes products employed in a domestic household for surface cleaning, odor control or masking, or biocidal cleaning products for maintaining sanitary conditions, such as in the kitchen and bathroom, laundry products for fabric care and cleaning, air fresheners, air sanitizers, air deodorizers/odor removers, candles, and the like. These products can be used in the home, in the workplace, or in institutional settings.

The fragrant composition or fragrant composition is generally added as a concentrate to an article to produce a desired sensory effect in the article. The ratio of the fragrant composition to the ketal adducts of formula (1), specifically (1a) used in the fragrant composition may vary from article to article depending upon the composition of the article. In addition, the amount of the fragrant composition may also vary from article to article depending upon the utility of the article.

In an embodiment, the fragrant composition may be added to organic polymer formulations to impart to the organic polymer a particular odor or in order to mask an undesirable odor. Examples of polymers to which the fragrant composition can be added are polyolefins, polyvinyl acetates, polystyrenes cellulose acetates, acrylonitrile butadiene styrene, polyacrylics, polycarbonates, polyamides, polyurethanes, epoxies, and polyesters.

The ketal adducts of formula (1), specifically (1a) are also useful in personal care compositions. As used herein, personal care compositions have a broad scope and include cosmetic (i.e., make-up) compositions. Exemplary personal care compositions include bath or shower products, including various hair and body cleaners; eye care products; cosmetics; a fragrance; treatment formulation, including a hair coloring formulation; a hair straightening or permanent wave formulation; a nail care formulation; an oral hygiene formulation, including toothpaste and mouthwash; a shave cream; a skin care formulation; a sun care formulation; a lip care formulation; an antiperspirant; or a foot care formulation. Personal care compositions are used interchangeably with personal care formulations. It is appreciated that some personal care compositions such as hand cleaning and body cleaning formulations also fall under the scope of cleaning compositions disclosed herein.

The ketal adducts of formula (1), specifically (1a) can be used to enhance the solubility of an active agent in a personal care formulation. Depending on the native solubility of the active agent in the formulation and the type of formulation, the ketal adducts of formula (1), specifically (1a) can be used as a cosolvent with water, as a compatibilizer with water and an organic solvent, as a cosolvent with an organic solvent, as an emulsifier, or a combination comprising of any of one or more of the foregoing. As is known to those of skill in the art of formulating personal care products, an individual ingredient can have more than one type of function, for example the ketal adducts of formula (1), specifically (1a) could function both as a cosolvent and as a compatibilizer.

The presence of such a ketal adduct can allow the concentration of the active agent to be increased, often without the presence of volatile organic compounds (VOCs) such as ethanol, isopropanol, acetone, ethyl acetate, and the like in the formulation, or with reduced amounts of these VOC's. The result in some cases can be a more concentrated low VOC formulation. The ketal adducts of formula (1), especially (1a) can also perform additional functions, such as compatibilization, or solubilization of certain organic materials into an oil phase, and emulsification of an oil phase into an aqueous phase.

The ketal adducts of formula (1), specifically (1a) can act as an emulsifier, compatibilizer, or solubilizer for ingredients other than the active agent, or as a co-emulsifier, co-compatibilizer, or co-solubilizer for ingredients other than the active agent. Moreover, incorporation of the ketal adducts of formula (1), specifically (1a) can lead to a lighter, less greasy or heavy-feeling formulation, especially compared to many other naturally-derived ingredients.

In cases in which the active agent is somewhat soluble or highly soluble in an alcohol or alcohol-water mixture, the ketal adducts of formula (1), specifically (1a) can in some cases function as a cosolvent, either with the alcohol or with an alcohol-water mixture. The ketal adducts of formula (1), specifically (1a) can in some cases permit an increase in the concentration of the active agent in an alcoholic or alcohol-water phase. In other cases, it can permit the proportion of the alcohol in the cosolvent mixture to be decreased, which has the benefit of reducing VOCs in the formulation and in some cases decreasing the drying effect the formulation has on the skin. In some cases, the ketal adducts of formula (1) specifically (1a) can also lead to a lighter, less greasy or heavy-feeling formulation.

In formulations containing active agents that are oil or oil-soluble and sparingly (if at all) soluble in water, the ketal adducts of formula (1), specifically (1a) can in some cases permit the active agent to become dissolved in an aqueous phase and in other cases in conjunction with one or more other cosolvents. In some cases, a mixture of ketal adducts having different solubility/solubilizing characteristics can be present in order to accomplish the dissolution of the active agent. Alternatively (or in addition), the ketal adducts of formula (1), specifically (1a) can aid in dissolving or compatibilizing such an active agent into an organic phase, or to help compatibilize or emulsify an organic phase containing the active agent with an aqueous phase, forming in this case an emulsified formulation that can be, for example, a cream or lotion. As before, the ketal adducts of formula (1), specifically (1a) in some cases can allow the level of emollient materials to be reduced or improve formulation feel characteristics.

Whether an active agent is present or not, the ketal adducts of formula (1), specifically (1a) can in some cases aid mutually incompatible materials to be formulated into a stable formulation form. Thus, the ketal adducts of formula (1), specifically (1a) is a valuable ingredient in many emulsified formulations, such as lotions and creams, which include a water-in-oil or oil-in-water emulsion. In many cases, this can be achieved while reducing or eliminating other ingredients from the formulation. For example, volatile organic compounds or emulsifiers can be eliminated or used in reduced quantities. The presence of the ketal adducts of formula (1), specifically (1a) can improve the feel of a personal care, giving the formulated formulation a lighter, less oily feel while preserving its function and performance. In many cases, formulation viscosity is reduced, which can contribute to the lighter and less greasy feel.

Because the ketal adducts of formula (1), specifically (1a) is a good solvent for a wide range of materials, it is very useful for making concentrates, which can be let down into an oil, an alcohol or other diluent to provide a personal care composition.

In one aspect, the personal care composition contains the ketal adducts of formula (1), specifically (1a), and one or more active agent selected from organic anti-aging agents, organic anti-acne agents, organic skin whitening agents, organic ultraviolet light absorbing agents, organic tanning agents, organic anti-alopecia agents, antifungal agents and/or anti-dandruff agents, antimicrobial agents, organic medicinals, depilatory compounds, hair dyes, or organic insect repellants. In some embodiments, the ketal adducts of formula (1), specifically (1a) forms part of a cosolvent mixture with water, with oils, or with another organic solvent miscible with the ketal adducts of formula (1), specifically (1a) at the relative proportions thereof that are present in the formulated personal care formulation, and the active agent is dissolved in the cosolvent mixture. The active agents are present in amounts effective to achieve the desired activity, which can vary broadly, depending on the active agent and the product. Thus, an active agent can be present in the formulation in amounts as low as 0.001 wt. %, 0.01 wt. %, or 0.1 wt. %, up to 30 wt. %. The amount of water used in the formulation can also vary widely based on the active agent and the product, from anhydrous products as described above, to products have from 2 to 90%, 80%, 70%, 60%, 50%, 40%, 30%, 20%, or 10 wt. % water, based on the total weight of the formulation.

Thus, in some embodiments, the formulated personal care formulation includes a compound selected from alpha-hydroxy acids such as lactic acid, 2-hydroxydecanoic acid, 2-hydroxyoctanoic acid and glycolic acid, beta-hydroxy acids such as beta-hydroxy salicylic acid, avobenzone, coenzyme Q10, benzoate-4-methylbenzylidene, cinoxate, dioxybenzone, homosalate, menthyl anthranilate, mexoryl SX, drometrizole trisiloxane, octocrylene, octyl methoxycinnamate, ethylhexyl salicylate, oxybenzone, padimate O, p-aminobenzoic acid (PABA), phenylbenzimidazole sulfonic acid, sulisobenzone, titanium trolamine salicylate, salicylic acid, retinoic acid (including the all-trans isomer known as tretinoin), benzoyl peroxide, hydroquinon, arbutun (including plant extracts containing same), kojic acid, azelaic acid, glycyrrhetic acid, levulinic acid, 2-cyano-3,3-diphenylacrylic acid, sodium benzotriazolyl butylphenol sulfonate, ethyl-2-cyan-3,3-diphenylacrylate, 2-t-butyl-6-(5-chloro-2H-benzotriazol-2-yl)-p-cresol, 2-(2-H-benzotriazol-2-yl)-4-methylphenol, benzophenone-12, bornelone, or 2-benzotriazolyl-4-tert-octylphenol. These compounds function as anti-aging, anti-acne, skin whitening and/or UV absorbers; formulations containing them are useful as anti-aging or anti-wrinkle formulations, acne treatments, skin whiteners, and/or sunscreens.

In some embodiments, a personal care formulation includes a tanning agent such as dihydroxyacetone, erythrulose, dihydroxyacetone-ortho-ethyl-acetate, canthaxanthin, or afamelanotide. These compounds function as tanning agents, and personal care formulations containing them in sufficient quantities are effective tanning (skin darkening) formulations.

In some embodiments, the personal care formulation includes a compound selected from minoxidil and 5-alpha reductase inhibitors such as dutasteride and ketoconazole. These compounds function as anti-alopecia (hair loss prevention) agents; accordingly, personal care formulations containing them are useful in some cases to prevent hair loss.

In some embodiments, a personal care formulation includes a compound selected from zinc pyrithione, selenium sulfide, clotrimazole, tea tree oil, or piroctone olamine. These compounds function as anti-fungal agents, and personal care formulations containing them in sufficient quantities are effective topical anti-fungal treatments (such as for Tinea pedis or Tinea cruris) and/or as anti-dandruff formulations.

In some embodiments, a personal care formulation includes a compound selected from an amphetamine, an antihistamine, methylphenidate, oxymetazoline, tetrahydrolzoline hydrochloride, or psilocybin. These compounds function as vasoconstrictors in some instances and personal care formulations containing them in sufficient quantities are effective as redness reducers (such as in eye drops and anti-redness or anti-puffing creams).

In some embodiments, a personal care formulation includes a compound selected from calcium thioglycolate, sodium thioglycolate, thioglycolic acid, ammonium thioglycolate, butyl thioglycolate, ethanolamine thioglycolate, glyceryl thioglycolate, isooctyl thioglycolate, isopropyl thioglycolate, magnesium thioglycolate, methyl thioglycolate, or potassium thioglycolate. These compounds function to modify hair fibers by breaking S—S bonds in keratin; personal care formulations containing them in sufficient quantities are used in depilatories, permanent waves, relaxers, hair straightening, and hair re-styling formulations.

In some embodiments, a personal care formulation includes a compound selected from aluminum zirconium tetrachlorohydrex gly, aluminum chlorohydrate, or aluminum chloride. These agents are anti-perspirants and personal care formulations containing these are often effective as deodorants and anti-perspirants.

In some embodiments, a personal care formulation includes a compound selected from resorcinol ("resorcin"), 1-napthol, p-aminophenol, p-phenylenediamine (and its salts), 4-amino-2-hydroxytoluene, and the like. These active agents are effective hair dyes; and personal care formulations containing these are often effective as hair colorants or hair colorant concentrates.

In some embodiments, a personal care formulation includes a compound selected from phenoxyethanol, N,N-diethyl-m-toluamide, p-menthane-3,8-diol (active agent in the essential oil of lemon eucalyptus), nepetalactone (catnip oil), citronella oil, permethrin, neem oil, or bog myrtle extract. These active agents are effective insect repellants; and personal care formulations containing these are often effective as insect repellants.

In some embodiments, the personal care formulation comprises from 0 or 0.001 to 15 wt. % water, specifically, 0 or 0.01 to 12 wt. % water, 0.1 to 10 wt. % water, 0.5 to 8 wt. % water, or 1 to 5 wt. % water, each based on the total weight of the formulation. In some embodiments, the personal care formulation is essentially anhydrous, containing no more than 3 wt. % water, no more than 2 wt. % water, more specifically no more than 1 wt. % water. In essentially anhydrous personal care formulations, the amount of water can be 0%, as low as 0.001%, or 0.01%, or 0.1 wt. %, each based on the total weight of the personal care formulation.

In another aspect, for use in a waxy formulation, e.g., a lipstick, lip gloss, lip balm formulation, or a cuticle cream, that contains a wax, an emollient, and the ketal adducts of formula (1) specifically (1a) is provided. In embodiments of particular interest, the lipstick, lip gloss, lip balm, or cuticle cream formulation contains from 0.1 to 10 wt. % water, specifically 0.5 to 5 wt. % water, each based on the total weight of the persona care formulation. These formulations are in stick or other solid form. In another aspect, a formulated personal care formulation in the form of an emulsion is provided. The emulsion can have a continuous phase and a disperse phase, one of which is an aqueous phase, and the other of which is an oil phase. Alternatively, the emulsion can have at least two co-continuous phases, again wherein at least one of the co-continuous phase is an aqueous phase and at least one of the co-continuous phases is an oil phase. The oil phase contains at least one of (a) a paraffinic, naphthenic or aromatic mineral oil, or a seed oil (b) a nonionic organic compound having a melting temperature of less than 45° C., a molecular weight of at least 190 Daltons, an amido or ester group, an alkyl chain containing at least 8 carbon atoms, and a solubility in water of no greater than 1 part in 99 parts of water by weight; (c) a nonionic organosilicone compound having a melting temperature of less than 45° C. and a solubility in water of no greater than 1 part in 99 parts of water by weight; (d) a long chain alcohol; and (e) a wax. The emulsion further comprises the ketal adducts of formula (1), specifically (1a). The ketal adducts of formula (1), specifically (1a)) can be present in a continuous phase, a disperse phase, in both a continuous phase and a disperse phase, or at the interface between a continuous and a disperse phase. Additional ingredients can also include emollients such as vegetable oils and animal fats and derivatives thereof; nonionic organosilicone compounds such as dimethicone and cyclopentasiloxane; cosolvents as described herein above; natural, synthetic, or modified organic polymers; surfactants as described herein above; natural or synthetic fragrances; botanical extracts; natural or synthetic dyes; pigments or pearlizers; pH adjusters/buffers and chelating agents; inorganic particulates; non-hydrocarbon propellants; preservatives, and a combination comprising at least one of the foregoing.

Personal care formulations and products can take the physical form of solids (sticks, bars, powders, etc.), solutions (including solutions containing sufficient gallant or thickener to provide a gel-like consistency), ointments, dispersions (including pastes or scrubs), or emulsions (including gels, liniments, lotions, creams, or the like). They can be sprayable, in particular the solutions, dispersions, and powders.

Many personal care formulations are combinations of two or more of formulation forms. For example, some personal care formulations contain an aqueous phase that contains a dissolved active agent, and further includes an oil phase which can be present, for example, to supply emollients and/or humectants, or to produce a specific formulation form (cream, lotion and the like). In such cases, it is possible to include two or more ketal adducts within the formulation to perform different functions. Thus, for example, a fully-water-miscible ketal adduct might be present in the aqueous phase to help dissolve the active agent, and a partially- or sparingly water-miscible ketal adduct might be present within the oil phase to reduce its viscosity or compatibilize its components. Either of these ketal adducts can also perform some emulsifying or compatibilizing function between the aqueous and oil phases.

In addition, the ketal adducts of formula (1), specifically (1a) can perform multiple functions within a personal care formulation, such as dissolving an active agent into an aqueous or oil phase, compatibilizing, or emulsifying an aqueous phase with an oil phase.

The ketal adducts of formula (1), specifically (1a) can reside in an aqueous phase, in an alcoholic or alcohol-water phase, or in an oil phase of a personal care formulation, depending on the particular formulation and the particular ketal adduct. In many cases, the ketal adducts of formula (1), specifically (1a) can become distributed between aqueous and oil phases of a personal care formulation, due to its solubility in both phases. In some cases, the ketal adducts of formula (1), specifically (1a) can reside at the boundary of aqueous and oil phases.

The amount of the ketal adducts of formula (1), specifically (1a) present in a personal care formulation depends on the function of the ketal adducts of formula (1), specifically (1a), the other ingredients of the personal care formulation, the specific form of the personal care formulation, and like considerations. In general, the formulation comprises 0.001 to 90 wt. %, 0.01 to 80 wt. %, 0.1 to 70 wt. %, or 0.1 to 50 wt. % of the ketal adducts of formula (1), specifically (1a) based on the total weight of the formulation, although a more typical amount is from 0.5 to 25 wt. %, and in many cases from 1 to 10 wt. % the total formulation weight.

Anti-aging, anti-acne, skin whitening and sun protection formulations can contain 0.001 to 50 wt. % of the active agent, specifically from 0.01 to 40 wt. %, based on the total weight of the formulation. Anti-aging and anti-acne formulations can be formulated into aqueous and/or ethanolic solutions, or into lotions or creams. Sun protection formulations can take the form of clear, low viscosity liquids (as is typical for spray-on formulations, which are often ethanolic or ethanol-water based), or else are lotions or creams. Spray-on sun protection formulations can be aqueous and/or ethanolic solutions or dilute emulsions. Many of the anti-aging, anti-acne, skin whitening and sun protection active agents are soluble to the extent of at least 5 parts per 95 parts of the ketal adducts of formula (1), specifically (1a) in the formulation. These include, for example, avobenzone, coenzyme Q10, hydroquinone, oxybenzone, and salicylic acid, all of which are soluble to the extent of at least 5 parts per 95 part of the ketal adducts of formula (1), specifically (1a). In these cases, the presence of the ketal adducts of formula (1), specifically (1a) often allows the amount of ethanol to be reduced, and/or the amount of active agent to be increased at a constant ethanol content, leading to a formulation which is less drying to the skin. In some cases, the ketal adducts of formula (1), specifically (1a) can be used to replace a heavy-feeling material that solubilizes the active.

An anti-aging, anti-acne, skin whitening, or sun protection formulation can contain additional UV absorbing agents, notably inorganic compounds such as titanium dioxide or zinc oxide. These materials are solid particles that typically are dispersed into a lotion or cream formulation.

Sun protection formulations such as sunscreens often contain a mixture of organic UV absorbing agents, often in order to broaden the range of wavelengths of UV light that are absorbed. Such mixture of organic UV agents can include two or more of avobenzone, octylmethoxyl cinnamate, oxybenzone, and ethylhexyl salicylate. These may, in the aggregate, constitute from 0.1 to 50% of the weight of the sunscreen formulation, and more specifically constitute from 2 to 25 wt. % thereof.

A tanning formulation can contain 1 to 25 wt. %, for example 2 to 10 wt. %, of one or more tanning agents as described before. Tanning formulations often are formulated into a lotion or a cream. Spray-on tanning formulations can be aqueous and/or ethanolic solutions.

A tanning formulation can contain organic UV active agents, as described before, as well as inorganic UV active agents such as titanium dioxide or zinc oxide. As is the case with sunscreen formulations, organic UV active agents can constitute from 0.1 to 50 wt. %, specifically 0.1 to 30 wt. % of the weight of a tanning formulation, and more specifically from 2 to 25 wt. % thereof A mixture of organic UV additives can be present, including a mixture of two or more of avobenzone, octylmethoxyl cinnamate, oxybenzone, and ethylhexyl salicylate.

Anti-dandruff formulations can contain from 0.1 to 25 wt. %, specifically from 0.5 to 10 wt. % of one or more of an anti-fungal agent as described before. The formulation form can be an aqueous solution, aqueous gel, or dilute emulsion containing mostly aqueous phase. An anti-dandruff formulation can contain one or more surfactants, particularly one or more anionic surfactants. Sulfosuccinate, lauryl sulfate, and laureth sulfate surfactants and the various fatty acid betaines, or fatty acid amide propyl betaines are preferred types, although others, particularly other anionic surfactants, can be used. Surfactants can constitute from 0.1 to 10 wt. % an anti-dandruff formulation. The surfactants can function as cleaning agents and/or emulsifiers in the formulation. An anti-dandruff agent can contain hair conditioners and other materials as well.

Anti-alopecia formulations can contain 0.1 to 25 wt. %, for example 1 to 10 wt. % of one or more of anti-alopecia agents. Formulations of these types typically are formulated into low to medium viscosity fluids, which can contain a propellant and be sprayable, which can be clear solutions in the case of anti-alopecia formulations or opaque emulsions in the case of anti-dandruff formulations. These formulations can contain propylene glycol, ethanol, and/or water as a cosolvent mixture, although an advantage of this invention is that levels of propylene glycol and/or ethanol can in some cases be reduced due to the presence of the ketal adducts of formula (1), specifically (1a).

Chemical treatment formulations for hair include hair straighteners, relaxers, and/permanent wave formulations can contain one or more materials which straighten hair, possibly by breaking sulfur-sulfur bonds in keratin or some other component of hair; among these are the depilatory agents described before. They can constitute up to 10 wt. % of a chemical treatment active agent for hair. Chemical treatment formulations for hair can take the form of low viscosity fluids, lotions, creams, or gels.

A hair styling formulation can contain one or more hair fixatives, which hold the hair into a re-styled position. Some of these fixatives can also function as thickeners in a hair straightening and styling formulation. The hair fixative can be 0.25 to 25 wt. %, for example 0.5 to 15 wt. % of the formulation. The hair styling formulation can take the form of an aqueous and/or ethanolic solution, a gel, or a lotion.

Anti-perspirant formulations contain one or more anti-perspirant agents such as described before. Anti-perspirant formulations can take the form of a gel, a viscous liquid (for roll-on applications), or a stick.

A stick or roll-on anti-perspirant can contain some water, which can constitute from 2 to 60% of the weight of the formulation, and at least 5%, up to 30 wt. % the anti-perspirant agent.

A topical medicinal formulation can contain one or more medicinal agents such as an amphetamine, antihistamine, methylphenidate, oxymetazoline, tetrahydrolzoline hydrochloride, psilocybin, clotrimazole, tea tree oil, piroctone olamine, chlorhexidine, octenidine, triclosan, sodium 3,5-dibromo-4-hydroxybenzenesulfonate (Dibromol), quaternary ammonium salts such as benzalkonium chloride, cetyl trimethylammonium bromide, cetylpyridinium chloride, and benzethonium chloride, and the like. These formulations can be formulated into low viscosity fluids (which can be sprayable), gels, lotions, creams, liniments, or ointments. Low viscosity fluid formulations can be aqueous and/or ethanolic; lotions and creams can be emulsions containing an aqueous continuous phase and a dispersed or co-continuous phase that contains an emollient.

Hair dye formulations can include hair dyes such as those described above. Hair bleaching formulations can contain a peroxy-type bleaching agent such as hydrogen peroxide in an effective amount, for example 0.1 to 5 wt. % of the total weight of the formulation in the case of dyes; and 1 to 20 wt. % in the case of bleaches. A bleaching formulation can in addition contain an inorganic oxidant such as a persulfate salt, in an amount of 0.1 to 5 wt. % of the formulation. Hair dye and bleaching formulations can take the form of low viscosity fluids, lotions, creams, or gels. They can also be prepared in a water-dilutable concentrate form. A hair dye or bleaching formulation can contain one or more surfactants which can function to stabilize the emulsion, or as a detergent.

Depilatory formulations can contain one or more depilatory agents such as those described before, for example in an amount of 1 to 20 wt. %, based on the weight of the formulation. Depilatory formulations can be in the form of lotions, creams, or gels.

In another aspect, a waxy solid formulation that contains a wax, an emollient, and the ketal adducts of formula (1), specifically (1a) is provided. The waxy solid formulation can contain from 0.5 to 20 wt. %, 15 wt. %, 10 wt. %, 8 wt. %, 5 wt. %, 4 wt. %, or 3 wt. % water. These formulations can be provided in stick or other solid form. They can contain at least 20 wt. % of an oil such as castor oil, a wax (as defined below) and at least 0.5 wt. % the ketal adducts of formula (1), specifically (1a). The ketal adducts of formula (1), specifically (1a) can be present in an amount up to 25 wt. %, 20 wt. %, 15 wt. %, or 10 wt. % the formulation. The ketal adducts of formula (1), specifically (1a) can be a partially or fully water-miscible ketal adduct, as defined below, when the waxy solid formulation contains more than 0.5 wt. % water. Such formulations include lip formulations such as a lipstick, lip gloss, or lip balm; cuticle creams; and the like.

Many waxy formulations, including lip care formulations include a mixture of one or more waxes with one or more oils and, in the case of lipsticks, one or more pigments. Lipsticks and lip balm formulations, as well as cuticle creams, tend to be malleable solids at 25° C., whereas lip glosses tend to be viscous liquids or pastes. A lip care formulation can contain, for example, from 1 to 30 wt. % of a wax; from 30-95 wt. % of one or more other hydrophobic materials, of which castor oil is typically an important component; and from 1 to 30 wt. % of one or more pigments. In some embodiments, the lipstick or lip balm formulation contains a ketal adduct of formula (1) In addition to the foregoing active agent-containing personal care formulations, a significant number of personal care formulations do not contain any of the foregoing active agents, but nonetheless exist in the form of emulsions. The emulsions can be water-in-oil types, oil-in-water types, or types containing co-continuous aqueous and oil phases. These formulations typically take the form of low viscosity fluids (in which the disperse phase, which is typically an oil phase, constitutes a small proportion, typically 35% or less or 10% or less by weight of the formulation), lotions, or creams. These formulations include, for example, hair conditioners, after-shave lotions, various body cleansers, various hand and skin lotions and creams and the like, which do not contain specific active agents as described above. Emulsion formulations of these types typically contain from 0.1 to 50 wt. % the ketal adducts of formula (1).

Additional ingredients that can be included in the personal care formulations of this disclosure include paraffinic, naphthenic, or aromatic mineral oil; a nonionic organic compound having a melting temperature of less than 45° C., a molecular weight of at least 190 Daltons, an amido or ester group, and an alkyl chain containing at least 8 carbon atoms, and a solubility in water of no greater than 1 part in 99 parts of water; a nonionic organosilicone compound having a melting temperature of less than 45° C., and a solubility in water of no greater than 1 part in 99 parts of water; a long chain alcohol (eight or more carbon atoms), a wax, or a combination comprising at least one of the foregoing. Additional ingredients can also include emollients such as vegetable oils and animal fats and derivatives thereof; nonionic organosilicone compounds such as dimethicone and cyclopentasiloxane; cosolvents as described herein above; natural, synthetic, or modified organic polymers; surfactants as described herein above; natural or synthetic fragrances; botanical extracts; natural or synthetic dyes; pigments or pearlizers; pH adjusters/buffers and chelating agents; inorganic particulates; non-hydrocarbon propellants; preservatives, and a combination comprising at least one of the foregoing.

Formulations containing ketal adduct of formula (1) have been found to be excellent cosmetic (make-up) removers, particularly if the formulation contains at least 5 wt. % and more specifically at least 8 wt. % the ketal adduct. The ketal adduct can constitute up to 75 wt. %, up to 60 wt. % or up to 50 wt. % of the weight of a cosmetic remover formulation. A cosmetic remover in can include, in addition to the ketal adduct, water, an alcohol such as ethanol, isopropanol or 1,2- or 1,3-propane diol; one or more of components above. Such a cosmetic remover can even be free of surfactants, or contain low (less than 2 wt. %) concentrations of surfactants.

The ketal adducts of formula (1), especially (1a), are also efficient solvents for polymers that are generally present in nail polishes, such as nitrocellulose, cellulose acetate propionate, cellulose acetate butyrate, styrene/acrylates copolymers, acrylates copolymers, polyethylene terephthalate and tosylamide/formaldehyde resins and thus find benefit as solvents in nail polish removers, nail strengthening formulations, and/or nail polishes.

The personal care formulations described herein satisfy certain continuing needs in the art for formulary ingredients. The ketal adducts of formula (1), especially (1a) can be used in a wide range of formulation forms and in a wide variety of specialized applications. Although these various types of formulations differ enormously, as do the conditions under which they are used, the ketal adducts of formula (1), especially (1a), can be used in the formulation of many of them, which greatly simplifies the formulation process.

In addition, formulating personal care formulations must often simultaneously address formulation needs that are often competing and sometimes even contradictory. For example, many personal care formulations contain an active agent that lends a particular functional attribute to the formulation. It can be desirable to increase the concentration of the active agent in a given formulation, or to produce a formulation that contains the active agent in a specific formulation form (such as a solution, dispersion, lotion, cream, stick, gel, or the like), but the formulator is limited by the solubility of the active agent in the other ingredients in the formulation. Approaches to address solubility include the use of various types of emulsifiers, oils, cosolvents, and the like, but it is often the case that other requirements, such as the specific formulation form, are incompatible with the presence of such materials in the amounts needed for efficacy. Use of the ketal adducts of formula (1), especially (1a) allows an increased concentration of active agent in a wide variety of specific personal care formulation forms. The ketal adducts of formula (1), especially (1a) are further compatible with many other ingredients of personal care formulations.

In other cases, the presence or absence of a specific ingredient that can be an aid to solubility is important. For example it can be desirable to reduce or eliminate volatile organic compounds ("VOCs") from a personal care formulation. Some ingredients, such as ethanol, can dry the skin and in some cases are to be avoided for that reason, or for other reasons, such as VOC regulations in some jurisdictions. Conversely, there are other cases in which ethanol and/or another relatively volatile material is desired, so the formulation dries rapidly when it is applied, for example. In some embodiments, use of the ketal adducts of formula (1), especially (1a)

results in formulations with reduced levels of VOCs and in some cases, no VOC's. In an embodiment, the formulations and products described herein can be low-VOC as defined below.

Use of the ketal adducts of formula (1), especially (1a) in personal care formulations can enhance the compatibility amongst the various ingredients of the formulations. Many personal care formulations contain both hydrophilic and hydrophobic components. These ingredients tend not to mix into each other. In order to create a formulation that does not rapidly separate into oil-rich and water-rich layers, emulsifiers, cosolvents, or thickeners can be included so that it becomes kinematically stable. These emulsifiers, cosolvents, and thickeners often play little role in the function or performance of the formulation (i.e., are not active agents), although they can affect the spreading characteristics and feel on the skin. They mainly are present to permit the various functional ingredients to coexist in a stable formulation form or to provide a desired feel or consistency to the formulation. The inclusion of certain compatibilizing ingredients (such as volatile or drying organic solvents, for example), as described above, can more specifically be omitted from some formulations. The need to include such compatibilizers can increase formulation complexity. Formulations that require compatibilization can be very sensitive to small formulational changes. Small changes to a formulation often destabilize it, requiring a new balance of ingredients.

The ketal adducts of formula (1), especially (1a) can perform the function of emulsifiers, oils, cosolvents, compatibilizers, and like materials. In a further advantage, the ketal adducts of formula (1), especially (1a) enhance the spreading of the formulation, and/or do not feel greasy or heavy. Use of the ketal adducts of formula (1) especially (1a) can provide simplified formulations for personal care formulations that still have the needed formulation attributes and functions. In other cases, use of the ketal adducts of formula (1), especially (1a) can reduce the quantities of the various formulary components, and thus can reduce costs and simplify formulating. This can allow a formulator to maintain a simplified raw material inventory and thus reduce associated costs. Use of the ketal adducts of formula (1), especially (1a) can also result in personal care formulations that are more robust to formulation changes.

The following non-limiting examples further illustrate various embodiments of the invention.

EXAMPLES

Example 1

2-Ethylhexyl levulinate propylene glycol ketal (2EH-LPK) was prepared by combining 708.0 grams of EtLPK with 729.2 grams of 2-ethylhexanol (99%) in a two liter, four-neck round bottom flask equipped with stir shaft, thermocouple, Dean-Stark trap/condenser, and heating mantle. The mixture was stirred at 100° C. at 60 torr until water content was below 100 ppm by Karl-Fischer titration (24 hours). A nitrogen blanket was applied and 0.33 grams of tin octoate catalyst was delivered to the reaction mixture by syringe. The stirred reaction mixture was heated to 190° C. for 6.5 hours; displaced ethanol was collected in the trap. The remaining reaction mixture was transferred to a one liter round bottom flask equipped with a stir bar, Vigreaux column, distillation head, and oil bath. The reaction mixture was fractionally distilled under reduced pressure, yielding 605.9 grams of 2-ethylhexyl levulinate propylene glycol ketal with 99.2% purity (by GC-FID).

1-nonanyl levulinate propylene glycol ketal (1N-LPK) was prepared by combining 166.0 grams of EtLPK with 189.9 grams of 1-nonanol (98%) in a one liter, three-neck round bottom flask equipped with stir shaft, thermocouple, Dean-Stark trap/condenser, and heating mantle. The mixture was stirred at 100° C. at 60 torr until water content was below 100 ppm by Karl Fischer titration. A nitrogen blanket was applied and 0.065 ml of tin octoate catalyst was delivered to the reaction mixture by syringe. The stirred reaction mixture was heated to 190° C. for 3.5 hours; displaced ethanol was collected in the trap. The same one liter round bottom flask was equipped with a stir bar, distillation head, and oil bath. The reaction mixture was fractionally distilled under reduced pressure, yielding 146.2 grams of 1-nonanyl levulinate propylene glycol ketal with 97.1% purity (by GC-FID).

3,5,5-Trimethylhexyl levulinate propylene glycol ketal (355TMH-LPK) was prepared by combining 166.1 grams of EtLPK with 190.4 grams of 3,5,5-trimethylhexanol (>85%) in a one liter, three-neck round bottom flask equipped with stir shaft, thermocouple, Dean-Stark trap/condenser, and heating mantle. The mixture was stirred at 100° C. at 60 torr until water content was below 100 ppm by Karl Fischer titration. A nitrogen blanket was applied and 0.065 ml of tin octoate catalyst was delivered to the reaction mixture by syringe. The stirred reaction mixture was heated to 190° C. for 4 hours; displaced ethanol was collected in the trap. The same one liter round bottom flask was equipped with a stir bar, distillation head, and oil bath. The reaction mixture was fractionally distilled under reduced pressure, yielding 188.1 grams of 3,5,5-trimethylhexyl levulinate propylene glycol ketal with 88.1% purity (by GC-FID).

Example 2

Latex coating formulations were prepared using three different latexes: vinyl-acrylic latex (UCAR™ 379G available from Arkema, Inc.), acrylic latex (UCAR™ 625 available from Arkema, Inc.), and another acrylic latex (MAINCOTE™ 54D available from The Dow Chemical Company). The acrylic latex UCAR™ 625 has an acrylic copolymer content of 30 wt. % to 60 wt. % and water content of 30 wt. % to 60 wt. %, based on the weight of the latex, and pH of 9; and the acrylic latex MAINCOTE™ 54D has an acrylic polymer content of 41 wt. % to 42 wt. % and water content of 58 wt. % to 59 wt. % based on the weight of the latex and pH of 7.2 to 7.8.

The latex coating formulations for minimum film forming temperature (MFFT) testing were prepared by adding 20 grams of polymer binder latex (UCAR 379G, UCAR 625, and Maincote HG-54D), 0.04 grams of Rhodoline 643 defoamer (available from Rhodia), and 0.2 or 0.4 grams of coalescent to a vial. The resulting mixture was shaken vigorously by hand to produce a stable latex coating composition.

Formulations are shown in Table A.

TABLE A

| Formulation | Latex | Latex qty (g) | Coalescent | Coalescent qty (g) | Rhodoline 643 qty (g) |
|---|---|---|---|---|---|
| Control | UCAR 379G | 20.0 | | | 0.04 |
| TPM 1 | UCAR 379G | 20.0 | TPM | 0.2 | 0.04 |
| TPM 2 | UCAR 379G | 20.0 | TPM | 0.4 | 0.04 |
| EtLPK 1 | UCAR 379G | 20.0 | EtLPK | 0.2 | 0.04 |
| EtLPK 2 | UCAR 379G | 20.0 | EtLPK | 0.4 | 0.04 |
| iPrLPK1 | UCAR 379G | 20.0 | iPrLPK | 0.2 | 0.04 |
| iPrLPK 2 | UCAR 379G | 20.0 | iPrLPK | 0.4 | 0.04 |

TABLE A-continued

| Formulation | Latex | Latex qty (g) | Coalescent | Coalescent qty (g) | Rhodoline 643 qty (g) |
|---|---|---|---|---|---|
| 2EH-LPK 1 | UCAR 379G | 20.0 | 2EH-LPK | 0.2 | 0.04 |
| 2EH-LPK 2 | UCAR 379G | 20.0 | 2EH-LPK | 0.4 | 0.04 |
| Control | UCAR 625 | 20.0 | | | 0.04 |
| TPM 1 | UCAR 625 | 20.0 | TPM | 0.2 | 0.04 |
| TPM 2 | UCAR 625 | 20.0 | TPM | 0.4 | 0.04 |
| EtLPK 1 | UCAR 625 | 20.0 | EtLPK | 0.2 | 0.04 |
| EtLPK 2 | UCAR 625 | 20.0 | EtLPK | 0.4 | 0.04 |
| iPrLPK1 | UCAR 625 | 20.0 | iPrLPK | 0.2 | 0.04 |
| iPrLPK 2 | UCAR 625 | 20.0 | iPrLPK | 0.4 | 0.04 |
| 2EH-LPK 1 | UCAR 625 | 20.0 | 2EH-LPK | 0.2 | 0.04 |
| 2EH-LPK 2 | UCAR 625 | 20.0 | 2EH-LPK | 0.4 | 0.04 |
| Control | Maincote HG54D | 20.0 | | | 0.04 |
| TPM 1 | Maincote HG54D | 20.0 | TPM | 0.2 | 0.04 |
| TPM 2 | Maincote HG54D | 20.0 | TPM | 0.4 | 0.04 |
| EtLPK 1 | Maincote HG54D | 20.0 | EtLPK | 0.2 | 0.04 |
| EtLPK 2 | Maincote HG54D | 20.0 | EtLPK | 0.4 | 0.04 |
| iPrLPK1 | Maincote HG54D | 20.0 | iPrLPK | 0.2 | 0.04 |
| iPrLPK 2 | Maincote HG54D | 20.0 | iPrLPK | 0.4 | 0.04 |
| 2EH-LPK 1 | Maincote HG54D | 20.0 | 2EH-LPK | 0.2 | 0.04 |
| 2EH-LPK 2 | Maincote HG54D | 20.0 | 2EH-LPK | 0.4 | 0.04 |

MFFT studies were performed using various coalescing solvents to establish their relative coalescing efficiency. The minimum film forming temperature of the ketal adduct 2-ethylhexyl levulinate propylene glycol ketal (2EH-LPK) was compared with the related ketal coalescent solvents ethyl levulinate propylene glycol ketal (EtLPK) and isopropyl levulinate propylene glycol ketal (iPrLPK) and the benchmark commercial coalescent solvent 2,2,4-trimethyl-1,3-pentanediol monoisobutyrate (TPM, available as TEXANOL™ from Eastman Chemical Company). The minimum film forming temperature of a control formulation of pure latex with no coalescent was also measured.

Table 1 shows the minimum film forming temperatures for the formulations at various latex loadings (the weight percent of coalescent solvent based on weight of the latex formulation) as measured using ASTM Method D2359.

TABLE 1

| | Loading (wt. %) | MFFT (° C.) |
|---|---|---|
| UCAR 379G (Vinyl Acrylic Latex) | | |
| control | 0 | 12.0 |
| TPM | 1% | 6.0 |
| TPM | 2% | 2.8 |
| EtLPK | 1% | 4.4 |
| EtLPK | 2% | 1.6 |
| iPrLPK | 1% | 5.1 |
| iPrLPK | 2% | 2.2 |
| 2EH-LPK | 1% | 5.6 |
| 2EH-LPK | 2% | 2.2 |
| UCAR 625 (Acrylic Latex) | | |
| control | 0 | 12.2 |
| TPM | 1% | 5.2 |
| TPM | 2% | 2.3 |
| EtLPK | 1% | 4.3 |
| EtLPK | 2% | 0.9 |
| iPrLPK | 1% | 4.1 |
| iPrLPK | 2% | 0.9 |
| 2EH-LPK | 1% | 4.3 |
| 2EH-LPK | 2% | 1.3 |
| Maincoate 54D (Acrylic Latex) | | |
| control | 0 | >33 |
| TPM | 3% | 13.6 |
| TPM | 6% | 2.8 |
| EtLPK | 3% | 10.8 |
| EtLPK | 6% | 0.0 |
| iPrLPK | 3% | 11.0 |
| iPrLPK | 6% | 1.2 |
| 2EH-LPK | 3% | 13.2 |
| 2EH-LPK | 6% | 2.4 |

Defoamer Rhodoline 643 was added to each formulation in an amount of 0.2% based on the weight of the latex formulation.

The data in Table 1 show that 2EH-LPK depresses the minimum film forming temperature compared to the control. Further, 2EH-LPK produces a minimum film formation temperature that compares favorably with benchmark TPM.

Example 3

The relative volatile organic compound (VOC) contents of the coalescent solvents 2-ethylhexyl levulinate propylene glycol ketal (2EH-LPK), 1-nonyl levulinate propylene glycol ketal (1N-LPK), 3,5,5-trimethylhexyl levulinate propylene glycol ketal (355TMH-LPK), ethyl levulinate propylene glycol ketal (EtLPK), isopropyl levulinate propylene glycol ketal (iPrLPK), and 2,2,4-trimethyl-1,3-pentanediol monoisobutyrate (TPM) were determined by emulating ASTM Method D2369. Here, 15 milligrams (mg) of each coalescent solvent was maintained at 110° C. for one hour with a nitrogen purge in a thermogravimetric analyzer (TGA). Table 2 shows the percentage of mass remaining for each sample at various times.

TABLE 2

| Component | % mass remaining | | | | | | |
|---|---|---|---|---|---|---|---|
| | 0 min | 5 min | 10 min | 15 min | 20 min | 30 min | 60 min |
| EtLPK | 100% | 51% | 7% | 0% | 0% | 0% | 0% |
| iPrLPK | 100% | 60% | 23% | 0% | 0% | 0% | 0% |
| TPM | 100% | 74% | 49% | 26% | 4% | 0% | 0% |
| 2EH-LPK | 100% | 97% | 93% | 90% | 87% | 80% | 61% |
| 1N-LPK | 100% | 99% | 98% | 97% | 96% | 93% | 87% |
| 355TMH-LPK | 100% | 97% | 95% | 92% | 90% | 85% | 71% |

The results in Table 2 show that 2EH-LPK, 1N-LPK, and 355TMH-LPK exhibit low volatility compared to the other coalescing solvents. Surprisingly, a majority of the 2EH-LPK, 1N-LPK, and 355TMH-LPK (80%, 93%, and 85%, respectively) remains after 30 minutes while TPM, EtLPK, and iPrLPK completely volatilize in less than 30 minutes (min).

These data demonstrate that 2EH-LPK is a low-VOC, efficient coalescing solvent.

Example 3

Hydrolytic stability of coalescent solvents at room temperature was determined for 2-ethylhexyl levulinate propylene glycol ketal (2EH-LPK), ethyl levulinate propylene glycol ketal (EtLPK), and isopropyl levulinate propylene glycol ketal (iPrLPK). The pH of latex formulations containing ester-functionalized coalescent solvents was monitored over time to evaluate hydrolytic stability of the coalescent solvents. Not wishing to be bound by theory, ester hydrolysis may occur at a high alkaline pH (for example a pH greater than about 9) during storage of latex compositions. The resulting hydrolysis products lower the pH of the latex composition and could decrease the coalescing efficiency of the coalescing solvent with respect to the initial amount of the coalescing solvent.

Latex formulations were prepared by adding 1.0 gram of each coalescent solvent to 10 grams of an acrylic latex (Rhoplex SG-10M available from Dow Chemical Company) and adjusting the pH of each sample to a pH of 9 using ammonia. A control latex formulation was prepared without adding a coalescent solvent. Table 3 shows the pH of each formulation measured weekly for four weeks while the latex formulations were stored at room temperature.

TABLE 3

| Coalescent | Initial pH | 1 week | 2 weeks | 3 weeks | 4 weeks |
|---|---|---|---|---|---|
| Control (no coalescent) | 9.02 | 8.98 | 9.00 | 9.06 | 9.05 |
| EtLPK | 9.00 | 8.69 | 8.53 | 8.41 | 8.24 |
| iPrLPK | 8.93 | 8.79 | 8.73 | 8.71 | 8.64 |
| 2EH-LPK | 8.97 | 8.99 | 8.94 | 9.03 | 9.00 |

The data in Table 3 show that 2EH-LPK maintains the pH at a value that is near the initial pH over the course of at least four weeks. Further, since the pH remains nearly constant for 2EH-LPK, it is likely that hydrolysis of the ester does not occur to an appreciable extent since carboxylic acids would form and subsequently decrease the composition's pH. The results for 2EH-LPK are quite similar to that for the control that does not have any coalescent solvent. Consequently, 2EH-LPK-containing latex formulations have hydrolytically stable storage properties under alkaline pH conditions.

Example 4

Hydrolytic stability of coalescent solvents at elevated temperature (45° C.) was determined for 1-nonyl levulinate propylene glycol ketal (1N-LPK), 3,5,5-trimethylhexyl levulinate propylene glycol ketal (355TMH-LPK), and ethyl levulinate propylene glycol ketal (EtLPK). Latex formulations were prepared by adding 1.0 gram of each coalescent solvent to 10 grams of an acrylic latex (Rhoplex SG-10M available from Dow Chemical Company) and adjusting the pH of each sample to a pH of 9 using ammonia. A control latex formulation was prepared without adding a coalescent solvent. Table 4 shows the pH of each formulation measured weekly for two weeks while the latex formulations were stored at 45° C.

TABLE 4

| Coalescent | Initial pH | 1 week | 2 weeks |
|---|---|---|---|
| Control (no coalescent) | 8.94 | 9.01 | 8.87 |
| EtLPK | 8.95 | 8.06 | 7.53 |
| 1N-LPK | 8.92 | 8.75 | 8.63 |
| 355TMH-LPK | 8.92 | 8.78 | 8.64 |

The data in Table 4 show that the formulations containing 1N-LPK and 355TMH-LPK maintain pH near the initial pH over the course of two weeks at 45° C., suggesting that hydrolysis of the ester does not occur to an appreciable extent, since carboxylic acids would form and subsequently decrease the composition pH of the composition. The results for 1N-LPK and 355TMH-LPK are quite similar to that for the control, which does not have any coalescent solvent. Consequently, 1N-LPK and 355TMH-LPK-containing latex formulations have hydrolytically stable storage properties under alkaline pH conditions.

Prophetic Examples

The following examples are prophetic. As used throughout the examples, "2EH-LK" refers to 2-ethylhexyl levulinate propylene glycol ketal, "1N-LPK" refers to 1-nonyl levulinate propylene glycol ketal, and "355TMH-LPK" refers to 3,5,5-trimethylhexyl levulinate propylene glycol ketal.

Example 5

This is a prophetic example that is intended to demonstrate the composition of a temporary hair dye and a method of manufacturing of a temporary hair dye. Temporary dye compositions are based on hair and textile dyes having molecules that are too large to penetrate the fiber shaft. The color rinses out after a single shampoo application to the hair. Temporary dyes are also called direct dyes. Temporary dyes add color to hair but they cannot lighten hair color. Table 5 below details compositions of temporary hair dyes. All weights in the Table 5 are given in grams.

TABLE 5

| Ingredient | weight in grams |
|---|---|
| Part A | |
| DI water | 34.55 |
| Carbopol Aqua SF-1 (acrylates copolymer, 30%)[1] | 10 |
| Part B | |
| DI water | 15 |
| disodium EDTA | 0.05 |
| Ketal* | 5 |
| Miranol Ultra-C37 (sodium cocoamphoacetate (37%))[2] | 15 |
| cocamidopropyl betaine (15%) | 3 |
| Polyquaternium-39 | 0.8 |
| Part C | |
| Germaben II (propylene glycol (and diazolidinyl urea (and) methylparaben (and) propylparaben)[3] | 0.45 |
| sodium hydroxide (18%) | 0.25, adjust to pH 7 |
| Part D | |
| DI water | 8 |
| Arianor Sienna Brown (Basic brown 27/CI 12251)[4] | 0.25 |
| Arianor Steel Blue (Basic blue 99/CI 56059)[4] | 0.125 |
| Arianor Madder Red (basic red 76/CI 12245)[4] | 0.125 |
| Dow Corning 193 (PEG-12 dimethicone)[5] | 0.2 |
| Part E | |
| decyl glucoside (50%) | 4 |
| DI water | 3 |
| Timiron MP-149 Diamond Cluster(mica and titanium dioxide)[6] | 0.2 |

[1] from Lubrizol/Noveon Consumer Specialties;
[2] from Rhodia;
[3] from ISP;
[4] from Warner Jenkinson;
[5] from Dow Corning;
[6] from Rona;
*example A: ketal is 2EH-LPK; Example B: ketal is 1N-LPK. Example C: ketal is 355TMH-LPK.

The method for manufacturing the compositions in the Table 5 is as follows:

Slowly add Carbopol to DI (deionized) water (Part A). In a separate vessel, dissolve EDTA in DI water at approximately 50° C. and then add the remaining ingredients of Part B individually with mixing. Part B is slowly added to Part A with moderate mixing. Add the ingredients of Part C individually to the combined Parts A/B to form a main batch, which comprises Part A, Part B and Part C, adjusting the amount of sodium hydroxide so that the pH of the batch is 7. In a separate vessel, dissolve dyes in DI water, keeping temperature below 60° C., and then add PEG-12 dimethicone. Add Part D to main batch, which now comprises Part A, Part B, Part C and Part D. In a separate vessel, prepare Part E by dispersing the pigments in the other ingredients of Part E. Add Part E to the main batch to form the temporary hair dye.

Example 6

This is a prophetic example intended to demonstrate the composition of a semi-permanent hair dye composition and the manufacturing of a semi-permanent hair dye composition. Just like temporary dyes, these formulations rely on direct dyes. However, the semi-permanent dyes comprise smaller molecules based on nitro-phenylene-diamine and due to their small size, the direct dyes in the semi-permanent formulations can penetrate the fiber shaft. As a result, semi-permanent hair dyes can survive about 6 to about 8 shampoo applications to the hair. Table 6 below details compositions of temporary hair dyes. All weights in the Table 6 are given in grams.

TABLE 6

| Ingredient | Weight in grams |
| --- | --- |
| Part A | |
| DI water | 64 |
| Carbomer | 0.5 |
| CROSULTAINE-C50[2] (Cocamidopropyl hydroxysultaine) | 7 |
| BRIJ 020 (Oleth-20)[2] | 0.4 |
| triethanolamine | 0.4 |
| Part B1 (for light/medium brown) | |
| DI water | 11.5 |
| HC Blue #2 CP[1] | 1.5 |
| HC Red #1[1] | 0.6 |
| HC Yellow #4[1] | 0.5 |
| Part B2 (for dark brown/black) | |
| DI water | 10.6 |
| HC Blue #2 CP[1] | 2.5 |
| HC Red #1[1] | 0.4 |
| HC Yellow #4[1] | 0.6 |
| Part B3 (for auburn) | |
| DI water | 12.1 |
| HC Blue #2 CP[1] | 0.3 |
| HC Red #1[1] | 1.5 |
| HC Yellow #4[1] | 0.2 |
| Part C | |
| SD alcohol 40 | 3 |
| Ketal* | 3 |
| CROTHIX LIQUID[2] (PET-150 pentaerythrityl tetrastearate (and) PEG-6 caprylic/capric glycerides (and) water | 3 |
| Crodasone W[2] (Hydrolyzed Wheat Protein PG-propyl silanetriol) | 3 |
| Germaben II[3] (propylene glycol (and diazolidinyl urea (and) methylparaben (and) propylparaben) | 1 |

[1]from Jos. H. Lowenstein and Sons;
[2]from Croda;
[3]from ISP;
*example A: ketal is 2EH-LPK; Example B: ketal is 1N-LPK. Example C: ketal is 355TMH-LPK The process to manufacture the composition of Table 6 is as follows. Carbomer is disposed into water slowly while rapidly mixing the solution and heating the mixture to 65° C. When uniformly dispersed, add remaining ingredients of Part A one at a time, while mixing at moderate speed. Combine ingredients of Part B (either Part B1, Part B2 or Part B3) with mixing while heating to a temperature to 65° C. Add part B to Part A, mixing well. Continue mixing and cool to 40° C. Add ingredients of Part C individually to the mixture of Part A and Part B, mixing well after each addition.

Example 7

This is a prophetic example intended to demonstrate the composition for a semi-permanent hair dye gel composition having a dark brown color. This example also details a method of manufacturing the composition in the Table 7.

TABLE 7

| Ingredient | Weight in grams |
| --- | --- |
| Part A | |
| H.C. Blue #2 solid | 0.36 |
| Lowadene Violet #1[1] | 0.56 |
| H.C. Yellow #4 | 0.24 |
| Lowadene Blue 61505[1] | 0.2 |
| Lowadene Blue 62500[1] | 0.17 |
| H.C. Yellow #5 | 0.02 |
| Ketal* | 6 |
| DI water | 18.34 |
| Part B | |
| oleic acid | 0.82 |
| ethanolamine | 0.18 |
| Part C | |
| Monamid ISO-ADY (linoleamide DEA) [2] | 2 |
| Part D | |
| Structure 2001 polymer (acrylates/steareth-20 itaconate copolymer) [3] | 3.39 |
| DI water | 60.11 |
| Part E | |
| ethanol amine | 2.5 |
| Part F | |
| citric acid (10%) | 5 |

[1]Jos. H. Lowenstein & Sons, Inc;
[2] Uniqema/Croda;
[3] AkzoNobel;
*example A: ketal is 2EH-LPK; Example B: ketal is 1N-LPK. Example C: ketal is 355TMH-LPK The composition is manufactured as follows. With moderate overhead agitation, heat Part A to about 50 to about 60° C. and mix dyes well. Cool to 40° C. Add Part B and Part C to Part A and mix well. Add Part D to the dye solution and mix well. Add Part E to the dye solution and mix well. Finally, add Part F to dye solution and mix well.

Example 8

This is a prophetic example intended to demonstrate a composition used to manufacture a permanent hair dye composition. A method of manufacturing the permanent hair dye is also described. Permanent hair dyes are based on oxidative dye chemistry and are formulated in two packages that are mixed at the time of dyeing. One package contains color dye intermediates in an alkaline solution, while the other package contains the peroxide activator that both lightens hair and converts the dye intermediate to its color form. Because permanent hair dye formulations can dye as well as bleach hair, hair can be dyed to a lighter shade than its natural color. Table 8 demonstrates the composition of a permanent hair dye.

TABLE 8

| Ingredients | Weight in grams |
|---|---|
| Phase A | |
| Deionized Water | 52.51 |
| Sodium sulfite | 0.30 |
| EDTA | 0.20 |
| Erythorbic acid | 0.30 |
| p-Phenylenediamine | 1.70 |
| 4-amino-2-hydroxytoluene | 0.06 |
| Resorcinol | 1.40 |
| o-Aminophenol | 1.40 |
| Toluene-2,5-diamine Sulfate | 0.11 |
| 1-Napthol | 0.02 |
| Ketal* | 3 |
| Incromide CA (Cocamide DEA) | 3.50 |
| Incromectant AMEA-100 (Acetamide MEA) | 1.00 |
| Phase B | |
| KeraTint EZ ((Cetyl alcohol [and] stearyl alcohol[and] PPG-5 ceteth-20 & Dicetyl Phosphate[and] ceteth-10 phosphate [and] behentrimonium methosulfate) | 12 |
| Ketal* | 9 |
| Phase C | |
| Crodasone W (hydrolyzed wheat protein PG-propyl silanetriol) | 2.00 |
| Crosilkquat(Cocamidopropyl hydroxypropyl silk amino acids) | 0.50 |
| Crosultaine C-50 (Cocamidopropyl hydroxysultaine) | 1.00 |
| Phase D | |
| Ammonia | 10.00 |

*example A: ketal is 2EH-LPK; Example B: ketal is 1N-LPK. Example C: ketal is 355TMH-LPK.

The method of manufacturing of the composition of Table 8 is as follows.

Combine the ingredients of phase A in a main vessel and heat to 75° C. In a separate vessel, heat phase B to 75° C. Add phase B to phase A with mixing. Cool to 50° C. and add ingredients of phase C individually, mixing well after each addition. Cool to 40° C., add phase D and mix until homogenous. This formulation must be mixed with a hydrogen peroxide developer prior to use.

Examples 9-47

The following prophetic examples demonstrate soluble formulations that include an alkyl ketal ester and an essential oil.

Table 9 shows 39 different fragrant formulations that can be obtained by blending an alkyl ketal ester and an essential oil. The alkyl ketal ester and the essential oil are blended in a weight ratio of 1:1 at room temperature using gentle agitation. Solubility is visually determined immediately after mixing. Clear solutions are described as "miscible" and solutions that are either cloudy or show evidence of a second phase are labeled as "immiscible."

TABLE 9

| Ex. # | Solvent | Pure Essential Oil | Miscibility of 50/50 blend by weight |
|---|---|---|---|
| 9 | 2EH-LPK | Orange (*Citrus sinensis*) | Miscible |
| 10 | 2EH-LPK | Patchouli (*Pogostemon patchouli*) | Miscible |
| 11 | 2EH-LPK | Ylang ylang (*Canaga odorata*) | Miscible |
| 12 | 2EH-LPK | Coriander seed (*Coriandrum sativum*) | Miscible |
| 13 | 2EH-LPK | Birch sweet (*Betula lenta*) | Miscible |
| 14 | 2EH-LPK | Citronella (*Cymbopogon nardus*) | Miscible |
| 15 | 2EH-LPK | Pine needle (*pinus sylvestris*) | Miscible |
| 16 | 2EH-LPK | Vetiver (*Vetivera zizanoides*) | Miscible |
| 17 | 2EH-LPK | Basil (*Ocimum basilicum*) | Miscible |
| 18 | 2EH-LPK | Myrrh (*Commiphora myrrha*) | Miscible |
| 19 | 2EH-LPK | Geranium (*Pelargonium graveolens*) | Miscible |
| 20 | 2EH-LPK | Bergamot (*Citrus bergamia*) | Miscible |
| 21 | 2EH-LPK | Lavender (*Lavandula angustifolium*) | Miscible |
| 22 | 1N-LPK | Orange (*Citrus sinensis*) | Miscible |
| 23 | 1N-LPK | Patchouli (*Pogostemon patchouli*) | Miscible |
| 24 | 1N-LPK | Ylang ylang (*Canaga odorata*) | Miscible |
| 25 | 1N-LPK | Coriander seed (*Coriandrum sativum*) | Miscible |
| 26 | 1N-LPK | Birch sweet (*Betula lenta*) | Miscible |
| 27 | 1N-LPK | Citronella (*Cymbopogon nardus*) | Miscible |
| 28 | 1N-LPK | Pine needle (*pinus sylvestris*) | Miscible |
| 29 | 1N-LPK | Vetiver (*Vetivera zizanoides*) | Miscible |
| 30 | 1N-LPK | Basil (*Ocimum basilicum*) | Miscible |
| 31 | 1N-LPK | Myrrh (*Commiphora myrrha*) | Miscible |
| 32 | 1N-LPK | Geranium (*Pelargonium graveolens*) | Miscible |
| 33 | 1N-LPK | Bergamot (*Citrus bergamia*) | Miscible |
| 34 | 1N-LPK | Lavender (*Lavandula angustifolium*) | Miscible |
| 35 | 355TMH-LPK | Orange (*Citrus sinensis*) | Miscible |
| 36 | 355TMH-LPK | Patchouli (*Pogostemon patchouli*) | Miscible |
| 37 | 355TMH-LPK | Ylang ylang (*Canaga odorata*) | Miscible |
| 38 | 355TMH-LPK | Coriander seed (*Coriandrum sativum*) | Miscible |
| 39 | 355TMH-LPK | Birch sweet (*Betula lenta*) | Miscible |
| 40 | 355TMH-LPK | Citronella (*Cymbopogon nardus*) | Miscible |
| 41 | 355TMH-LPK | Pine needle (*pinus sylvestris*) | Miscible |
| 42 | 355TMH-LPK | Vetiver (*Vetivera zizanoides*) | Miscible |
| 43 | 355TMH-LPK | Basil (*Ocimum basilicum*) | Miscible |
| 44 | 355TMH-LPK | Myrrh (*Commiphora myrrha*) | Miscible |
| 45 | 355TMH-LPK | Geranium (*Pelargonium graveolens*) | Miscible |
| 46 | 355TMH-LPK | Bergamot (*Citrus bergamia*) | Miscible |
| 47 | 355TMH-LPK | Lavender (*Lavandula angustifolium*) | Miscible |

Examples 48-63

The following examples demonstrate prophetic compatibility or incompatibility between various fragrant compositions and the alkyl ketal esters. Table 10 demonstrates the solubility of 2EH-LPK, 1N-LPK and 355 TMH-LPK with the listed oils.

TABLE 10

| Example | Oil | % alkyl ketal ester | Result |
|---|---|---|---|
| 48 | Castor oil | 50 | Miscible |
| 49 | C12-15 alkyl benzoate | 25 | Miscible |
| 50 | Isopropyl myristate | 50 | Miscible |
| 51 | Caprylic/capric triglycerides (Neobee M-5) | 50 | Miscible |
| 52 | Octyl palmitate | 50 | Miscible |
| 53 | Mineral oil | 50 | Miscible |
| 54 | Coconut Oil | 50 | miscible |
| 55 | cyclomethicone | 50 | miscible |
| 56 | Avocado oil | 50 | miscible |

TABLE 10-continued

| Example | Oil | % alkyl ketal ester | Result |
|---|---|---|---|
| 57 | Canola oil | 50 | miscible |
| 58 | Grapeseed Oil | 50 | miscible |
| 59 | Sesame seed oil | 29 | miscible |
| 60 | Soybean oil | 49 | miscible |
| 61 | Squalane Pripure 3759 | 50 | miscible |
| 62 | Caprylyl methicone (DC FZ-3196) | 50 | miscible |
| 63 | Oleyl alcohol | 50 | miscible |

From the Table 10 above, it may be seen that materials including vegetable oils, animal fats and derivatives are useful fragrant compounds and can be miscible with at least one of the alkyl ketal esters. Examples of useful fragrant compounds include for example, acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, *macadamia* nut oil, rose hip oil, ajwain oil, angelic root oil, anise oil, aragan oil, asafetida, balsam oil, basil oil, bay oil, bergamot oil, black pepper essential oil, buchu oil, birch oil, camphor, *cannabis* oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, *helichrysum*, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, *perilla* oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, *tsuga* oil, turmeric, valerian, vetiver oil, western red cedar, wintergreen, yarrow oil, ylang-ylang, and zedoary oil.

Examples 64-65

These examples demonstrate the manufacturing of perfume formulations that contain alkyl ketal esters. Table 11 reflects Examples 64 and 65. Components are added at room temperature and gently agitated by shaking. Solubility is visually determined immediately after mixing. All formulations are clear. Composition is given in weight percent (wt %).

TABLE 11

|  | Example 64 | Example 65 |
|---|---|---|
| orange oil | 1.4% | 1.3% |
| bergamot | 1.9% | 1.8% |
| myrrh | 1.2% | 1.1% |
| citronella | 1.3% | 1.2% |
| cedarwood | 0.6% | 0.6% |
| DI water | 8.2% | 14.7% |
| Ketal* | 6.6% | 6.1% |
| ethanol | 78.9% | 73.2% |

*example A: ketal is 2EH-LPK; Example B: ketal is 1N-LPK. Example C: ketal is 355TMH-LPK.

Example 66

This is a prophetic example that describes the manufacturing of an air freshener. The formulation is listed in Table 12 below. In order to manufacture the air freshener, the ingredients of part A and part B are first mixed individually and then added together with continual mixing. The ingredients of Part A are added in the order listed in the Table 9 and then mixed for a minimum for a period of 30 minutes. The water is heated to 100-130° F.

TABLE 12

| Ingredient | Weight % |
|---|---|
| Part A | |
| DI Water | 65.7 |
| Laponite RD | 3.0 |
| Aqualon CMC-9H4F | 0.3 |
| Part B | |
| Ketal* | 15 |
| Fragrance | 15 |
| Cola ®Mulse Emultron PM | 1 |

*example A: ketal is 2EH-LPK; Example B: ketal is 1N-LPK. Example C: ketal is 355TMH-LPK.

Examples 67-72

Waxes

The following examples are conducted to demonstrate the use of a fragrant formulation in candles. Compatibility between various waxes and the alkyl ketal esters are first determined as detailed below. Table 13 below details the fragrant formulations for different candles that contain the fragrant composition.

Beeswax

Beeswax and 2EH-LPK are weighed into a vessel at 50/50 weight ratio and heated to 80° C. to form a uniform molten mixture. The mixture forms a single homogenous wax layer upon cooling to room temperature.

Beeswax and 1N-LPK are weighed into a vessel at 50/50 weight ratio and heated to 80° C. to form a uniform molten mixture. The mixture forms a single homogenous wax layer upon cooling to room temperature.

Beeswax and 355TMH-LPK are weighed into a vessel at 50/50 weight ratio and heated to 80° C. to form a uniform molten mixture. The mixture forms a single homogenous wax layer upon cooling to room temperature.

Paraffin Wax

Gulf Wax brand of household paraffin wax for canning and candlemaking (distributed by Royal Oak Enterprises) can be used in these experiments.

Paraffin wax and 2EH-LPK are weighed into a vessel at 50/50 weight ratio and heated to 80° C. to form a uniform molten mixture. The mixture forms a single homogenous wax layer upon cooling to room temperature. Paraffin wax and 2EH-LPK are weighed into a vessel at 75/25 weight ratio and heated to 80° C. to form a uniform molten mixture. The mixture forms a single homogenous wax layer upon cooling to room temperature.

Paraffin wax and 1N-LPK are weighed into a vessel at 50/50 weight ratio and heated to 80° C. to form a uniform molten mixture. The mixture forms a single homogenous wax layer upon cooling to room temperature. Paraffin wax and 1N-LPK are weighed into a vessel at 75/25 weight ratio and heated to 80° C. to form a uniform molten mixture. The mixture forms a single homogenous wax layer upon cooling to room temperature.

Paraffin wax and 355TMH-LPK are weighed into a vessel at 50/50 weight ratio and heated to 80° C. to form a uniform molten mixture. The mixture forms a single homogenous wax layer upon cooling to room temperature. Paraffin wax and 355TMH-LPK are weighed into a vessel at 75/25 weight ratio and heated to 80° C. to form a uniform molten mixture. The mixture forms a single homogenous wax layer upon cooling to room temperature.

Carnauba Wax

Carnauba wax and 2EH-LPK are weighed into a vessel at 50/50 weight ratio and heated to 120° C. to form a uniform molten mixture. A single homogenous wax layer is formed upon cooling.

Carnauba wax and 1N-LPK are weighed into a vessel at 50/50 weight ratio and heated to 120° C. to form a uniform molten mixture. A single homogenous wax layer is formed upon cooling.

Carnauba wax and 355TMH-LPK are weighed into a vessel at 50/50 weight ratio and heated to 120° C. to form a uniform molten mixture. A single homogenous wax layer is formed upon cooling.

Stearic Acid

Stearic acid and 2EH-LPK are weighed into a vessel at 50/50 weight ratio and heated to 80° C. to form a uniform molten mixture. The mixture forms a single homogenous wax layer upon cooling to room temperature.

Stearic acid and 1N-LPK are weighed into a vessel at 50/50 weight ratio and heated to 80° C. to form a uniform molten mixture. The mixture forms a single homogenous wax layer upon cooling to room temperature.

Stearic acid and 355TMH-LPK are weighed into a vessel at 50/50 weight ratio and heated to 80° C. to form a uniform molten mixture. The mixture forms a single homogenous wax layer upon cooling to room temperature.

The following Table 13 details formulations for different candles that contain the waxes detailed above and the alkyl ketal ester. The formulations are manufactured by combining three parts (Part A, Part B and Part C). Candle formulations 116-120 (Examples 116-120) are manufactured by weighing Part A ingredients into a vessel and heating them at 80° C. until the mixture is in liquid from. The vessel is removed from the heat and Part C is added to the vessel. While the mixture is still liquid, the mixture is poured into a container and a wick with a metal tab base is inserted into the center of the mixture. The completed candle is allowed to cool to room temperature.

Candle formulations 67-72 are manufactured by weighing Part A into a vessel and heating them at 80° C. until the mixture is liquid. Part B is added to Part A and mixed for 2 minutes. The vessel is removed from the heat and Part C is added to the vessel. While the mixture is still liquid, the candle is poured into a container and a wick with a metal tab base is inserted into the center of the mixture. The completed candle is allowed to cool to room temperature.

TABLE 13

| Ingredient | 67 | 68 | 69 | 70 | 71 | 72 |
|---|---|---|---|---|---|---|
| Part A (ingredient weights given as weight % of total formulation) | | | | | | |
| Nature Wax P-1 | 10% | 28% | 28% | 28% | 0% | 0% |
| Nature Wax C-1 | 26% | 6% | 6% | 6% | 29.9% | 29.9% |
| Nature Wax C-3 | 26% | 0% | 0% | 0% | 29.9% | 29.9% |
| Beeswax | 28% | 56% | 56% | 56% | 29.9% | 29.9% |

TABLE 13-continued

| Ingredient | 67 | 68 | 69 | 70 | 71 | 72 |
|---|---|---|---|---|---|---|
| Part B (ingredient weights given as weight % of total formulation) | | | | | | |
| Cinqasia Red B RT-195-1 | 0% | 0% | 0% | 0% | 0.30% | 0.31% |
| Part C (ingredient weights given as weight % of total formulation) | | | | | | |
| 355TMH-LPK | 0% | 5% | 0% | 0% | 5% | 0% |
| 1N-LPK | 5% | 0% | 0% | 5% | 0% | 0% |
| 2EH-LPK | 0% | 0% | 5% | 0% | 0% | 5% |
| Bergamot (*Citrus bergamia*) essential oil | | 5% | 5% | 5% | 0% | 0% |
| Grapefruit essential oil | 4% | 0% | 0% | 0% | 0% | 0% |
| Lavender (*Lavandula angustifolium*) essential oil | 1% | 0% | 0% | 0% | 0% | 0% |
| Lemon essential oil | 0% | 0% | 0% | 0% | 5% | 4.99% |

All of the formulations form candles.

Example 73

This example is conducted to demonstrate the use of a fragrant composition comprising vanillin in a perfume formulation (a candle). The ingredients of the composition are shown in the Table 14 below. The ingredients of the composition are divided into two parts—Part A and Part B, which are then processed as follows: The ingredients of Part B are mixed at room temperature until the vanillin is completely dissolved. In a separate container, the ingredients of Part A are heated at 80° C. until a uniform, molten mixture forms. Part B is then added to part A (while at 80° C.) and mixed until uniform. The vessel containing the Parts A and B are then poured into candle mold. A wick can be added to the candle.

TABLE 14

| Ingredient | Wt % |
|---|---|
| Part A | |
| Paraffin wax | 37.5% |
| Beeswax | 37.5% |
| Part B | |
| Ketal* | 22.5% |
| vanillin | 2.5% |

*example A: ketal is 2EH-LPK; Example B: ketal is 1N-LPK. Example C: ketal is 355TMH-LPK.

A solid, uniform candle forms upon cooling, with no signs of separation.

Example 74

Model Ethanolic Avobenzone Sunscreen Solutions

Three-component mixtures of ketal, ethanol, and avobenzone are prepared by mixing the materials at various proportions at room temperature in a vial and shaking. Avobenzone by itself is immiscible in ethanol at the 5% by weight level.

The ketals used are as follows: A: ketal is 2EH-LPK; Example B: ketal is 1N-LPK. Example C: ketal is 355TMH-LPK.

These data will show that avobenzone concentrations higher than 5% can be achieved in an ethanolic solution through the addition of ketal as a cosolvent. Thus, higher concentrations of this UV agent can be provided in a formulation that is suitable for use in a spray-on sunscreen formulation.

Example 75

Model Ethanolic and Aqueous Oxybenzone Sunscreen Solutions

Three-component mixtures of ketal, ethanol, and oxybenzone are prepared by mixing the materials at various proportions at room temperature in a vial and shaking. The ketals used are as follows: A: ketal is 2EH-LPK; Example B: ketal is 1N-LPK. Example C: ketal is 355TMH-LPK. Clear mixtures are considered to be "miscible" on this test, whereas cloudy or phase separated mixtures are considered to be "immiscible." Oxybenzone by itself is immiscible in ethanol at the 10% by weight level.

These data will show that oxybenzone concentrations higher than 10% by weight can be achieved in an ethanolic solution through the addition of ketal as a cosolvent. Thus, higher concentrations of this UV agent can be provided in a formulation that was suitable as a spray-on sunscreen formulation.

Example 76

Ethanolic Spray Sunscreen Solution

A model spray sunscreen formulation contains 64.4 parts ethanol, 3 parts of an acrylate/octylacrylamide copolymer, 3 parts of octyldodecanol, 7.5 parts of octinoxate, 4 parts of oxybenzone, 5 parts of octisalate, 3 parts of avobenzone, 2.5 parts of POLYCRYLENE® (CAS No. 862993-96-2), 2.5 parts of octocrylene and 5.1 parts of water.

Because ethanol is drying, it is desirable to reduce the ethanol concentration in the formulation. When 10 parts of the ethanol is replaced with 10 parts of 2EH-LPK, 1N-LPK or 355TMH-LPK, a stable solution is obtained that is less drying to the skin due to the reduction in ethanol content.

Examples 77-78

Sunscreen Lotion

Model sunscreen lotions are made from the ingredients shown in Table 15.

TABLE 15

| Ingredients | Ex. 77 wt. % | Ex. 78 wt. % |
|---|---|---|
| Part A | | |
| Ketal** | 0 | 1 |
| Cetyl alcohol | 1 | 0 |
| Stearic acid | 2 | 2 |
| Octyl palmitate | 3 | 3 |
| Octylmethoxyl cinnamate | 7.5 | 7.5 |
| Oxybenzone | 3 | 3 |
| PEG-40 stearate | 1.5 | 1.5 |
| Dimethyl stearamine | 2 | 2 |
| Acrylates/octylacrylamide copolymer (Dermacryl 79) | 2 | 2 |

TABLE 15-continued

| Ingredients | Ex. 77 wt. % | Ex. 78 wt. % |
|---|---|---|
| Part B | | |
| Deionized water | To 100 | To 100 |
| Crosslinked polyacrylate copolymer (Carbopol ETD 2050)* | 0.06 | 0.06 |
| Triethanolamine | 0.7 | 0.7 |

*The amount of thickener should be adjusted based on the efficiency of the carbopol grade
**example A: ketal is 2EH-LPK; Example B: ketal is 1N-LPK. Example C: ketal is 355TMH-LPK.

To prepare the sunscreen lotion formulations, Part B is first prepared by adding the carbomer slowly into the water with mixing and heated to 80° C. The triethanol amine is then added to complete Part B. In a separate vessel, the ingredients from Part A are combined except for the acrylates/octylacrylamide copolymer. These components are heated to 80° C. with mixing. The acrylates/octylacrylamide copolymer are then slowly sifted into Part A under constant stirring until dissolved. Part A is then added to Part B and mixed for 15 minutes at 80° C. The mixture is then slowly cooled to room temperature. Example 78 is less viscous, and remains stable for at least four weeks. The modified product should have a lighter, less greasy feel.

Example 79

Personal Care or Medicinal Active Agents

Salicylic Acid
  Salicylic acid (U.S.P. grade is available from J. T. Baker) is dissolved at 1% solids in 2EH-LPK. After 24 hours at room temperature, there is no evidence of precipitation. The example is repeated with 1N-LPK and 355TMH-LPK replacing 2EH-LPK with similar results.
Retinoic Acid (all Trans)
  Retinoic acid (Tretinoin, available from Tokyo Chemical Industry) is dissolved in 2EH-LPK at 0.1% solids. After 1 day at room temperature, there is no sign of precipitation. The example is repeated with 1N-LPK and 355TMH-LPK replacing 2EH-LPK with similar results.
Tea Tree Oil
  Certified organic tea tree oil (*Melaleuca alternifolia*, plant sourced from Australia and extracted by steam distillation) can be purchased from Wyndmere Naturals. A 50/50 mixture of 2EH-LPK, 1N-LPK or 355TMH-LPK and tea tree oil is miscible at room temperature.
Lactic Acid
  Lactic acid (available from Alfa Chem, Ashland Distribution, and Spectrum Chemical Mfg. Corp) forms a homogeneous solution in 2EH-LPK, 1N-LPK or 355TMH-LPK at a 5/95 ratio of lactic acid to ketal.
Ubiquinone (Coenzyme Q10)
  Coenzyme Q10 is soluble in 2EH-LPK, 1N-LPK, or 355TMH-LPK at 0.1% or greater and stays in solution at room temperature overnight.
Dimethylmethoxy Chromanyl Palmitate
  Dimethylmethoxy chromanyl palmitate (available as Chromabright from Liopotec) at forms a homogeneous solution in 2EH-LPK, 1N-LPK or 355TMH-LPK at 0.1% or greater and stays in solution at room temperature overnight. The recommended dosage level is 0.1%.
Tetrahydrodiferuloylmethane (Tetrahydrocurcuminoids)
  Tetrahydrocurcuminoids (available from lotioncrafter.com) is dissolved at 1% solids in 2EH-LPK at 50° C. to form a clear uniform solution. The mixture is still soluble after 24 hours of storage at room temperature. The example is repeated with 1N-LPK and 355TMH-LPK replacing 2EH-LPK with similar results. The recommended usage rate is 0.1-1%.

Resveratrol

Resveratrol (available from Enzo Life Sciences) is dissolved at 0.1% solids in 2EH-LPK, 1N-LPK or 355TMH-LPK at 50° C. The three mixtures are still soluble after 24 hours of storage at room temperature.

Tetrahydropiperine

Tetrahydropiperine (available as Cosmoperine from lotioncrafter.com) is dissolved at 1% solids in 2EH-LPK, 1N-LPK and 355TMH-LPK at room temperature. The mixtures are still soluble after 24 hours of storage at room temperature. Tetrahydropiperine is a co-ingredient in anti-aging formulations and is thought to improve the bioavailability of active agents.

Dimethylmethoxy Chromanol

Dimethylmethoxy Chromanol (available as Lipochroman-6 from lotioncrafter.com) is dissolved at 0.1% solids in 2EH-LPK, 1N-LPK and 355TMH-LPK at room temperature. The mixtures are still soluble after 24 hours of storage at room temperature. The recommended usage rate is 0.01-0.05%.

Example 80

Antiperspirant

The following is a prophetic formulation for a roll on antiperspirant.

TABLE 16

Roll-on antiperspirant

| Ingredient | weight % |
|---|---|
| Part A | |
| Steareth-2 (VOLPO S-2, Croda) | 2.2 |
| Steareth-20 (VOLPO S-20, Croda) | 0.6 |
| PPG-10 cetyl ether | 5 |
| Ethanol | 5 |
| ketal * | 5 |
| Part B | |
| DI water | 37.2 |
| Part C | |
| Aluminum chloride, 32 C Baum (Reheis Chemical Co.) | 5 |
| Chlorhydrol, 50% (Reheis Chemical Co.) | 40 |

* ketal examples: Ex. A, 2EH-LPK; Ex. B, 1N-LPK; Ex. C, 355TMH-LPK

To manufacture the roll-on antiperspirant, combine ingredients of Part A with mixing and heat to 65-70° C. Heat Part B to 65-70° C. Add Part B to Part A with mixing & cool to 45° C. Add Part C with mixing & cool to desired fill temperature.

Example 81

Lipstick

The following is a prophetic example of a lipstick formulation.

TABLE 17

Lipstick.

| | Ingredient | weight % |
|---|---|---|
| Part A | Caprylic/Capric Triglyceride | 8.56 |
| | Octyldodecyl Stearoyl Stearate | 13.37 |
| | Triisostearyl Citrate | 4.05 |
| | Pentaerythrityl Tetraisostearate | 5.60 |
| | Jojoba Esters | 1.72 |
| | Lanolin Oil | 1.62 |
| | Bis-Diglyceryl Polyacyladipate-2 | 1.02 |
| | *Ricinus Communis* (Castor) Seed Oil | 20.50 |
| | *Copernicia Cerifera* (Carnauba) Wax | 2.30 |
| | *Euphorbia Cerifera* (Candelilla) Wax | 5.24 |
| | Cera Alba (Beeswax) | 2.09 |
| | Ozokerite Wax | 1.80 |
| | Microcrystalline Wax | 1.13 |
| | Phenoxyethanol | 1.00 |
| | Polyethylene | 1.00 |
| | Octyl Methoxycinnamate | 0.60 |
| | Tocopheryl Acetate | 0.05 |
| Part B | *Ricinus Communis* (Castor) Seed Oil | 10.00 |
| | D&C Red No. 6 Barium Lake | 6.25 |
| | Iron Oxide | 0.10 |
| | ketal * | 12 |

* ketal examples: Ex. A, 2EH-LPK; Ex. B, 1N-LPK; Ex. C, 355TMH-LPK

To manufacture the example formulations, weigh Part A and begin heating to 80-85° C. with mixing. Pregrind Part B. When Part A is completely melted and clear, add Part B color grind to Part a wax/oil mixture. When all the color is dispersed and the batch is uniform, pour into molds.

Example 82

Solid Lip Gloss

The following is a prophetic example of a solid lip gloss formulation.

TABLE 18

Solid Lip Gloss.

| | Ingredient | weight % |
|---|---|---|
| Part A | Castor oil | 36.4 |
| | Ketal* | 10 |
| | Polyisobutene 250 | 30 |
| | Bees wax | 10 |
| | Candelila wax | 9 |
| | Mica pigment | 3 |
| Part B | Vitamin E acetate | 1 |
| | BHT | 0.2 |
| | Food flavoring | 0.4 |

*ketal examples: Ex. A, 2EH-LPK; Ex. B, 1N-LPK; Ex. C, 355TMH-LPK

To manufacture the example formulations, add Part A into a vessel and heat to 75° C. to melt wax, mixing until uniform. Remove from heat and add Part B, stirring well. While still liquid, pour into cosmetic container.

Example 83

Lip Balm

The following is a prophetic example of a lip balm formulation.

TABLE 19

Lip Balm

| | Ingredient | weight % |
|---|---|---|
| Part A | Fractionated coconut oil | 13 |
| | Ketal | 10 |
| | Castor oil | 15 |
| | Triglyceride | 23 |
| | Shea butter | 12 |
| | Bees wax | 17 |
| | Lecithin | 1 |
| Part B | Titanium dioxide (optional: nano-sized) | 2 |
| | ketal * | 4.8 |
| Part C | Provitamin B5 | 1 |
| | Vitamin E acetate | 0.1 |
| | Vitamin E Tocopherol | 0.1 |
| | Allantoin | 0.2 |
| | Paraben-DU** | 0.5 |
| | Food flavoring | 0.3 |

* ketal examples: Ex. A, 2EH-LPK; Ex. B, 1N-LPK; Ex. C, 355TMH-LPK
**Paraben-DU - premixed broad-spectrum preservative blend (3 wt. % propylparaben, 11 wt. % methylparaben, 30 wt. % diazolidinyl urea, 56 wt. % propylene glycol).

To manufacture the example formulations, pre-grind or pre-mix the ingredients of Part C. Add Part A to vessel and heat to 65 C until wax and butter are melted. Slowly add in Part C with mixing and mix until well dispersed. Remove from heat. Add ingredients of Part C to Parts A/B one by one and make sure the formulation is well mixed. Fill into molds while the formulation is still liquid. Allow to cool.

Example 84

Pressed Powder Eye Shadow

The following is a prophetic example of a pressed powder eye shadow formulation.

TABLE 20

Pressed Powder Eye Shadow "Nude Glitter"

| | Ingredient | weight % |
|---|---|---|
| Part A | ketal * | 4 |
| | Cyclodimethicone | 3 |
| | Polyglyceryl oleate | 0.75 |
| | Vitamin E acetate | 1 |
| Part B | Pearl white mica | 31 |
| | Mica spheres (powder base) | 20 |
| | Talc powder (powder base) | 20 |
| | Beige mica | 5 |
| | Magnesium stearate | 5 |
| | Bismuth oxychloride (powder base) | 5 |
| | Titanium dioxide | 5 |

* ketal examples: Ex. A, 2EH-LPK; Ex. B, 1N-LPK; Ex. C, 355TMH-LPK

To manufacture the example formulations, combine the titanium dioxide and the pearl white mica in a mortar, stir very well and thoroughly with the pestle until the color is uniform. Add then the other ingredients of Part B, one after another, mixing well after each addition. Then add Part A to the mortar, starting with the ketal, and blend well, for several minutes or until the ingredients are mixed and the color looks uniform. Fill the eye shadow into an eye shadow jar and press it with a suitable tool into eye shadow containers.

Example 85

Anhydrous Mascara

The following is a prophetic example of an anhydrous mascara formulation.

TABLE 21

Anhydrous Mascara

| | Ingredient | weight % |
|---|---|---|
| Part A | ketal * | 30.95 |
| | AC polyethylene 6a wax | 11 |
| | Candelilla wax | 4.5 |
| | Hydroxylated lanolin | 0.25 |
| Part B | pentaerythrityl rosinate | 2 |
| | C9-11 isoparaffin | 2 |
| Part C | methylparaben | 0.2 |
| | propylparaben | 0.1 |
| Part D | zinc stearate | 1 |
| Part E | silica silylate | 1 |
| Part F | Petroleum distillates, quaternium-18 hectorite, propylene carbonate | 35 |
| Part G | black iron oxide | 12 |

* ketal examples: Ex. A, 2EH-LPK; Ex. B, 1N-LPK; Ex. C, 355TMH-LPK

To manufacture the example formulations, prepare Part B in advance by stirring in a sealed vessel until dissolved. In a separate closed vessel, combine the ingredients of Part A and heat to 90-95° C. with stirring. When Part A is clear and well-mixed, add Part B and Part C, stirring until dissolved. Add Parts D through F in sequential order, mixing well with high shear after each addition.

Example 86

Colored Pencil

The following is a prophetic example of a colored pencil formulation.

TABLE 22

Colored Pencil

| | Ingredient | weight % |
|---|---|---|
| Part A | Ethyl cellulose | 1.5 |
| | Isostearyl alcohol | 5.9 |
| | Stearyl alcohol | 5.9 |
| Part B | Hydrogenated vegetable oil | 6.7 |
| | Paraffin | 6.7 |
| Part C | Colorants | 33.3 |
| | ketal * | 5 |
| Part D | Cyclomethicone | 35 |

* ketal examples: Ex. A, 2EH-LPK; Ex. B, 1N-LPK; Ex. C, 355TMH-LPK

To manufacture the example formulations, mix Part A and heat at 65-90° C. with stirring until everything dissolves. Maintain temperature of Part A. In a separate vessel, mix Part B and melt. Add molten Part B to hot Part A. Mix Part C and add to Parts A/B. Homogenize mixture and then mix in Part D. Pour mixture into a mold to cool. Remove the pencil from mold when solidified and cooled.

Example 87

Oil in Water Foundation

The following is a prophetic example of an oil in water foundation formulation.

TABLE 23

Oil in Water Foundation

| | Ingredient | weight % | Function |
|---|---|---|---|
| Part A | DI water | 50.92 | Diluents |
| | tromethamine | 0.8 | alkali (soap) |
| | PEG-12 dimethicone | 0.1 | wetting agent |
| | 80% TiO2/talc extender | 8 | Pigment |
| | 80% yellow iron oxide/talc ext. | 0.95 | Pigment |
| | 80% red iron oxide/talc ext | 0.75 | Pigment |
| | 80% black iron oxide/talc ext. | 0.07 | Pigment |
| | talc, average 4 micron | 4.23 | Filler |
| Part B | butylene glycol | 4 | Humectants |
| | magnesium aluminum silicate | 1 | Thickener |
| Part C | butylene glycol | 2 | Humectants |
| | cellulose gum | 0.15 | Thickener |
| Part D | sucrose cocate | 1 | Emulsifier |
| | methyl paraben | 0.2 | Preservative |
| | disodium EDTA | 0.05 | preservative aid |
| Part E | stearic acid | 1.5 | acid portion of soap |
| | isostearic acid | 0.5 | Soap |
| | dicaprylyl maleate | 10 | Emollient |
| | ketal * | 6 | Emollient |
| | sorbitol monolaurate | 3 | Emulsifier |
| | cetyl alcohol | 0.5 | Stabilizer |
| | propyl paraben | 1 | Preservative |
| Part F | cyclomethicone | 2 | volatile emollient |
| Part G | DI water | 2 | Diluents |
| | DMDM hydantoin | 0.1 | Preservative |

* ketal examples: Ex. A, 2EH-LPK; Ex. B, 1N-LPK; Ex. C, 355TMH-LPK

To manufacture the example formulations, combine Part A ingredients in order while homogenizing. Combine and add Part B. Heat to 85-90° C. for 15 minutes and then cool to 75° C. Combine and add Part C. Add Part D ingredients in order. Combine ingredients of Part E and heat to 75-80° C. with stirring. Just prior to emulsification, add Part F and readjust temperature to 75-80° C. Add oil phase (combined Parts E and F) to water phase (combined Parts A-D) while homogenizing. Maintain temperature and agitation for at least 15 minutes. Cool to 55° C. and check for water loss. Cool to 45° C. with paddle mixer. Combine ingredients of Part G and add to the formulation. Cool to 30° C. and remove from heat.

Example 88

Foundation

The following is a prophetic example of a foundation formulation.

TABLE 24

Foundation

| | Ingredient | weight % |
|---|---|---|
| Part A | DI water | 54.33 |
| | Potassium hydroxide (10% aq. solution) | 1.3 |
| | Polysorbate 80 | 0.1 |
| Part B | Titanium dioxide | 7 |
| | Talc | 3.76 |
| | Yellow iron oxide | 0.8 |
| | Red iron oxide | 0.36 |
| | Black iron oxide | 0.09 |
| Part C | Propylene glycol | 2 |
| | Magnesium aluminum silicate | 1 |
| Part D | Propylene glycol | 4 |
| | Cellulose gum | 0.12 |
| Part E | Di-ppg-3 Myristyl ether adipate | 12 |
| | Alkyl ketal ester* | 4 |
| | Cetearyl alcohol, ceteth-20 phosphate, dicetyl phosphate | 3 |
| | Steareth-10 | 2 |
| | Cetyl alcohol | 0.62 |
| | Steareth-2 | 0.50 |
| Part F | Paraben-DU** | 1 |

*ketal examples: Ex. A, 2EH-LPK; Ex. B, 1N-LPK; Ex. C, 355TMH-LPK
**Paraben-DU - premixed broad-spectrum preservative blend (3 wt. % propylparaben, 11 wt. % methylparaben, 30 wt. % diazolidinyl urea, 56 wt. % propylene glycol).

To manufacture the example formulations, combine Part A and begin homogenizing. Pre-mill Part B until pigments are well blended. Add Part B to Part A and homogenize until pigments are evenly dispersed. Begin heating A/B. Prepare a slurry of Part C and add to Parts A/B and heat to 85° C., maintaining temperature in the 85-90° C. range for 10 minutes. Remove from heat and prepare a second slurry of the ingredients in Part D. Add the slurried of Part D to A/B/C at 77° C. Homogenize until uniform and smooth. Check weight and add water to compensate for any loss, plus another 20 g/kg of formulation. Continue mixing and increase temperature to 77 C. Combine Part E ingredients separately and heat to 77° C. Add to main mixture and maintain temperature at 77-80° C. for 10 minutes. Remove from heat. Add Part F when the mixture has cooled to 50° C. Check for water loss and adjust formulation accordingly. Adjust pH to 7.5 if necessary. Homogenize until temperature reaches 35° C.

Example 89

Concealer Stick

The following is a prophetic example of a concealer stick formulation

TABLE 25

Concealer Stick

| | Ingredient | weight % |
|---|---|---|
| Part A | Titanium dioxide (A-8112) | 20 |
| | Red iron oxide (A-1301) | 1.4 |
| | Red Iron Oxide (A-1226) | 0.65 |
| | Black iron oxide (A-7133) | 0.1 |
| | ketal * | 15.85 |
| | Di-PPG-3 Myristyl Ether Adipate | 4.25 |
| | Sorbitan Isostearate | 4.25 |
| Part B | Sericite AS | 10 |
| | Talc | 5 |
| | Di-PPG-3 Myristyl ether adipate | 2.5 |
| | Kaolin | 4 |
| Part C | Squalane | 3.5 |
| | Candelilla wax | 5 |
| | Ozokerite wax | 2.5 |
| | Propyl paraben | 0.1 |
| | Methyl paraben | 0.2 |
| | Carnauba wax | 1.75 |
| | C18-36 acid glycol ester | 2.25 |
| | C18-36 Acid Triglyceride | 1.1 |
| | Di-PPG-3 Myristyl ether Adipate | 14.6 |
| | DERMAXYL (from Croda) | 1 |

* ketal examples: Ex. A, 2EH-LPK; Ex. B, 1N-LPK; Ex. C, 355TMH-LPK

To manufacture the example formulations, grind the ingredients of Part A and homogenize for at least 15 minutes. Add the ingredients of Part B to Part A and mix for at least 10 minutes. Combine all of the ingredients of Part C in a separate vessel and begin heating while mixing. Continue heating until batch becomes clear. Begin cooling while mixing and add Parts A/B to the batch. Pre-warm the stick molds and pour the batch into molds while the batch is still pourable. Allow molds to cool.

Example 90

Diaper Rash Cream

The following is a prophetic example of a diaper rash cream formulation.

TABLE 26

Baby Soft Diaper Rash Cream

| | Ingredient | weight % |
|---|---|---|
| Part A | Squalane | 30 |
| | Ketal * | 5 |
| | Zinc oxide | 12 |
| | CRODAFOS CES (cetearyl alcohol, dicetyl phosphate, and ceteth-10 phosphate) | 6 |
| Part B | Deionized water | 44.10 |
| | Methylparaben, butylparaben, ethylparaben, and propylparaben | 0.3 |
| Part C | Dimethicone | 0.6 |

* ketal examples: Ex. A, 2EH-LPK; Ex. B, 1N-LPK; Ex. C, 355TMH-LPK

To manufacture the example formulations, disperse zinc oxide in the ketal and then add the other ingredients of Part A individually with mixing. Heat to 70-75° C. In a separate vessel, combine Part B and heat to 70-75° C. Add Part B to Part A and mix well. Begin cooling and add Part C with mixing when temperature reaches 50° C. Continue mixing and cool to desired fill temperature

Example 91

Strippers

The following Tables show prospective examples of formulations for a variety of uses as indicated. The amounts are in weight percent (wt %) based on the total weight of the formulations. The term "Ketal" is intended to cover 2EH-LPK, 1N-LPK or 355TMH-LPK.

General Purpose Stripper Formulation

| Component | Amount (wt %) |
|---|---|
| Ketal | 35 |
| Dimethyl sulfoxide (DMSO) | 29 |
| Dipropylene glycol methyl ether | 25 |
| Ethyl-3-ethoxypropionate (EEP) | 5 |
| Thickener | 1 |
| Surfactant | 5 |

Graffiti Removal Formulation

| Component | Amount (wt %) |
|---|---|
| DMSO | 35 |
| Solvesso ™ 150 ND* | 25-30 |
| Ketal | 25 |
| EEP | 8 |
| Surfactant | 4 |
| Thickener | 1-5 |

*ExxonMobil Corporation

Paint Stripper Formulation

| Component | Amount (wt %) |
|---|---|
| NMP | 40 |
| Ketal | 40 |
| Propylene glycol methyl ether acetate | 17 |
| Triton ™ X-100** | 0-2 |
| Klucel-H*** | 1 |

**The Dow Chemical Company
***Ashland, Inc.

Hand Cleaner Gel Formulation

| Component | Amount (wt %) |
|---|---|
| Ketal | 75 wt % |
| BIO-SOFT N1-7† | 15 |
| Viscos ABIT NATURAL†† | 10 |
| Fragrance | q.s. |

†Stepan Company
††React-NTI, LLC

Tar/Asphalt Remover Aerosol Formulation

| Component | Amount (wt %) |
|---|---|
| Aromatic 100 | 29 |
| Ketal | 50 |
| COLA ®COR 600 surfactant‡ | 1 |
| Isobutane propellant | 20 |

‡Colonial Chemical, Inc.

Parts Washer Formulation

| Component | Amount (wt %) |
|---|---|
| Methyl soyate | 50 |
| Ketal | 35 |
| d-limonene | 5 |
| BIO-SOFT N1-7† | 10 |

†Stepan Company

Engine Degreaser Formulation

| Component | Amount (wt %) |
|---|---|
| Soy methyl ester | 50.00 |
| Ketal | 15.00 |
| Ethoxylated nonyl phenol surfactant | 5.00 |
| Defoamer | 3.00 |
| Mineral oil | 27.00 |

Floor Mastic Remover Formulation

| Component | Amount (wt %) |
|---|---|
| Ketal | 75 |
| BIO-SOFT N25-9† | 25 |

†Stepan Company

| Concrete Oil Stain Remover Formulation | |
| --- | --- |
| Component | Amount (wt %) |
| Ketal | 75 |
| BIO-SOFT N25-9† | 25 |

†Stepan Company

Example 92

Cleaner Formulation

An exemplary cleaner formulation can be prepared by combining the following components in a 20 ml scintillation vial: 4 parts ketal (Example 92A—2EH-LPK, and Example 92B—1N-LPK, example 92C—355TMH-LPK); 4.5 parts nonionic surfactant (Biosoft N91-6, Stepan Co., Northfield, Ill.); 0.5 parts sodium citrate dihydrate (Fisher Scientific, a division of Thermo Fisher Scientific; Waltham, Mass.), and the balance of the formulation being water.

Example 93

Method of Forming a Dispersion with Pigment

Using an overhead mixer with a Cowles blade, Ti-pure R960 titanium dioxide (DuPont) is slowly added to solvent as shown in Table 27, mixing between additions until the viscosity is uniform. After additional mixing for the reported period of time, the dispersion quality is measured on a Hegman grind block. Additional solvent (amount not reported) is added to achieve a pourable viscosity, and the viscosity of the dispersion is measured on a Brookfield viscometer.

TABLE 27

| Ex. | Solvent | Pigment (g) | Solvent (g) | Mix Speed (rpm) | Mix Time (min) | Dispersion Quality |
| --- | --- | --- | --- | --- | --- | --- |
| 6A | DPM Acetate | 200 | 300 | 800 | 3 | 7.5 |
| 6B | Ketal* | 200 | 300 | 800 | 3 | 7.5 |

*ketal examples: Ex. A, 2EH-LPK; Ex. B, 1N-LPK; Ex. C, 355TMH-LPK

Example 94

Coating Formulations

Coating formulations are made using a Cowles blade on an overhead mixer as shown in the Tables below. The formulas below are made by adding the ingredients in order. The grind paste portion is made and put under shear until the proper dispersion is achieved of 7+Hegman. Then the remaining ingredients are added to complete the formulation. The ingredients are loaded into the vessel and a Dupont Ti-pure R960 Titanium Dioxide is loaded into the mixture slowly until the viscosity is uniform and the mixing solution makes a donut upon mixing. After mixing for a period of time, an amount of the mixture is deposited on a Hegman grind block and a measurement of the dispersion is read. All of the systems should have Hegman readings of 7.5 or better. Then the remaining ingredients are added to complete the formula.

TABLE 28

Formula 94-1A-C- Polyester Melamine

| | | Comparative Example | | |
| --- | --- | --- | --- | --- |
| | Ingredient | 94-1A* Formula | 94-1B Formula | 94-1C |
| Saturated Polyester resin | Polymac 57-5789 | 45.73 | 45.73 | 45.73 |
| Melamine resin | Cymel 300 | 7.53 | 7.53 | 7.53 |
| Titanium Dioxide | Ti-pure R960 | 28.79 | 28.79 | 28.79 |
| grind paste | | 82.05 | 82.05 | |
| Solvent | DPM acetate | 3.91 | 3.91 | 0 |
| Solvent | DBE | 3.91 | 0 | 0 |
| | Ketal** | 0 | 3.91 | 7.82 |
| Hydrocarbon Solvent | BAS 150 | 7.73 | 7.73 | 7.73 |
| Catalyst | Nacure 1051 | 0.40 | 0.40 | 0.40 |
| Solvent | Optifilm 300 | 2.00 | 2.00 | 2.00 |
| Total | | 100.00 | 100.00 | 100.00 |

*Comparative Example
**ketal examples: Ex. A, 2EH-LPK Ex. B, 1N-LPK Ex. C, 355TMH-LPK

TABLE 29

Formula 94-2A-B - 1K Polyester urethane

| | | Comparative Example | |
| --- | --- | --- | --- |
| | Ingredient | 94-2A* Formula | 94-2B |
| Polyester resin | Polymac HS57-5789 | 43.72 | 43.72 |
| Rheology additive | Aerosil 200 | 0.29 | 0.29 |
| Titanium Dioxide | Ti-pure R960 | 19.28 | 19.28 |
| grind paste | | 63.29 | 63.29 |
| Blocked isocyanate | Desmodur BL3175 | 1.95 | 1.95 |
| tin catalyst | Dabco T12 | 1.08 | 1.08 |
| epoxy resin | Epon 828 | 1.31 | 1.31 |
| Solvent | BAS 150 | 10.76 | 10.76 |
| Solvent | DBE | 8.37 | 0 |
| Solvent | Ketal** | 0 | 8.37 |
| Solvent | Diacetone alcohol | 4.78 | 4.78 |
| Total | | 91.54 | 91.54 |

*Comparative
**ketal examples: Ex. A, 2EH-LPK; Ex. B, 1N-LPK; Ex. C, 355TMH-LPK

TABLE 30

Formula 94-3A-B - 2K Polyester Urethane

| | | Comparative Example | |
| --- | --- | --- | --- |
| | Ingredient | 94-3A* Formula | 94-3BB Formula |
| PART A | | | |
| Acrylic resin | Joncryl 500 | 200.00 | 200.00 |
| Leveling agent | BYK 320 | 2.00 | 2.00 |
| Solvent | MAK | 40.00 | 0 |
| Solvent | Ketal** | 0 | 40.00 |
| Pigment Grind paste | Ti-Pure R-960 | 329.00 | 329.00 |
| Acrylic resin | Joncryl 500 | 199.60 | 199.60 |
| Solvent | MAK | 116.10 | 116.10 |
| tin catalyst | Dabco T12 | 0.23 | 0.23 |
| Subtotal | | 886.93 | 886.93 |

TABLE 30-continued

Formula 94-3A-B - 2K Polyester Urethane

|  |  | Comparative Example | |
| --- | --- | --- | --- |
| | Ingredient | 94-3A*<br>Formula | 94-3BB<br>Formula |
| PART B | | 3B | 3B |
| Aliphatic isocyanate | Desmodur N3300 | 152.60 | 152.60 |
| Solvent | MAK | 29.20 | 29.20 |
| Total | | 1068.73 | 1068.73 |

*Comparative
**ketal examples: Ex. A, 2EH-LPK; Ex. B, 1N-LPK; Ex. C, 355TMH-LPK

After allowing the formulations to set overnight, observations are made regarding the material stability. All formulas should show minimal separation that is easy to mix to uniformity. Using a drawdown bar over steel Q-panels, film thicknesses of 1 and 3 mils are made using each of the formulations. The panels are put into a 200° C. oven for 60 minutes. The final film is evaluated for appearance, cross-hatch adhesion, and Methyl Ethyl Ketone double rubs. The cross-hatch adhesion is carried out per ASTM D3359 and the MEK double rubs are carried out per ASTM method D5402-06. The double rubs are performed using a rag that is soaked with MEK and then the number of double rubs is counted to see the effects on the coating. If the coating is worn away to the substrate, the testing is discontinued and number is reported.

Examples 95-98

Examples 95-98 evaluated the use of 2EH-LPK, 1N-LPK and 355TMH-LPK as a coalescing agent for an alkyd polymer binder that is neutralized. Thus, in the following examples, triethylamine (TEA) is added in an amount sufficient to stoichiometrically neutralize 100% of the acid groups on the alkyd polymer binder. The components of each example in Table 31 are weighed into a vial and agitated by shaking by hand at room temperature (approximately 73° F.) with the indicated amount of deionized (DI) water.

TABLE 31

| Example | Solvent | Solvent (g) | Duramac ® WR216-3610 (g) | DI water (g) | TEA (g) |
| --- | --- | --- | --- | --- | --- |
| 95 | None | 0 | 5 | 5 | 0.765 |
| 96 | Ketal* | 0.75 | 4.25 | 5 | 0.65 |
| 97 | None | 0 | 2.5 | 7.5 | 0.3825 |
| 98 | Ketal* | 0.375 | 2.125 | 7.5 | 0.325 |

*ketal examples: Ex. A, 2EH-LPK; Ex. B, 1N-LPK; Ex. C, 355TMH-LPK

Examples 99-102

Examples 99-102 evaluate the use of 2EH-LPK, 1N-LPK and 355TMH-LPK as a coalescing agent for a one-part polyurethane dispersion, Hauthane™ HD 4669 from Hauthaway, which is a co-solvent free, aliphatic polyester polyurethane dispersion at 38% solids (±1%) that provides a hard coating, and is designed for topcoat applications on a wide variety of substrates, including concrete, metal, plastic, and wood.

Compositions with Hauthane® HD-4675 are mixed by hand according to the examples in Table 32. Films are drawn onto polished steel panels (Q-Panel® from Q-Lab) with a drawdown bar with a thickness of 5 mil (127 micrometer). The panels are left on the bench to dry at room temperature.

TABLE 32

| Example | Solvent | Wt. % Solvent | Wt. % Hauthane ® HD-4675 |
| --- | --- | --- | --- |
| 99 | None | 0 | 100 |
| 100 | 2EH-LPK | 0.5 | 99.5 |
| 101 | 1N-LPK | 0.5 | 99.5 |
| 102 | 355TMH-LPK | 0.5 | 99.5 |

Examples 103-105

Examples 103-105 are evaluated the use of 2EH-LPK, 1N-LPK and 355TMH-LPK as a coalescing agent for a one-part polyurethane dispersion, Hauthane® HD-4669 (from Hauthaway), a cosolvent-free, aliphatic, aqueous polyurethane dispersion at 40% solids (±1%) that forms a hard coating wherein heat curing is recommended, and is designed for topcoat applications on a wide variety of substrates, including concrete, metal, plastic, and wood, either as a sole vehicle or blended with acrylic emulsions.

In Example 103, Hauthane® HD-4669 (95 wt. %) is mixed by hand with 2EH-LPK (5 wt. %). A film is drawn on polished steel panels (Q-Panel® from Q-Lab) with a drawdown bar with a thickness of 5 mil (127 micrometer). The panel is cured in an oven at 200° C. for 60 minutes. After the oven cure, the compositions forms a hard, smooth film.

In Example 104, Hauthane® HD-4669 (95 wt. %) is mixed by hand with 1N-LPK (5 wt. %). A film is drawn on polished steel panels (Q-Panel® from Q-Lab) with a drawdown bar with a thickness of 5 mil (127 micrometer). The panel is cured in an oven at 200° C. for 60 minutes. After the oven cure, the compositions forms a hard, smooth film.

In Example 105, Hauthane® HD-4669 (95 wt. %) is mixed by hand with 355TMH-LPK (5 wt. %). A film is drawn on polished steel panels (Q-Panel® from Q-Lab) with a drawdown bar with a thickness of 5 mil (127 micrometer). The panel is cured in an oven at 200° C. for 60 minutes. After the oven cure, the compositions form a hard, smooth film.

The terminology used herein is for the purpose of describing particular embodiments only and is not intended to be limiting. As used herein, the singular forms "a," "an," and "the" are intended to include the plural forms as well, unless the context clearly indicates otherwise. "Or" means "and/or." The endpoints of all ranges directed to the same component or property are inclusive of the endpoint and independently combinable.

Unless otherwise defined, all terms (including technical and scientific terms) used herein have the same meaning as commonly understood by one of ordinary skill in the art to which this invention belongs. The term "paint" includes any protective exterior coatings that are also known as, for example, lacquer, electropaint, shellac, top coat, base coat, color coat, and the like.

The compounds made by the above-described methods have, in embodiments, one or more isomers. Where an isomer can exist, it should be understood that the invention embodies methods that form any isomer thereof, including any stereoisomer, any conformational isomer, and any cis, trans isomer; isolated isomers thereof; and mixtures thereof.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. Unless otherwise specified, alkyl groups may be straight-chained or branched. Throughout the specification, reference is made to various bivalent groups. Such groups are the same as the monovalent groups that are similarly named, and are typically indicated with an "ene" suffix. For example, a C7 to C18 alkylene group is a bivalent linking group having the same structure as a C7 to C18 alkyl group.

All cited patents, patent applications, and other references are incorporated herein by reference in their entirety.

The various embodiments described above are provided by way of illustration only and should not be construed to limit the claims attached hereto. The present invention can suitably comprise, consist of, or consist essentially of, any of the disclosed or recited elements. Thus, the invention illustratively disclosed herein can be suitably practiced in the absence of any element which is not specifically disclosed herein. Various modifications and changes will be recognized that can be made without following the example embodiments and applications illustrated and described herein, and without departing from the true spirit and scope of the following claims.

What is claimed is:

1. A compound of formula (1):

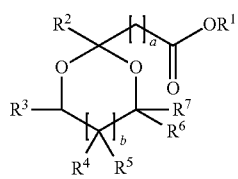

(1)

wherein
R$^1$ is a 2-ethylhexyl, 1-nonyl, or 3,5,5-trimethylhexyl group,
R$^2$ is hydrogen or a C$_{1-3}$ alkyl,
each R$^3$, R$^4$, R$^5$, R$^6$, and R$^7$ is independently hydrogen or a C$_{1-6}$ alkyl,
a is 2-3, and
b is 0-1.

2. The compound of claim 1, wherein R$^2$ is methyl, each R$^3$, R$^4$, R$^5$, and R$^6$ is hydrogen or a C$_{1-3}$ alkyl, R$^7$ is hydrogen, a is 2-3, and b is 0-1.

3. The compound of claim 1, wherein R$^2$ is methyl, each R$^3$, R$^4$, and R$^5$ is hydrogen, R$^6$ is hydrogen or a C$_{1-3}$ alkyl, R$^7$ is hydrogen, a is 2, and b is 0-1.

4. The compound of claim 1, wherein R$^2$ is methyl, R$^3$ is hydrogen, R$^6$ is hydrogen, methyl, or ethyl, R$^7$ is hydrogen, a is 2, and b is 0.

5. The compound of claim 1, wherein the compound is of formula (1a)

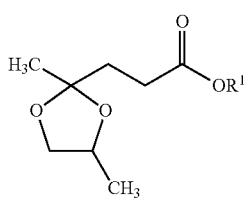

(1a)

wherein R$^1$ is a 2-ethylhexyl 1-nonyl, or 3 5 5-trimethylhexyl group.

6. A method of making the compound of claim 1, the method comprising contacting a ketoacid ester of formula (2)

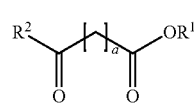

(2)

with a diol of formula (3)

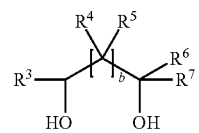

(3)

under reaction conditions effective to form a compound of formula (1) or transesterifying a compound of formula (4)

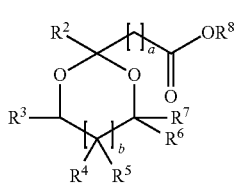

(4)

wherein R$^8$ is a C$_{1-6}$ alkyl group, with an alcohol of the formula R$^1$—OH to form the compound of formula (1) and wherein R$^1$, R$^2$, R$^3$, R$^4$, R$^5$, R$^6$, and R$^7$, a, and b are as defined in claim 1.

7. A coating composition comprising water; a polymer binder; and a compound of formula (1):

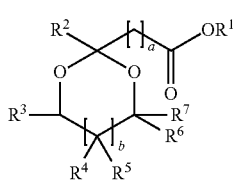

(1)

wherein
R$^1$ is a C$_{7-18}$ alkyl,
R$^2$ is hydrogen or a C$_{1-3}$ alkyl,
each R$^3$, R$^4$, R$^5$, R$^6$, and R$^7$ is independently hydrogen or a C$_{1-6}$ alkyl,
a is 2-3, and
b is 0-1; and further
wherein the coating composition comprises less than or equal to about 250 g/l VOC as determined using ASTM Method D3960.

8. The coating composition of claim 7, wherein the composition is a paint composition, an adhesive composition, a sealant composition, a clear coat composition, a stain composition, a caulk composition, or an ink composition.

9. The coating composition of claim 7, wherein R$^1$ is a 2-ethylhexyl, 1-nonyl, or 3,5,5-trimethylhexyl group.

10. The coating composition of claim 7, having a pH of about 7.5 to about 10.

11. The coating composition of claim 7, comprising
a latex polymer binder;
water; and
the compound of formula (1),
wherein the composition is a latex paint composition.

12. The coating composition of claim 11, comprising about 0.1 to about 30 wt. % of the compound of formula (1) based on the dry weight of the latex polymer binder.

13. The coating composition of claim 11, wherein the latex polymer binder comprises an emulsion polymer containing units derived from polymerization of vinyl acetate, acrylic acid, an acrylic acid $C_{1-4}$ alkyl ester, methacrylic acid, or a methacrylic acid $C_{1-4}$ alkyl ester, optionally with units derived from styrene, a-methyl styrene, vinyl chloride, acrylonitrile, methacrylonitrile, ureido methacrylate, vinyl acetate, itaconic acid, crotonic acid, maleic acid, fumaric acid, ethylene, hydroxyethyl acrylate, hydroxypropyl acrylate, a $C_{4-8}$ conjugated diene, vinyl versatate, or a combination thereof.

14. The coating composition of claim 11, wherein the latex polymer binder comprises an acrylic, styrene-acrylic, vinyl acetate, vinyl-acrylic, or acrylated ethylene-vinyl acetate emulsion polymer.

15. The coating composition of claim 13, wherein the latex polymer binder is a vinyl acetate emulsion polymer.

16. A coating composition of claim 7, comprising:
a water-reducible polymer binder;
water; and
the compound of formula (1)
wherein the composition is a water-reducible coating composition.

17. The coating composition of claim 16, comprising about 0.1 to about 30 wt. % of the compound of formula (1) based on the dry weight of the polymer binder.

18. A method of coating a substrate comprising contacting a coating composition of claim 7, with a surface of a substrate to form a coating; and drying the coating.

19. A coated substrate made by the method of claim 18.

20. A cleaning or personal care composition comprising
a cleaning or personal care component; and
the compound of claim 1.

21. The composition of claim 20, wherein the compound is of formula (1 a)

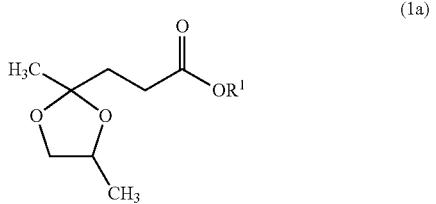

(1a)

wherein $R^1$ is a 2-ethylhexyl, 1-nonyl, or a 3,5,5-trimethylhexyl group.

22. The composition of claim 20, wherein the composition is a cleaning composition, and the cleaning component is a cosolvent, a plurality of abrasive particles, an organic amine, an antioxidant, a biocide, a colorant, a corrosion inhibitor, a defoamer, a dye, an enzyme, a light stabilizer, an odor masking agent, a plasticizer, a preservative, a rust inhibitor, a surfactant, a thickener, a soil suspending agent, a builder, a chelating agent, a bleach, a bleach activator, a bleach stabilizer, a pH control agent, a hydrotrope, a fabric softener, or a combination comprising at least one of the foregoing.

23. The composition of claim 22, wherein the composition is a laundry detergent, hard surface cleaner, soft surface cleaner, dishwasher cleaner, glass cleaner, oven cleaner, concrete cleaner, form cleaner, mold cleaner, paint remover, graffiti remover, ink remover, sealant remover, adhesive remover, mastic remover, photoresist remover, wax remover, asphalt remover, sap remover, oil remover, grease remover, or a combination comprising at least one of the foregoing.

24. The composition of claim 20, wherein the composition is a personal care composition, and the personal care component is an active agent, a cosmetic colorant, a surfactant, or a combination comprising at least one of the foregoing.

25. A personal care composition comprising
a personal care component; and
a compound of formula (1)

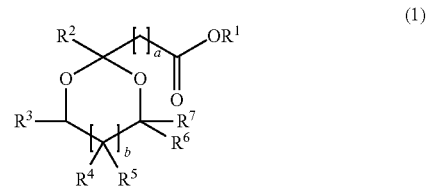

(1)

wherein
$R^1$ is a $C_{7-18}$ alkyl,
$R^2$ is hydrogen or a $C_{1-3}$ alkyl,
each $R^3$, $R^4$, $R^5$, $R^6$, and $R^7$ is independently hydrogen or a $C_{1-6}$ alkyl,
a is 2-3, and
b is 0-1;
wherein the personal care component is an active agent, a cosmetic colorant, a surfactant, or a combination comprising at least one of the foregoing; and
wherein the active agent is an anti-aging agent, anti-acne agent, skin whitener, ultraviolet light absorber, tanning agent, anti-alopecia agent, antifungal agent, anti-dandruff agent, anti-perspirant, antimicrobial, organic medicinal, depilatory compound, hair dye, insect repellant, or a combination comprising at least one of the foregoing.

26. The composition of claim 24, wherein the composition is a shampoo, a body cleaner, an eye care product, a cosmetic, a fragrance, a hair coloring formulation, a hair straightening or permanent wave formulation, a nail care formulation, a toothpaste, a mouthwash, a shave cream, a skin care formulation, a sun care formulation, a lip care formulation, an antiperspirant, or a foot care formulation.

27. A fragrant composition comprising:
at least one fragrant composition; and
the compound of claim 1.

28. The fragrant composition of claim 27, wherein the compound is of formula (1a)

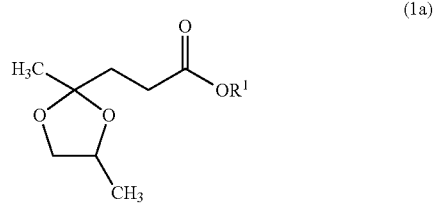

(1a)

wherein $R^i$ is a 2-ethylhexyl, 1-nonyl, or 3,5,5-trimethylhexyl group.

29. A coating composition comprising water;
a polymer binder; and
a compound of claim 1.

30. The coating composition of claim 29 comprising:
a latex polymer binder;
water; and
a compound of claim 1;
wherein the composition is a latex paint composition.

31. The coating composition of claim 29 comprising:
a water-reducible polymer binder;
water; and
a compound of claim 1;
wherein the composition is a water-reducible coating composition.

* * * * *